US008609727B2

(12) United States Patent
Bartel et al.

(10) Patent No.: US 8,609,727 B2
(45) Date of Patent: Dec. 17, 2013

(54) DICARBOXYLIC ACID DERIVATIVES AND THEIR USE

(75) Inventors: Stephan Bartel, Kürten (DE); Michael Hahn, Langenfeld (DE); Wahed Ahmed Moradi, Monheim (DE); Eva-Maria Becker, Wuppertal (DE); Thomas Rölle, Leverkusen (DE); Johannes-Peter Stasch, Solingen (DE); Karl-Heinz Schlemmer, Wuppertal (DE); Frank Wunder, Wuppertal (DE); Andreas Knorr, Erkrath (DE); Dieter Lang, Velbert (DE)

(73) Assignee: Bayer Intellectual Property GmbH, Monheim (DE)

( * ) Notice: Subject to any disclaimer, the term of this patent is extended or adjusted under 35 U.S.C. 154(b) by 764 days.

(21) Appl. No.: 12/083,814

(22) PCT Filed: Oct. 17, 2006

(86) PCT No.: PCT/EP2006/009996
§ 371 (c)(1),
(2), (4) Date: Oct. 19, 2009

(87) PCT Pub. No.: WO2007/045433
PCT Pub. Date: Apr. 26, 2007

(65) Prior Publication Data
US 2010/0029772 A1    Feb. 4, 2010

(30) Foreign Application Priority Data
Oct. 21, 2005    (DE) .................... 10 2005 050 376

(51) Int. Cl.
*A01N 37/10* (2006.01)
*A01N 31/14* (2006.01)
*A01N 47/10* (2006.01)
*A61K 31/19* (2006.01)
*A61K 31/075* (2006.01)
*A61K 31/27* (2006.01)

(52) U.S. Cl.
USPC .................... 514/568; 514/717; 562/488

(58) Field of Classification Search
USPC .................... 514/568, 717; 562/488
See application file for complete search history.

(56) References Cited

U.S. PATENT DOCUMENTS

| 6,180,656 | B1 | 1/2001 | Furstner et al. |
| 6,387,940 | B1 | 5/2002 | Straub et al. |
| 6,410,740 | B1 | 6/2002 | Straub et al. |
| 6,414,009 | B1 | 7/2002 | Straub et al. |
| 6,451,805 | B1 | 9/2002 | Straub et al. |
| 6,462,068 | B1 | 10/2002 | Straub et al. |
| 6,864,287 | B1 | 3/2005 | Alonso-Alija et al. |
| 7,087,644 | B1 | 8/2006 | Alonso-Alija et al. |
| 7,998,988 | B2 | 8/2011 | Bartel et al. |
| 2003/0105097 | A1* | 6/2003 | Simon et al. ........... 514/231.2 |
| 2004/0082798 | A1 | 4/2004 | Alonso-Alija et al. |
| 2004/0176446 | A1 | 9/2004 | Alonso-Alija et al. |
| 2007/0179139 | A1 | 8/2007 | Alonso-Alija et al. |
| 2008/0058314 | A1 | 3/2008 | Alonso-Alija et al. |

FOREIGN PATENT DOCUMENTS

| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | WO 01/19355 A2 | 3/2001 |
| WO | WO-01/19776 A2 | 3/2001 |
| WO | WO-01/19778 | 3/2001 |
| WO | WO-01/19780 | 3/2001 |
| WO | WO 0119778 A1 * | 3/2001 |
| WO | WO-02/070462 A1 | 9/2002 |
| WO | WO-02/070510 A2 | 9/2002 |

OTHER PUBLICATIONS

Patani et al. "Bioisosterism: A Rational Approach in Drug Design" Chem. Rev., 1996, vol. 96, pp. 3147-3176.*
U.S. Appl. No. 12/083,509, filed Jul. 6, 2009.
U.S. Appl. No. 12/085,543, filed Feb. 17, 2009.
U.S. Appl. No. 12/529,342, filed Mar. 25, 2010.
Demko, et al., "Preparation of 5-substituted 1H-tetrazoles from nitriles in water," J. Org. Chem. 2001, 66: 7945-7950.
Patani et al., "Bioisterism: A rational Approach in Drug Design," Chem. Rev., 1996, 96: 3147-3176.
FN Ko et al.: "YC-1, A Novel Activator of Platelet Guanylate Cyclase," Blood, 84, 1994, pp. 4226-4233.
A. Mulsch et al.: "Effect of YC-1, an NO-independent, superoxide-Sensitive Stimulator of Soluble Guanylyl Cyclase, on Smooth Muscle Responsiveness to Nitrovasodilators," British Journal of Pharmacology, 120, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.
D. J. Pettibone et al.: "A Structurally Novel Stimulator of Guanylate Cyclase with Long-Lasting Hypotensive Activity in the Dog," European Journal of Pharmacology, 116, 1985, pp. 307-312.
S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.
R. Gerzer et al.: "Soluble Guanylate Cyclase Purified from Bovine Lung Contains Heme and Copper," FEBS Letters, vol. 132, No. 1, Sep. 1981, pp. 71-74.
M. Hoenicka et al.: "Purified Soluble Guanylyl Cyclase Expressed in a Baculovirus/Sf9 System: Stimulation by YC-1, Nitirc Oxide, and Carbon Monoxide," J. Mol. Med, 77, 1999, pp. 14-23.
L. J. Ignarro: "Regulation of Cytosolic Guanylyl Cyclase by Porphyrins and Metalloporphyrins," Advances in Pharmacology, vol. 26, 1994, pp. 35-65.
A. Mulsch et al.: "Potentiation of Vascular Responses to Non-Donors by An No-Independent Activator of Soluble Guanylyl Cyclase," Naunyn Schmiedebergs Arch. Pharmacol. 355, R47.

* cited by examiner

*Primary Examiner* — Kendra D Carter
(74) *Attorney, Agent, or Firm* — Karen B. King

(57) ABSTRACT

The present application relates to novel dicarboxylic acid derivatives, process for their preparation, their use for the treatment and/or prophylaxis of diseases, and their use for producing medicaments for the treatment and/or prophylaxis of diseases, especially for the treatment and/or prevention of cardiovascular disorders.

9 Claims, No Drawings

DICARBOXYLIC ACID DERIVATIVES AND THEIR USE

This application is a National Stage Application filed under 35 U.S.C. §371 based on International Application No. PCT/EP2006/009996, filed Oct. 17, 2006, which claims priority to German Patent Application Number 102005050376.4 filed Oct. 21, 2005, the entire contents each of which are incorporated herein by reference. The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel dicarboxylic acid derivatives, process for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. CO is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signalling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223, WO 98/16507 and WO 98/23619).

The above-described stimulators of soluble guanylate cyclase stimulate the enzyme either directly via the haem group (carbon monoxide, nitric oxide or diphenyliodonium hexafluorophosphate) by interacting with the iron centre of the haem group and a change in conformation which results therefrom and leads to an increase in the enzymic activity [Gerzer et al., *FEBS Lett.* 132 (1981), 71] or via a haem-dependent mechanism which is independent of NO but leads to a potentiation of the stimulating effect of NO or CO [e.g. YC-1, Hoenicka et al., *J. Mol. Med.* 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf., for example, Hoenicka et al., *J. Mol. Med.* 77 (1999), 14].

If the haem group is removed from soluble guanylate cyclase, the enzyme still shows a detectable basal catalytic activity, i.e. cGMP is still produced. The remaining basal catalytic activity of the haem-free enzyme cannot be stimulated by any of the aforementioned known stimulators.

Stimulation of haem-free soluble guanylate cyclase by protoporphyrin IX has been described [Ignarro et al., *Adv. Pharmacol.* 26 (1994), 35]. However, protoporphyrin IX can be regarded as a mimic of the NO-haem adduct, which is why addition of protoporphyrin DC to soluble guanylate cyclase ought to lead to production of a structure of the enzyme corresponding to the haem-containing soluble guanylate cyclase which is stimulated by NO. This is also verified by the fact that the stimulating effect of protoporphyrin IX is increased by the NO-independent but haem-dependent stimulator YC-1 described above [Mülsch et al., *Naunyn Schmiedebergs Arch. Pharmacol.* 355, R47].

In contrast to the above-described stimulators of soluble guanylate cyclase, the compounds of the present invention are able to activate both the haem-containing and the haem-free form of soluble guanylate cyclase. Thus, with these novel activators, the enzyme is stimulated via a haem-independent pathway, which is also verified by the facts that the novel activators firstly show no synergistic effect with NO on the haem-containing enzyme, and secondly the effect of these novel activators cannot be blocked by the haem-dependent inhibitor of soluble guanylate cyclase 1H-1,2,4-oxadiazole-(4,3-a)-quinoxalin-1-one (ODQ).

EP 0 341 551-A1 discloses alkenoic acid derivatives as leucotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

This object is achieved by the compounds described in the present invention. These compounds are distinguished structurally from the prior art compounds by a core 3-benzyl-1,5-diphenylpent-1-ene structure.

Specifically, the present invention relates to compounds of the general formula (I)

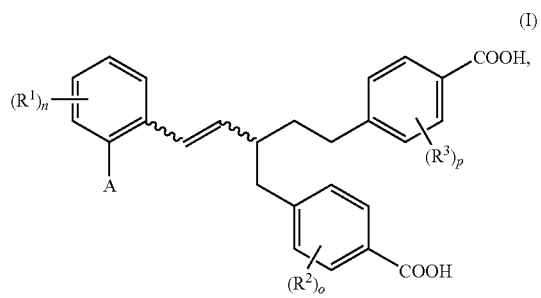

in which
A is hydrogen or is a group of the formula —O-$A^1$-$A^2$ in which
  $A^1$ is a bond or ($C_1$-$C_7$)-alkanediyl, ($C_2$-$C_6$)-alkanediyl-O-#, ($C_2$-$C_7$)-alkenediyl or ($C_2$-$C_7$)-alkynediyl, each of which may be substituted one or more times by fluorine, and in which # represents the point of linkage to the group $A^2$,
and
$A^2$ is hydrogen, trifluoromethyl or a group of the formula

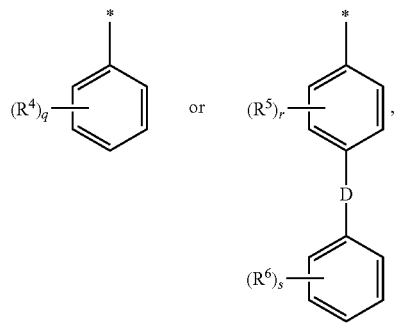

in which * is the point of linkage to the group $A^1$ and
  D is a bond, $CH_2$, —$CH_2$—$CH_2$— or —CH=CH—,
$R^1$, $R^2$, $R^3$, $R^5$ and $R^6$ are independently of one another a substituent selected from the series halogen, ($C_1$-$C_6$)-alkyl, trifluoromethyl, ($C_1$-$C_6$)-alkoxy, trifluoromethoxy, cyano and nitro,
$R^4$ is a substituent selected from the series halogen, ($C_1$-$C_6$)-alkyl, ($C_1$-$C_6$)-alkoxy, cyano and nitro, where alkyl and alkoxy may in each case be substituted one or more times by fluorine,
and
n, o, p, q, r and s are in each case independently of one another the number 0, 1, 2, 3 or 4,
  where in the case where $R^1$, $R^2$, $R^3$, $R^4$, $R^5$ or $R^6$ occur more than once, their meanings may in each case be identical or different,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

The group

in formula (I) means that this CC double bond may be present in a cis or in a trans configuration. Both isomeric forms are encompassed by the present invention. Preferred compounds of the formula (I) have a trans arrangement of this double bond.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_1-C_7)$-Alkanediyl and $(C_2-C_6)$-alkanediyl are in the context of the invention a straight-chain or branched divalent alkyl radical having respectively 1 to 7 and 2 to 6 carbon atoms. A straight-chain alkanediyl radical having 1 to 6 or 2 to 5 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

$(C_2-C_7)$-Alkenediyl is in the context of the invention a straight-chain or branched divalent alkenyl radical having 2 to 7 carbon atoms and up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

$(C_2-C_7)$-Alkynediyl is in the context of the invention a straight-chain or branched divalent alkynyl radical having 2 to 7 carbon atoms and up to 3 triple bonds. A straight-chain alkynediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

$(C_1-C_4)$-Alkoxycarbonyl is in the context of the invention a straight-chain or branched alkoxy radical having 1 to 4 carbon atoms which is linked via a carbonyl group. Examples which may be preferably mentioned are: methoxycarbonyl, ethoxycarbonyl, n-propoxycarbonyl, isopropoxycarbonyl and tert-butoxycarbonyl.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

If a radical in the compounds according to the invention can be substituted more than once by fluorine, in the context of the present invention this includes perfluoro substitution.

Preference is given in the context of the present invention to compounds of the formula (I) in which A is hydrogen or is a group of the formula —O-A$^1$-A$^2$ in which A$^1$ is a bond, $(C_1-C_7)$-alkanediyl, $(C_2-C_7)$-alkenediyl or $(C_2-C_7)$-alkynediyl and A$^2$ is hydrogen, trifluoromethyl or a group of the formula

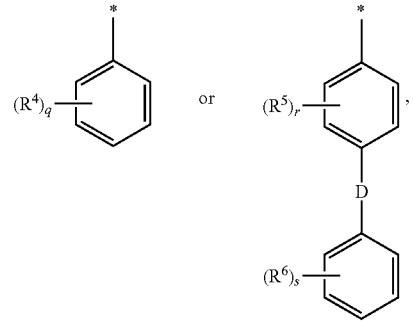

in which * is the point of linkage to the group A$^1$ and

D is a bond, CH$_2$, —CH$_2$—CH$_2$— or —CH=CH—,

R$^1$, R$^2$, R$^3$, R$^4$, R$^5$ and R$^6$ are independently of one another a substituent selected from the series halogen, $(C_1-C_6)$-alkyl, trifluoromethyl, $(C_1-C_6)$-alkoxy, trifluoromethoxy, cyano and nitro, and n, o, p, q, r and s are in each case independently of one another the number 0, 1, 2, 3 or 4, where in the case where R$^1$, R$^2$, R$^3$, R$^4$, R$^5$ or R$^6$ occur more than once, their meanings may in each case be identical or different, and the salts, solvates and solvates of the salts thereof.

Particular preference is given in the context of the present invention to compounds of the formula (I) in which A is a group of the formula —O-A$^1$-A$^2$ in which A$^1$ is a bond or $(C_1-C_7)$-alkanediyl and A$^2$ is hydrogen, trifluoromethyl or a group of the formula

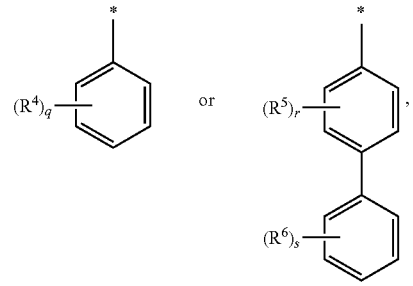

in which * is the point of linkage to the group A$^1$,

R$^1$, R$^4$, R$^5$ and R$^6$ are independently of one another a substituent selected from the series fluorine, chlorine, bromine, $(C_1-C_4)$-alkyl, trifluoromethyl, $(C_1-C_4)$-alkoxy and trifluoromethoxy, n, q, r and s are in each case independently of one another the number 0, 1 or 2, where in the case where $R^1$, $R^4$, $R^5$ or $R^6$ occur more than once, their meanings may in each case be identical or different, $R^2$ and $R^3$ are each fluorine, and o and p are in each case independently of one another the number 0 or 1, and the salts, solvates and solvates of the salts thereof.

Very particular preference is given in the context of the present invention to compounds of the formula (I-A)

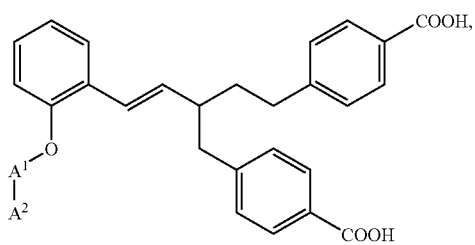

(I-A)

in which $A^1$ is $(C_1\text{-}C_7)$-alkanediyl and $A^2$ is hydrogen or a group of the formula

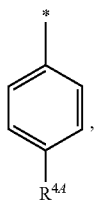

in which * is the point of linkage to the group $A^1$ and $R^{4.4}$ is hydrogen, fluorine, chlorine, methyl, tert-butyl, trifluoromethyl, methoxy or trifluoromethoxy, and the salts, solvates and solvates of the salts thereof.

Very particular preference is also given in the context of the present invention to compounds of the formula (I-B)

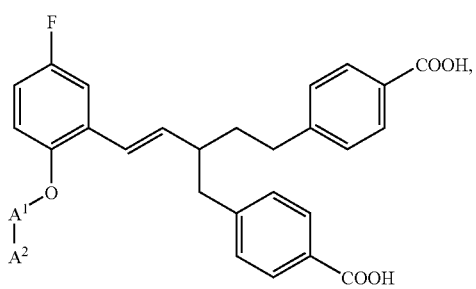

(I-B)

in which $A^1$ is $(C_1\text{-}C_7)$-alkanediyl and $A^2$ is hydrogen or a group of the formula

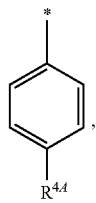

in which * is the point of linkage to the group $A^1$ and $R^{4.4}$ is hydrogen, fluorine, chlorine, methyl, tert-butyl, trifluoromethyl, methoxy or trifluoromethoxy, and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds according to the invention of the formula (I), characterized in that compounds of the formula (II)

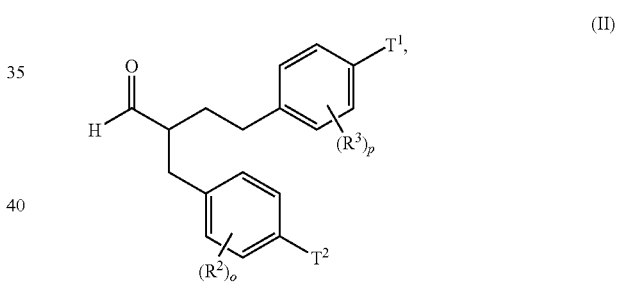

(II)

in which $R^2$, $R^3$, o and p each have the meanings indicated above, and $T^1$ and $T^2$ are identical or different and are cyano or $(C_1\text{-}C_4)$-alkoxycarbonyl, either

[A] are reacted in an inert solvent in the presence of a base with a compound of the formula (III-A)

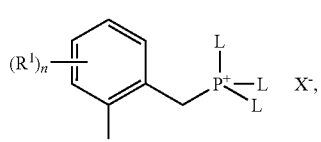

(III-A)

in which A, $R^1$ and n each have the meanings indicated above, and

L is phenyl or o-, m- or p-tolyl and

X is halide or tosylate, to give compounds of the formula (IV-A)

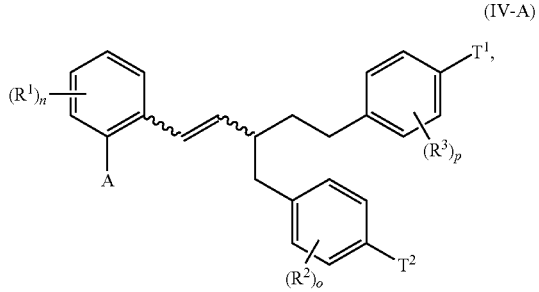

in which A, $R^1$, $R^2$, $R^3$, n, o, p, $T^1$ and $T^2$ each have the meanings indicated above, or

[B] are reacted in an inert solvent in the presence of a base with a compound of the formula (III-B)

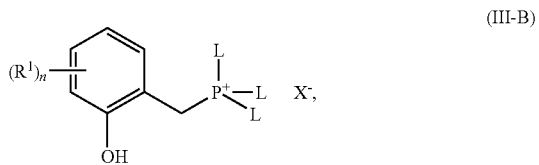

in which $R^1$, n, L and X each have the meanings indicated above, initially to give compounds of the formula (IV-B)

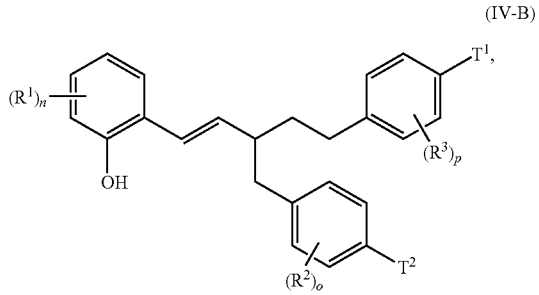

in which $R^1$, $R^2$, $R^3$, n, o, p, $T^1$ and $T^2$ each have the meanings indicated above, and the latter are then alkylated in an inert solvent in the presence of a base with a compound of the formula (V)

in which $A^2$ has the meaning indicated above, $A^{1A}$ has the meaning indicated above for $A^1$ but is not a bond, and Q is a leaving group such as, for example, halogen, tosylate or mesylate, to give compounds of the formula (IV-C)

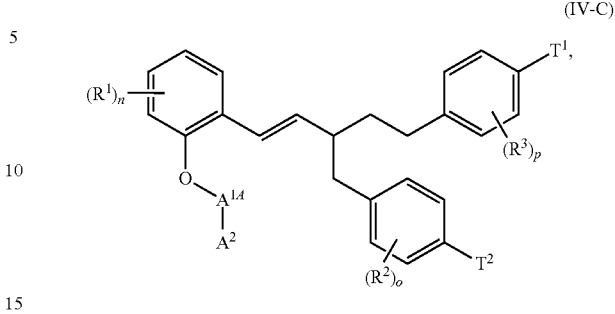

in which $A^{1A}$, $A^2$, $R^1$, $R^2$, $R^3$, n, o, p, $T^1$ and $T^2$ each have the meanings indicated above, and the resulting compounds of the formula (IV-A) or (IV-C) are then converted by hydrolysis of the ester or nitrile groups $T^1$ and $T^2$ into the dicarboxylic acids of the formula (I), and the compounds of the formula (I) are separated where appropriate by methods known to the skilled person into their enantiomers and/or diastereomers and/or reacted where appropriate with the appropriate (i) solvents and/or (ii) bases or acids to give the solvates, salts and/or solvates of the salts thereof.

Inert solvents for process steps (II)+(III-A)→(IV-A) and (II)+(III-B)→(IV-B) are for example ethers, such as diethyl ether, tetrahydrofuran, glycol dimethyl ether or diethylene glycol dimethyl ether, or hydrocarbons such as benzene, toluene, xylene, pentane, hexane, heptane, cyclohexane or petroleum fractions, or mixtures of these solvents. Tetrahydrofuran mixed with hexane is preferably used.

Bases suitable for these process steps are the bases usual for a Wittig reaction. These include in particular strong bases such as n-, sec- or tert-butyllithium, lithiumdiisopropylamide (LDA) or lithium, sodium or potassium bis(trimethylsilyl) amide. n-Butyllithium is preferred.

The reactions (II)+(III-A)→(IV-A) and (II)+(III-B)→(IV-B) are generally carried out in a temperature range from −78° C. to +20° C., preferably at −20° C. to +10° C.

Inert solvents for the process step (IV-B)+(V)→(IV-C) are for example ethers such as diethyl ether, dioxane, tetrahydrofuran, glycol dimethyl ether or diethylene glycol dimethyl ether, or other solvents such as acetonitrile, dimethylformamide, dimethyl sulphoxide, N,N'-dimethylpropylene urea (DMPU) or N-methylpyrrolidone (NMP). It is likewise possible to employ mixtures of the solvents mentioned. Acetonitrile is preferably used.

Bases suitable for this process step are in particular potassium carbonate, sodium or potassium hydride, lithiumdiisopropylamide or n-butyllithium. Potassium carbonate is preferably used.

The reaction (IV-B)+(V)→(IV-C) is generally carried out in a temperature range from +20° C. to +120° C., preferably at +50° C. to +100° C.

Hydrolysis of the ester and nitrile groups $T^1$ and $T^2$ in process steps (IV-A)→(I) and (IV-C)→(I) takes place by usual methods, by treating the esters or nitriles in inert solvents with acids or bases, and in the latter case converting the initially produced salts into the free carboxylic acids by treatment with acid. In the case of the tert-butyl esters, the ester cleavage preferably takes place with acids.

If the groups $T^1$ and $T^2$ are different, the hydrolysis can where appropriate be carried out simultaneously in a one-pot reaction or in two separate reaction steps.

Inert solvents suitable for these reactions are water or the organic solvents usual for an ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is likewise possible to employ mixtures of the solvents mentioned. In the case of a basic ester hydrolysis, mixtures of water with dioxane, tetrahydrofuran, methanol and/or ethanol are preferably employed, and in the case of nitrile hydrolysis preferably water or n-propanol. In the case of reaction with trifluoroacetic acid, preferably dichloromethane, and in the case of reaction with hydrogen chloride preferably tetrahydrofuran, diethyl ether, dioxane or water, is used.

Suitable bases are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Sodium, potassium or lithium hydroxide are particularly preferred.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof where appropriate with addition of water. Hydrogen chloride or trifluoroacetic acid in the case of the tert-butyl esters and hydrochloric acid in the case of the methyl esters are preferred.

The ester cleavage generally takes place in a temperature range from 0° C. to +100° C., preferably at +20° C. to +60° C. The nitrile hydrolysis is generally carried out in a temperature range from +50° C. to +150° C., preferably at +90° C. to +110° C.

The reactions mentioned can be carried out under atmospheric, elevated or reduced pressure (e.g. from 0.5 to 5 bar). They are generally carried out under atmospheric pressure in each case.

The aldehydes of the formula (II) can be prepared in analogy to processes disclosed in the literature, for example by a sequential dialkylation of diallyl malonate with compounds of the formulae (VI) and (VII)

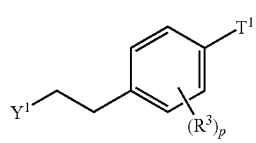

(VI)

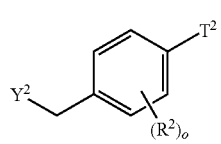

(VII)

in which $R^2$, $R^3$, o, p, $T^1$ and $T^2$ each have the meanings indicated above, and
$Y^1$ and $Y^2$ are identical or different and are a leaving group such as, for example, halogen, mesylate or tosylate, to give compounds of the formula (VIII)

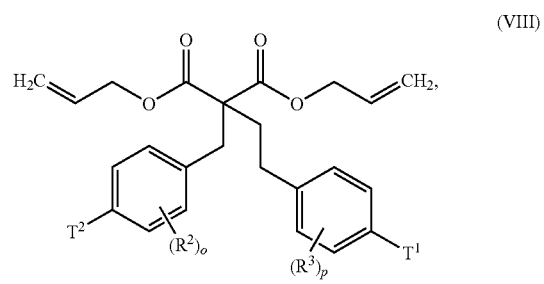

(VIII)

in which $R^2$, $R^3$, o, p, $T^1$ and $T^2$ each have the meanings indicated above,
subsequent ester cleavage to give compounds of the formula (IX)

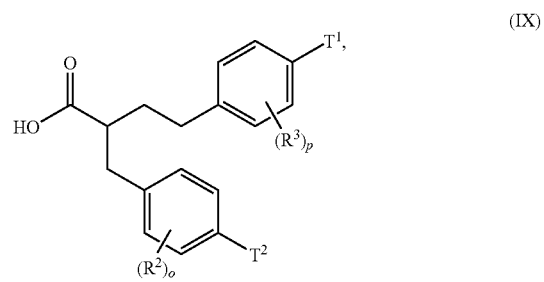

(IX)

in which $R^2$, $R^3$, o, p, $T^1$ and $T^2$ each have the meanings indicated above,
and subsequent reduction of the carboxylic acid grouping (see also reaction schemes 1 and 2 below).

The compounds of the formulae (III-A) and (III-B) can be obtained by processes usual in the literature by reaction of compounds of the formula (X-A) or (X-B)

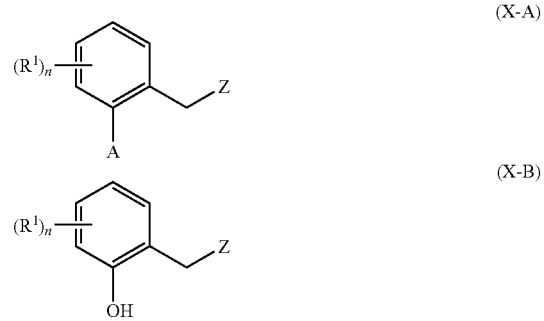

in which A, $R^1$ and n each have the meanings indicated above, and
Z is a leaving group such as, for example, halogen or tosylate, or is hydroxy,
with, for example, triphenylphosphine or (in the case of Z=OH) triphenylphosphine hydrobromide (see also reaction scheme 3 below).

The compounds of the formulae (V), (VI), (VII), (X-A) and (X-B) are commercially available, disclosed in the literature or can be prepared in analogy to processes disclosed in the literature (concerning the preparation of the compounds according to the invention overall, compare also the preparation processes described in EP 0 341 551-A1, WO 01/19355, WO 01/19776 and WO 01/19778).

Separation of the compounds according to the invention into the corresponding enantiomers and/or diastereomers can take place where appropriate, depending on expediency, even at the stage of the compounds (IV-A), (IV-B), (IV-C) or (IX), which are then reacted further in separated form in accordance with the process sequence described above. Such a fractionation of the stereoisomers can be carried out by usual methods known to the skilled person; chromatographic processes or separation via diastereomeric salts are preferably used.

Preparation of the compounds according to the invention can be illustrated by the following synthesis schemes:

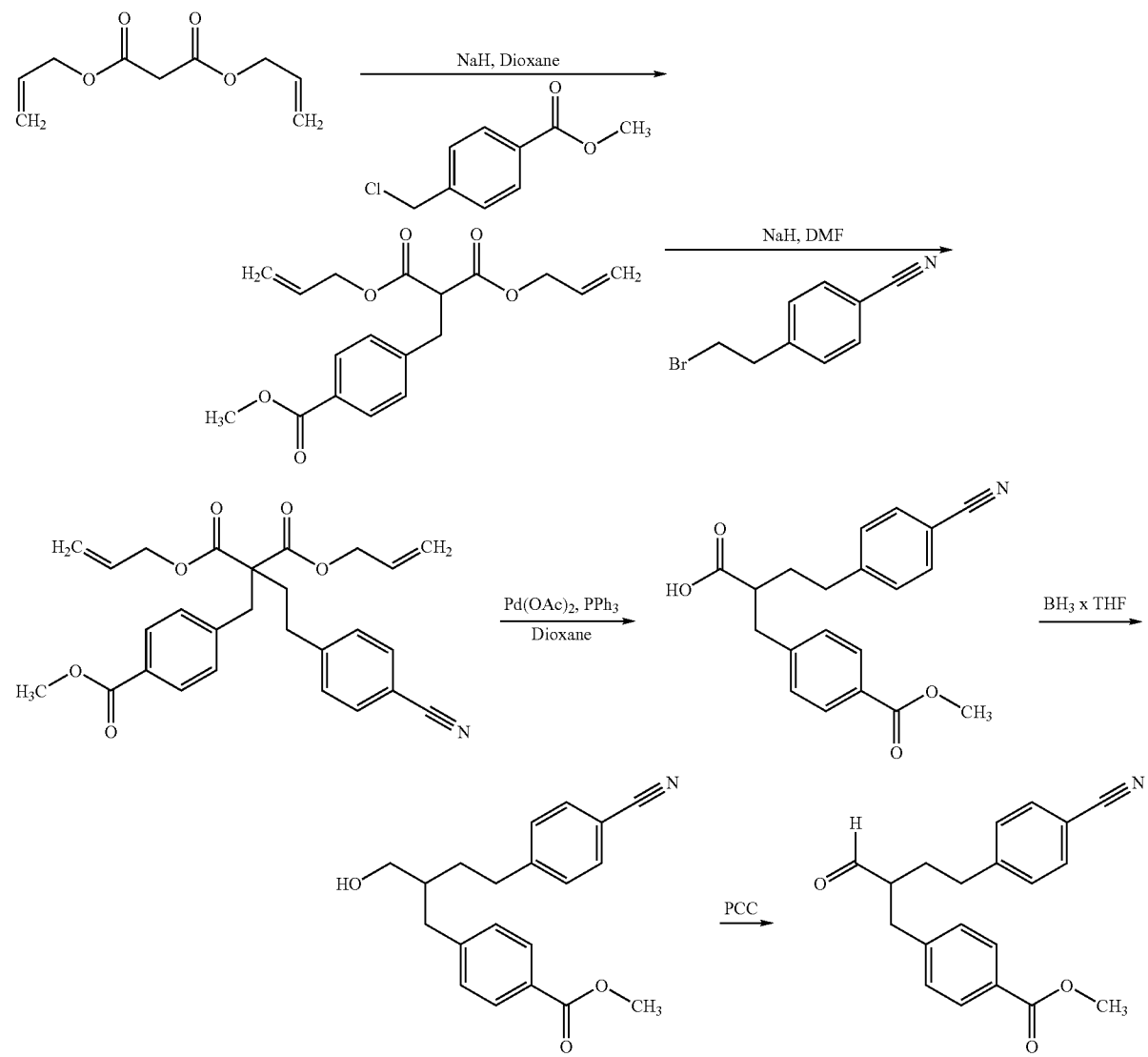

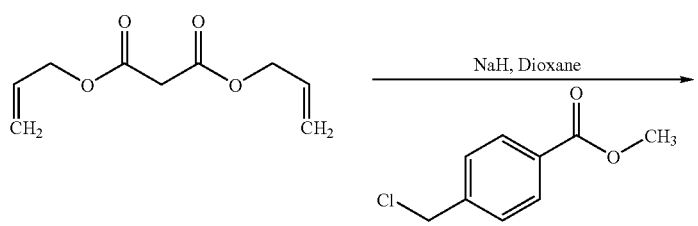

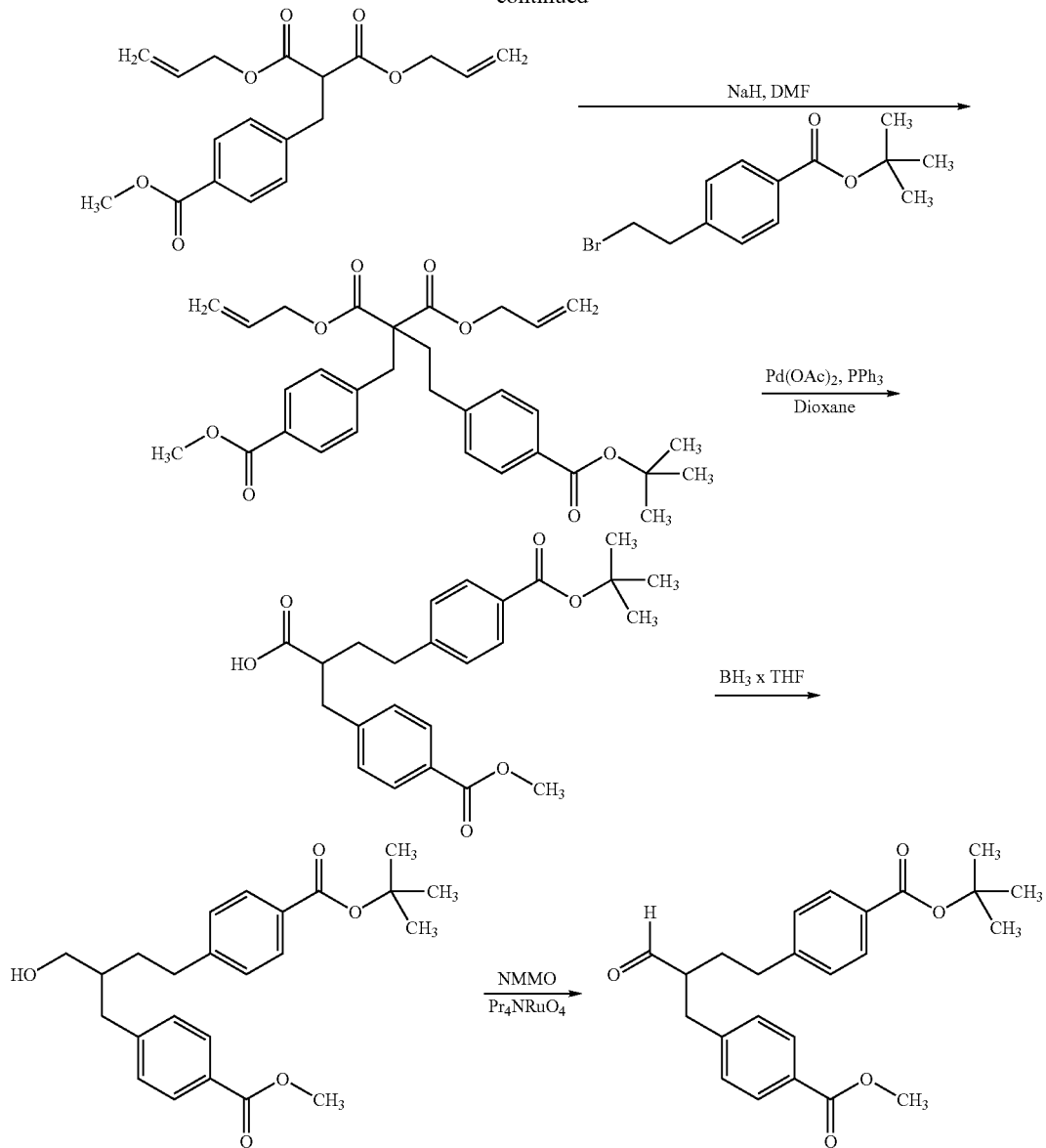
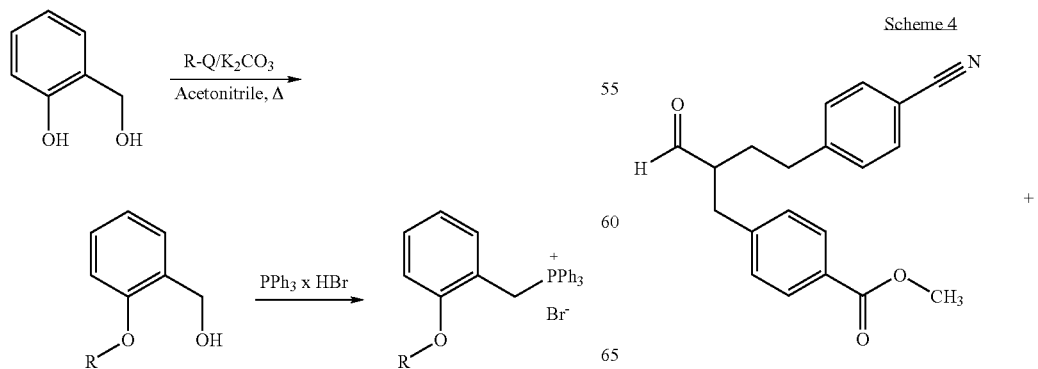

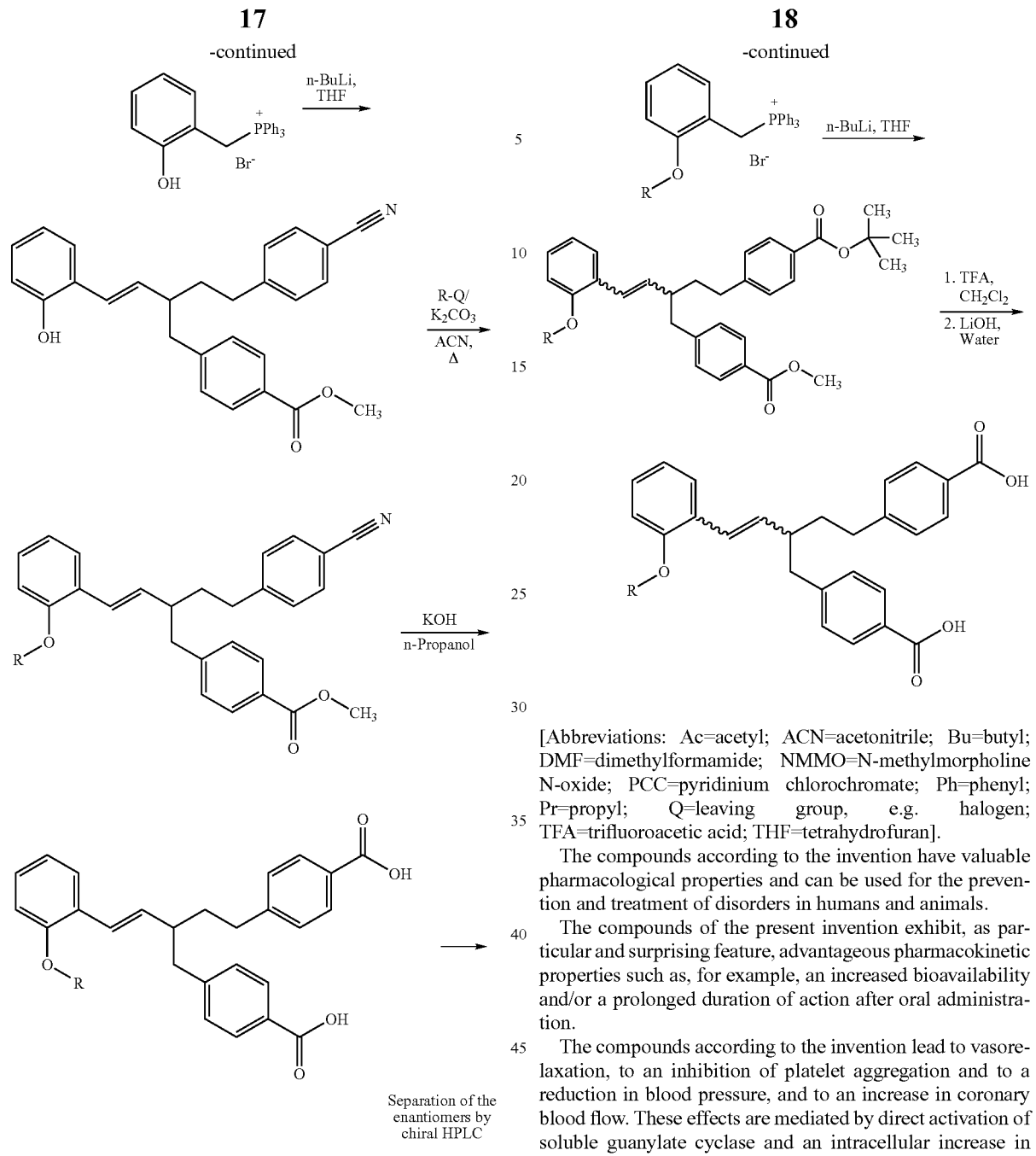

[Abbreviations: Ac=acetyl; ACN=acetonitrile; Bu=butyl; DMF=dimethylformamide; NMMO=N-methylmorpholine N-oxide; PCC=pyridinium chlorochromate; Ph=phenyl; Pr=propyl; Q=leaving group, e.g. halogen; TFA=trifluoroacetic acid; THF=tetrahydrofuran].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischaemias such as myocardial infarction, stroke, transistoric and ischaemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

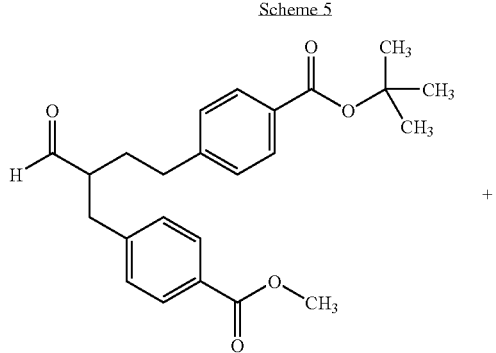

Scheme 5

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions such as stroke, cerebral ischaemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:
  organic nitrates and NO donors such as, for example, sodium nitroprusside, nitroglycerin, isosorbide mononitrate, isosorbide dinitrate, molsidomine or SIN-1, and inhaled NO;
  compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
  NO-independent but haem-dependent stimulators of guanylate cyclase, such as, in particular, the compounds described in WO 00/06568, WO 00/06569, WO 02/42301 and WO 03/095451;
  agents having antithrombotic activity, for example and preferably from the group of platelet aggregation inhibitors, of anticoagulants or of profibrinolytic substances;
  active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
  active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, CholestaGel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations abs. Absolute
aq. Aqueous
CI Chemical ionization (in MS)
DCI Direct chemical ionization (in MS)
DMF Dimethylformamide
DMSO Dimethyl sulphoxide
ee Enantiomeric excess
EI Electron impact ionization (in MS)
eq. Equivalent(s)
ESI Electrospray ionization (in MS)
Ex. Example
GC Gas chromatography
h Hour(s)
HPLC High pressure, high performance liquid chromatography
LC-MS Coupled liquid chromatography-mass spectroscopy
min Minute(s)
MS Mass spectroscopy
NMR Nuclear magnetic resonance spectroscopy
$R_f$ Retention index (in TLC)
RT Room temperature
$R_t$ Retention time (in HPLC)
THF Tetrahydrofuran
TLC Thin-layer chromatography
UV Ultraviolet spectroscopy
v/v Volume to volume ratio (of a solution)
LC/MS Methods:
Method 1 (LC-MS)

MS instrument type: Micromass ZQ; HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS)

MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS)

Instrument: Micromass Platform LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 m/min; oven: 50° C.; UV detection: 210 nm.

Method 4 (LC-MS)

Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5%

A→4.5 min 5% A; flow rate: 0.0 min 1 ml/min→2.5 min/3.0 min/4.5 min 2 ml/min; oven: 50° C.; UV detection: 208-400 nm.

Method 5 (LC-MS)

Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS)

MS instrument type: Micromass ZQ; HPLC instrument type: Waters Alliance 2795; column: Merck Chromolith SpeedROD RP-18e 100 mm×4.6 mm; eluent A: water+500 μl of 50% formic acid/l, eluent B: acetonitrile+500 μl of 50% formic acid/l; gradient: 0.0 min 10% B→7.0 min 95% B→9.0 min 95% B; flow rate: 0.0 min 1.0 ml/min→7.0 min 2.0 ml/min→9.0 min 2.0 ml/min; oven: 35° C.; UV detection: 210 mm.

Method 7 (LC-MS)

MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC-MS)

Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

GC/MS Methods:

Method 1 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).

Method 2 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 8.7 min).

HPLC Methods:

Method 1 (HPLC)

Instrument: HP 1100 with DAD detection; column: Kromasil 100 RP-18, 60 mm×2.1 mm, 3.5 μm; eluent A: 5 ml of $HClO_4$ (70%)/A of water, eluent B: acetonitrile; gradient: 0 min 2% B→0.5 min 2% B→4.5 min 90% B→9 min 90%→B 9.2 min 2% B→10 min 2% B; flow rate: 0.75 ml/min; column temperature: 30° C.; UV detection: 210 nm.

Method 2 (HPLC)

Instrument: HP 1100 with DAD detection; column: Kromasil 100 RP-18, 60 mm×2.1 mm, 3.5 μm; eluent A: 5 ml of $HClO_4$ (70%)/1 of water, eluent B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Starting Compounds and Intermediates

Example 1A (5-Bromopentyl)benzene

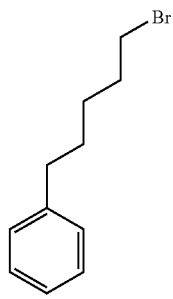 [SMILES: BrCCCCCc1ccccc1]

50 g (0.304 mol) of 5-phenylpentan-1-ol are added to a solution of 416.7 ml (1.83 mol) of 48% strength hydrobromic acid at 0° C., and the mixture is stirred at 0° C. for 30 min. The reaction solution is subsequently stirred at 10° C. for 12 hours. After reaction is complete, the mixture is cooled to room temperature and mixed with 200 ml of ethyl acetate. After extraction, the organic phase is separated off, washed with saturated sodium bicarbonate solution and dried over sodium sulphate. After filtration, the filtrate is evaporated to dryness. The resulting crude product is purified by flash chromatography on silica gel (mobile phase: cyclohexane). 59.4 g (0.26 mol, 86% yield) of a colourless liquid are obtained.

$^1$H-NMR (300 MHz, $CDCl_3$, δ/ppm): 7.32-7.22 (2H, m), 7.21-7.11 (3H, m), 3.40 (2H, t), 2.61 (2H, t), 1.97-1.81 (2H, m), 1.72-1.58 (2H, m), 1.56-1.39 (2H, m).

MS (CI): m/z=226 ($M^+$).

Example 2A

[4-(2-Bromoethyl)phenyl]methanol

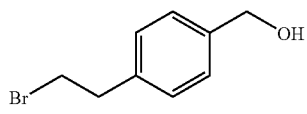 [SMILES: OCc1ccc(CCBr)cc1]

13.10 ml (13.10 mmol) of 1 M borane-THF complex are added dropwise to a solution of 2 g (8.73 mmol) of 4-(2-bromoethyl)benzoic acid in 50 ml of dry THF at −10° C. After warming to room temperature, the mixture is stirred for one hour. After reaction is complete, the mixture is mixed with saturated ammonium chloride solution and taken up in ethyl acetate, and the organic phase is separated off and dried over sodium sulphate. After filtration, the solvent is removed in vacuo. 1.67 g (7.76 mmol, 79% yield) of a colourless oil are obtained and are employed without further purification in the next stage.

$^1$H-NMR (300 MHz, DMSO-$d_6$, δ/ppm): 7.33-7.28 (4H, m), 5.14 (1H, t), 4.48 (2H, d), 3.77 (2H, t), 3.11 (2H, t).

MS (DCI, $NH_3$): m/z=232 ($M+NH_4^+$).

Example 3A

4-(2-Bromoethyl)benzaldehyde

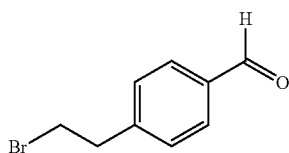 [SMILES: O=Cc1ccc(CCBr)cc1]

Process 1:

240.5 mg (1.12 mmol) of pyridinium chlorochromate (PCC) are added to a solution of 200 mg (0.93 mmol) of [4-(2-bromoethyl)phenyl]methanol in 20 ml of dichloromethane, and the mixture is stirred at room temperature for 3 hours. The reaction solution is then mixed with about 2 g of silica gel and evaporated to dryness. The resulting residue is purified by flash chromatography on silica gel (mobile phase: cyclohexane/ethyl acetate 4:1). 183 mg (0.85 mmol, 82% yield) of a colourless solid are obtained.

Process 2:

42.26 ml (0.385 mmol) of titanium tetrachloride are added over the course of 10 min to a solution of 44.4 g (0.38 mol) of dichloromethyl methyl ether in 230 ml of dichloromethane while cooling (4-5° C.), and the mixture is stirred for 1 hour. Then 64.89 g (0.34 mol) of (2-bromoethyl)benzene, dissolved in 24 ml dichloromethane, are metered into the reaction solution at 5-7° C. over the course of 50 min. The reaction solution is then slowly warmed to room temperature and the mixture is left to stir overnight. After reaction is complete, 140 ml of water are very cautiously added dropwise over the course of 1 hour (caution: initially endothermic reaction as a result of evolution of gas, then exothermic reaction up to 30° C., cooling necessary). The reaction solution is then extracted three times with dichloromethane, and the combined organic phases are washed with 170 ml of water and neutralized with 115 ml of sodium bicarbonate solution and dried over sodium sulphate. After filtration, the solvent is removed in vacuo. The resulting residue is purified by flash chromatography on silica gel (mobile phase: dichloromethane/petroleum ether 1:2→1:1). 29.3 g (0.14 mol, 37% yield) of a colourless solid are obtained.

$^1$H-NMR (300 MHz, DMSO-d$_6$, δ/ppm): 9.99 (1H, s), 7.88 (2H, d), 7.52 (2H, d), 3.80 (2H, t), 3.24 (2H, t).

MS (EI): m/z=212 (M$^+$).

Example 4A

4-(2-Bromoethyl)benzonitrile

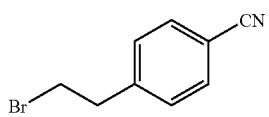

12.42 g (0.18 mol) of hydroxylamine hydrochloride are added to a solution of 29.3 g (0.14 mol) of 4-(2-bromoethyl)benzaldehyde in 112.4 ml of formic acid, and the mixture is heated under reflux for 2 hours. After slowly cooling to room temperature, 670 ml of water are added and the reaction mixture is slowly neutralized with 6 N sodium hydroxide solution while cooling. The mixture is then extracted three times with methyl tert-butyl ether. The combined organic phases are dried over magnesium sulphate and evaporated to dryness. The resulting residue is purified by flash chromatography on silica gel (mobile phase: dichloromethane). 21.3 g (0.10 mol, 74% yield) of a yellowish solid are obtained.

$^1$H-NMR (400 MHz, DMSO-d$_6$, δ/ppm): 7.80 (2H, d), 7.51 (2H, d), 3.77 (2H, t), 3.22 (2H, t).

MS (DCI, NH$_3$): m/z=227 (M+NH$_4^+$).

Example 5A

Diallyl 2-(4-methoxycarbonylbenzyl)malonate

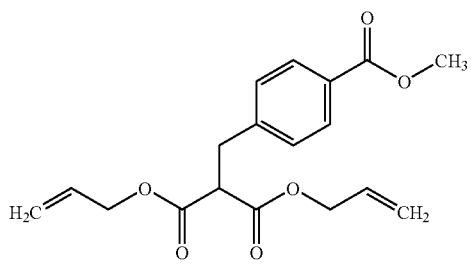 [SMILES: C=CCOC(=O)C(Cc1ccc(C(=O)OC)cc1)C(=O)OCC=C]

14.42 g (0.36 mol) of sodium hydride are added in portions to a solution of 56.7 g (0.3 mol) of diallyl malonate in 375 ml of dioxane and 75 ml of THF at 0° C. (caution: evolution of hydrogen). After warming to room temperature, the mixture is stirred at 40° C. for 1 hour. Then 111.88 g (0.6 mol) of methyl 4-chloromethylbenzoate, dissolved in 375 ml of dioxane, are slowly added dropwise at 40° C., and the reaction solution is then stirred at 110° C. (bath temperature) overnight. After cooling to room temperature, the reaction mixture is added to 1200 ml of water. Care must be taken during this that the pH is <7 (if necessary, a few ml of 1 M hydrochloric acid are metered in until the pH is about 2). The mixture is then extracted three times with ethyl acetate, and the combined organic phases are washed with saturated sodium chloride solution and dried over sodium sulphate. After filtration, the solvent is evaporated in vacuo to dryness. The resulting crude product is purified by flash chromatography on 3 kg of silica gel (mobile phase: petroleum ether/ethyl acetate 10:1). 85.4 g (0.26 mol, 85% yield) of a colourless solid are obtained.

$^1$H-NMR (300 MHz, CDCl$_3$, δ/ppm): 7.96 (2H, d), 7.29 (2H, d), 5.91-5.74 (2H, m), 5.32-5.17 (4H, m), 4.59 (4H, d), 3.93 (3H, s), 3.74 (1H, t), 3.31 (2H, d).

MS (DCI, NH$_3$): m/z=349 (M+NH$_4^+$).

Example 6A

Diallyl 2-[2-(4-cyanophenyl)ethyl]-2-(4-methoxycarbonylbenzyl)malonate

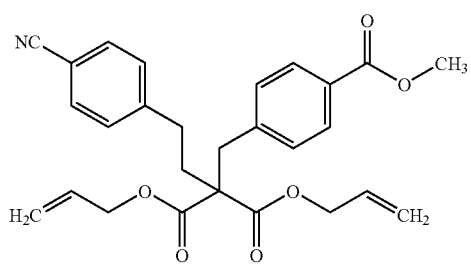

6.70 g (0.17 mol) of sodium hydride are added in portions to a solution of 55.71 g (0.17 mol) of diallyl 2-(4-methoxycarbonylbenzyl)malonate in 34 ml of DMF at 0° C. The reaction solution is then allowed to reach room temperature and is stirred for 1 hour. The reaction solution is then cooled to 0° C. again, 42.98 g (0.20 mol) of 4-(2-bromoethyl)benzonitrile in 21 ml of DMF are added, and the mixture is stirred at 0° C. for 30 min. The mixture is then stirred at room temperature overnight. Water is added dropwise to the reaction mixture, which is then extracted three times with ethyl acetate, and the combined organic phases are washed with saturated brine and dried over sodium sulphate. After filtration, the solvent is evaporated in vacuo to dryness. The resulting crude product is purified by flash chromatography on 3 kg of silica gel (mobile phase: petroleum ether/ethyl acetate 3:1). 36 g (78 mmol, 46% yield) of a colourless solid are obtained.

$^1$H-NMR (300 MHz, CDCl$_3$, δ/ppm): 7.95 (2H, d), 7.55 (2H, d), 7.21 (4H, t), 5.97-5.69 (2H, m), 5.40-5.23 (4H, m), 4.62 (4H, d), 3.92 (3H, s), 3.40 (2H, s), 2.72-2.61 (2H, m), 2.13-2.01 (2H, m).

MS (DCI, NH$_3$): m/z=479 (M+NH$_4$$^+$).

Example 7A

Methyl 4-[2-carboxy-4-(4-cyanophenyl)butyl]benzoate

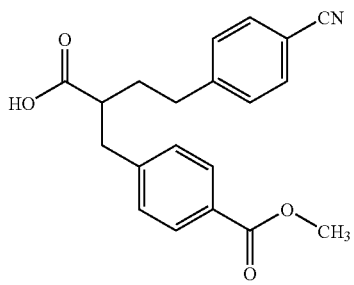 [SMILES: COC(=O)c1ccc(CC(CCc2ccc(C#N)cc2)C(=O)O)cc1]

A solution of 41.8 ml (0.3 mol) of triethylamine and 8.6 ml (0.23 mol) of formic acid in 500 ml of dioxane is added to a solution of 43.5 g (0.09 mol) of diallyl 2-[2-(4-cyanophenyl)ethyl]-2-(4-methoxycarbonylbenzyl)malonate, 1.67 g (0.01 mol) of triphenylphosphine and 410 mg of palladium acetate in 505 ml of dioxane at room temperature. The reaction mixture is then stirred at 10° C. for 2 hours. After conversion is complete, the reaction solution is cooled and the solvent is removed in vacuo. The resulting residue is purified by flash chromatography on silica gel (mobile phase: dichloromethane/methanol 50:1). 25 g (74 mmol, 82% yield) of a colourless solid are obtained.

$^1$H-NMR (400 MHz, DMSO-d$_6$, δ/ppm): 12.55-12.24 (1H, broad), 7.86 (2H, d), 7.72 (2H, d), 7.38 (2H, d), 7.32 (2H, d), 3.84 (3H, s), 2.99-2.81 (2H, m), 2.78-2.55 (3H, m), 1.90-1.67 (2H, m).

MS (ESI): m/z=338 (M+H$^+$).

Example 8A

Methyl 4-[4-(4-cyanophenyl)-2-hydroxymethylbutyl]benzoate

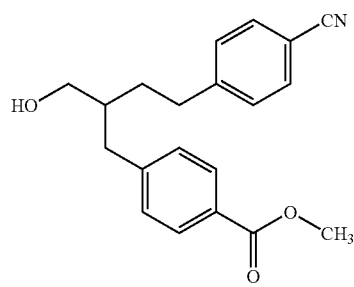 [SMILES: COC(=O)c1ccc(CC(CO)CCc2ccc(C#N)cc2)cc1]

20.6 ml (20.6 mmol) of a 1 M borane-THF complex solution are added dropwise to a solution of 4.2 g (12.98 mmol) of methyl 4-[2-carboxy-4-(4-cyanophenyl)butyl]benzoate in 40 ml of THF at −15° C., and the reaction mixture is stirred at this temperature for 3 hours. Then a further 10 ml (10 mmol) of 1 M borane-THF complex solution are added dropwise, and the mixture is stirred at −15° C. for a further 30 min. After reaction is complete, saturated sodium bicarbonate solution is added to the reaction mixture, and the solvent is evaporated to dryness. The residue is taken up in dichloromethane, dried over sodium sulphate and again freed of solvent. The resulting crude product is purified by flash chromatography on 150 g of silica gel (mobile phase: ethyl acetate/petroleum ether 1:1). 3.1 g (90% purity, 83% yield) of a colourless solid are obtained.

$^1$H-NMR (300 MHz, DMSO d$_6$, δ/ppm): 7.88 (2H, d), 7.71 (2H, d), 7.46 (4H, t), 4.54 (1H, t), 3.83 (3H, s), 3.41 (2H, t), 2.80-2.55 (4H, m), 1.79-1.39 (3H, m).

MS (ESI): m/z=324 (M+H$^+$).

Example 9A

Methyl 4-[4-(4-cyanophenyl)-2-formylbutyl]benzoate

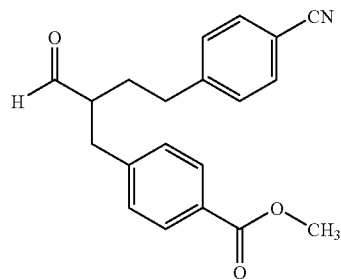 [SMILES: COC(=O)c1ccc(CC(C=O)CCc2ccc(C#N)cc2)cc1]

4.56 g (21.15 mmol) of pyridinium chlorochromate (PCC) are added to a solution of 5.7 g (17.63 mmol) of methyl 4-[4-(4-cyanophenyl)-2-hydroxymethylbutyl]benzoate in 250 ml of dichloromethane, and the mixture is stirred at room temperature for 5 hours. After conversion is complete, about 10 g of silica gel are added and the solvent is removed to dryness in vacuo. The residue is purified by flash chromatography on silica gel (mobile phase: cyclohexane/ethyl acetate 10:1→4:1). 4.16 g (12.94 mmol, 73% yield) of a colourless solid are obtained.

$^1$H-NMR (300 MHz, DMSO-$d_6$, δ/ppm): 9.68 (1H, s), 7.88 (2H, d), 7.73 (2H, d), 7.47 (4H, dd), 3.86 (3H, s), 3.14-3.02 (1H, m), 2.92-2.80 (1H, m), 2.78-2.54 (3H, m), 1.98-1.81 (1H, m), 1.76-1.60 (1H, m).

MS (DCI, NH$_3$): m/z=339 (M+NH$_4^+$).

Example 10A

Methyl E-4-[2-[2-(4-cyanophenyl)ethyl]-4-(2-hydroxyphenyl)but-3-enyl]benzoate

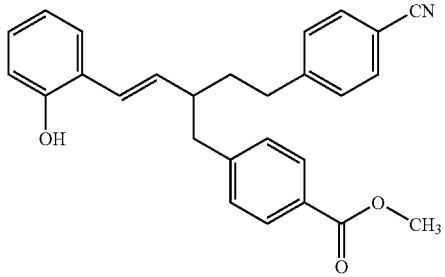

5.9 ml (9.45 mmol) of a 1.6 M solution of n-butyllithium in hexane are slowly added dropwise to a solution of 1820 mg (4.05 mmol) of (2-hydroxybenzyl)triphenylphosphonium bromide in 10 ml of THF at 0° C. Then, at this temperature, 1085 mg (3.38 mmol) of methyl 4-[4-(4-cyanophenyl)-2-formylbutyl]benzoate in 10 ml of THF are slowly metered in. After warming to room temperature, the reaction solution is stirred for 12 hours and, after addition of a little water, evaporated to dryness. The residue is taken up in ethyl acetate, washed with water and saturated sodium chloride solution and dried over sodium sulphate. After filtration, the solvent is evaporated to dryness. The resulting crude product is purified by flash chromatography on silica gel (mobile phase: cyclohexane/ethyl acetate 4:1→2:1). 1150 mg (2.79 mmol, 83% yield) of a colourless solid are obtained.

$^1$H-NMR (300 MHz, DMSO-$d_6$, δ/ppm): 9.39 (1H, s), 7.82 (2H, d), 7.60 (2H, d), 7.41-7.27 (5H, m), 7.01 (1H, t), 6.81-6.68 (2H, m), 6.45 (1H, d), 6.13-5.99 (1H, m), 3.81 (3H, s), 2.92-2.58 (5H, m), 1.86-1.56 (2H, m).

MS (DCI, NH$_3$): m/z=429 (M+NH$_4^+$).

Example 11A

Methyl 4-{(3E)$_4$-{2-[(4-tert-butylbenzyl)oxy]phenyl}-2-[2-(4-cyanophenyl)ethyl]but-3-en 1-yl}benzoate

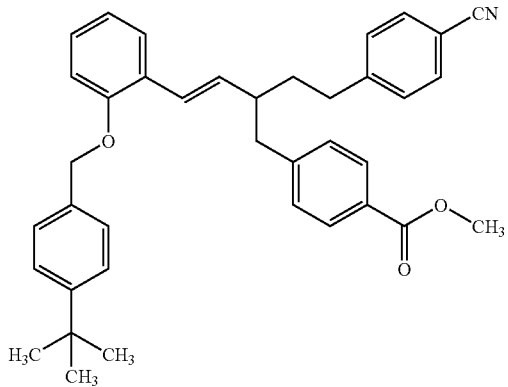 [SMILES: COC(=O)c1ccc(CC(/C=C/c2ccccc2OCc2ccc(C(C)(C)C)cc2)CCc2ccc(C#N)cc2)cc1]

2.20 g (9.71 mmol) of 4-(tert-butyl)benzyl bromide and 2.02 g (14.59 mmol) of anhydrous potassium carbonate are added to a solution of 2 g (3.6 mmol) of methyl E4-[2-[2-(4-cyanophenyl)ethyl]-4-(2-hydroxyphenyl)but-3-enyl]benzoate in 8 ml of dry acetonitrile, and the mixture is heated under reflux for 12 hours. The mixture is then filtered and the filtrate is evaporated to dryness. The residue is purified by chromatography on silica gel (mobile phase: cyclohexane/ethyl acetate 10:1). 1.9 g (3.30 mmol, 97% purity, 92% yield) of an oil are isolated.

$^1$H-NMR (400 MHz, CDCl$_3$, δ/ppm): 7.94-7.89 (2H, m), 7.49-7.30 (7H, m), 7.21-7.12 (5H, m), 6.97-6.90 (2H, m), 6.68-6.62 (1H, m), 5.06-5.02 (2H, m), 3.89 (3H, s), 2.83-2.69 (3H, m), 2.65-2.39 (2H, m), 1.86-1.59 (2H, m), 1.33 (9H, s).

LC-MS (method 2): R$_t$=3.37 min; m/z=557 (M$^+$).

Example 12A

Methyl 4-((3E)-2-[2-(4-cyanophenyl)ethyl]-4-{2-[(5-phenylpentyl)oxy]phenyl}but-3-en-1-yl)benzoate

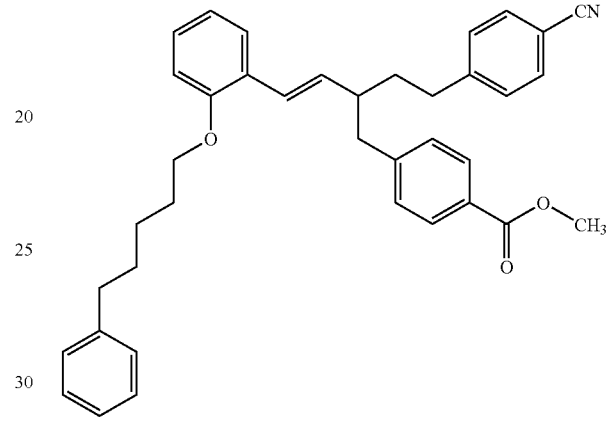

464.2 mg (2.04 mmol) of (5-bromopentyl)benzene and 353.05 mg (2.55 mmol) of potassium carbonate are added to a solution of 700.8 mg (1.7 mmol) of methyl 4-[(3E)-2-[2-(4-cyanophenyl)ethyl]-4-(2-hydroxyphenyl)but-3-en-1-yl] benzoate in 65 ml of acetonitrile, and the mixture is stirred under reflux for 12 hours. After cooling, the potassium carbonate is filtered off and the filtrate is evaporated. The resulting residue is purified by flash chromatography on silica gel (mobile phase: cyclohexane/ethyl acetate 7:3). 945 mg (1.7 mmol, 99.5% yield) are obtained.

LC-MS (method 2): R$_t$=3.37 min; MS (ESIpos): m/z=575 (M+NH$_4^+$).

Example 13A

Methyl 4-[(3E)-2-[2-(4-cyanophenyl)ethyl]-4-(2-{[4-(2-phenylethyl)benzyl]oxy}phenyl)but-3-en-1-yl]benzoate

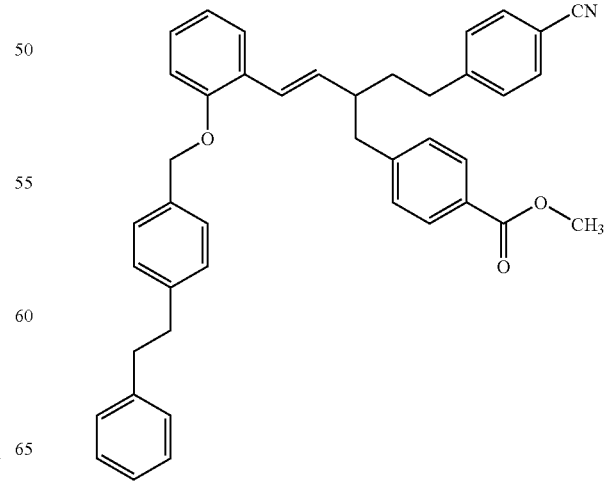

460 mg (2 mmol) of 1-(chloromethyl)-4-(2-phenylethyl) benzene [preparation according to M. Carrara et al., *Arzneim. Forsch.* 47 (7), 803-809 (1997)] and 414 mg (3 mmol) of anhydrous potassium carbonate are added to a solution of 411 mg (1 mmol) of methyl 4-[(3E)-2-[2-(4-cyanophenyl)ethyl]-4-(2-hydroxyphenyl)but-3-en-1-yl]benzoate in 10 ml of dry acetonitrile, and the mixture is heated under reflux for 12 hours. The mixture is then evaporated to dryness. The residue is taken up in ethyl acetate, washed with water and with saturated sodium chloride solution and dried over sodium sulphate. After filtration, the organic phase is evaporated and the resulting crude product is purified by preparative HPLC. 431 mg (0.7 mmol, 65% yield) of a solid are obtained.

$^1$H-NMR (400 MHz, CDCl$_3$, δ/ppm): 7.91 (2H, d), 7.43 (2H, d), 7.38 (1H, d), 7.34-7.27 (4H, m), 7.22-7.1 (10H, m), 7.95 (2H, t), 6.63 (1H, d), 6.0 (1H, dd), 5.04 (2H, s), 3.89 (3H, s), 3.0-2.88 (4H, m), 2.8-2.7 (3H, m), 2.63-2.5 (1H, m), 2.5-2.4 (1H, m), 1.86-1.73 (1H, m), 1.7-1.59 (1H, m).

Example 14A

Ethyl 4'-trifluoromethylbiphenyl-4-carboxylate

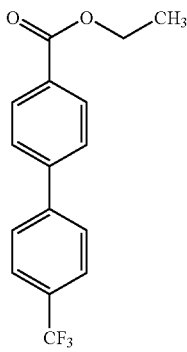

7 g (30.56 mmol) of ethyl 4-bromobenzoate are dissolved in 60 ml of 1,2-dimethoxyethane and, under argon, 6.96 g (36.67 mmol) of 4-trifluoromethylphenylboronic acid, 271 mg of bis(triphenylphosphine)palladium(II) chloride and 40.7 ml of a 2 M aqueous sodium carbonate solution are added. The reaction mixture is then stirred under reflux for 12 hours. The mixture is then cooled, filtered through 1 g of Extrelute, washed with dichloromethane and concentrated. The resulting crude product is purified by flash chromatography on silica gel (mobile phase: cyclohexane/dichloromethane 2:1). 6.31 g (21.4 mmol, 70% yield) of a colourless solid are obtained.

$^1$H-NMR (300 MHz, CDCl$_3$, δ/ppm): 8.17 (2H, d), 7.72 (4H, s), 7.67 (2H, d), 4.41 (2H, q), 1.43 (3H, t).

MS (EI): m/z=294 (M$^+$).

Example 15A (4'-Trifluoromethylbiphenyl-4-yl)methanol

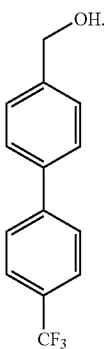

12.73 ml (12.73 mmol) of a 1 M solution of lithium aluminium hydride in THF are added dropwise to a solution of 6.24 g (21.21 mmol) of ethyl 4'-trifluoromethylbiphenyl-4-carboxylate in 60 ml of dry THF at 0° C. After reaction is complete, saturated ammonium chloride solution is added to the mixture, which is taken up in ethyl acetate, and the organic phase is separated off and dried over sodium sulphate. After filtration, the solvent is removed in vacuo. The resulting crude product is purified by flash chromatography on silica gel (mobile phase: cyclohexane/ethyl acetate 5:1). 5.1 g (20.21 mmol, 95% yield) of a colourless solid are obtained.

$^1$H-NMR (300 MHz, DMSO-d$_6$, δ/ppm): 7.88 (2H, d), 7.82 (2H, d), 7.71 (2H, d), 7.46 (2H, d), 5.23 (1H, t), 4.58 (2H, d).

MS (EI): m/z=252 (M$^+$).

Example 16A

4-Chloromethyl-4'-trifluoromethylbiphenyl

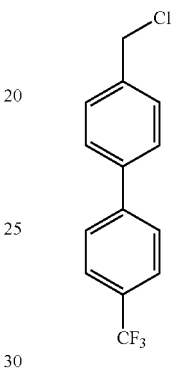

2.89 ml (39.65 mmol) of thionyl chloride dissolved in 10 ml of chloroform are added to a solution of 5.0 g (19.82 mmol) of (4'-trifluoromethylbiphenyl-4-yl)methanol in 40 ml of chloroform, and the mixture is stirred at room temperature for 12 hours. After reaction is complete, the reaction mixture is evaporated to dryness, and the residue is taken up in ethyl acetate and washed with saturated sodium carbonate solution. The organic phase is separated off, dried over sodium sulphate and evaporated after filtration. The resulting crude product is purified by flash chromatography on silica gel (mobile phase: cyclohexane/ethyl acetate 9:1). 5.26 g (19.43 mmol, 98% yield) of a colourless solid are obtained.

$^1$H-NMR (300 MHz, DMSO-d$_6$, δ/ppm): 7.91 (2H, d), 7.82 (2H, d), 7.78 (2H, d), 7.58 (2H, d), 4.83 (2H, s).

MS (EI): m/z=270 (M$^+$).

Example 17A

[2-(4'-Trifluoromethylbiphenyl-4-yl-methoxy)phenyl]methanol

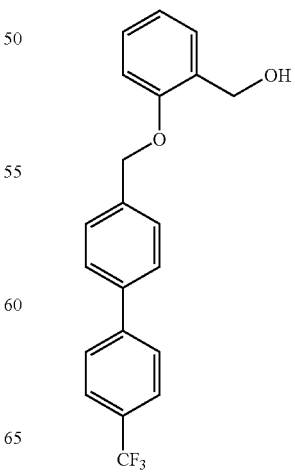

10 g (36.94 mmol) of 4-chloromethyl-4'-trifluoromethyl-biphenyl and 6.13 g (44.33 mmol) of anhydrous potassium carbonate are added to a solution of 4.59 g (36.94 mmol) of 2-hydroxybenzyl alcohol in 200 ml of dry acetonitrile, and the mixture is heated under reflux for 12 hours. The mixture is then evaporated to dryness. The residue is taken up in ethyl acetate, washed with water and with saturated brine and dried over sodium sulphate. The organic phase is evaporated and the crude product is purified by flash chromatography on silica gel (mobile phase: cyclohexane/ethyl acetate 5:1). 11.8 g (32.92 mmol, 89% yield) of a solid are obtained.

$^1$H-NMR (300 MHz, DMSO-$d_6$, δ/ppm): 7.92 (2H, d), 7.87-7.72 (4H, m), 7.60 (2H, d), 7.41 (1H, d), 7.21 (1H, t), 7.03 (1H, d), 6.96 (1H, t), 5.20 (2H, s), 5.03 (1H, t), 4.58 (2H, d).

MS (DCI, $NH_3$): m/z=376 ($M+NH_4^+$).

Example 18A

Triphenyl-[2-(4'-trifluoromethylbiphenyl-4-yl-methoxy)benzyl]phosphonium bromide

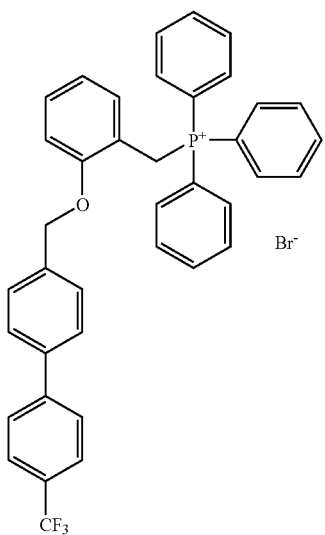 [SMILES: FC(F)(F)c1ccc(-c2ccc(COc3ccccc3C[P+](c3ccccc3)(c3ccccc3)c3ccccc3)cc2)cc1 ; [Br-]]

A solution of 11.7 g (32.65 mmol) of [2-(4'-trifluoromethylbiphenyl-4-ylmethoxy)phenyl]methanol in 100 ml of acetonitrile is mixed with 10.64 g (31.02 mmol) of triphenylphosphonium hydrobromide and heated under reflux for 3 hours. The reaction solution is then evaporated to dryness, and the resulting oil is taken up and triturated in diethyl ether. The product crystallizes as a white solid. After filtration, the solid is dried in a drying oven at 50° C. overnight. 20.5 g (30 mmol, 92% yield) of crystalline product are obtained.

$^1$H-NMR (300 MHz, DMSO-$d_4$, δ/ppm): 7.99-7.79 (8H, m), 7.78-7.50 (12H, m), 7.32 (4H, d), 7.08 (1H, d), 6.97 (1H, d), 6.86 (1H, t), 5.03 (2H, d), 4.70 (2H, s).

Example 19A tert-Butyl 4-methylbenzoate

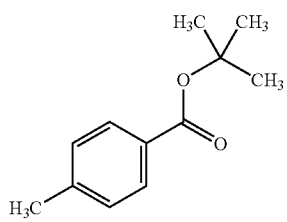

8.55 ml (64.69 mmol) of 4-toluoyl chloride are added dropwise to 10.52 ml (109.96 mmol) of tert-butanol and 10.46 ml (129.37 mmol) of pyridine while cooling in ice. The mixture is stirred at room temperature for 12 hours. After reaction is complete, water is added and the mixture is extracted with ethyl acetate. The organic phase is washed successively with sodium bicarbonate solution, water and sodium chloride solution, dried over sodium sulphate and evaporated. The resulting residue is purified by flash chromatography on silica gel (mobile phase: cyclohexane/ethyl acetate 50:1). 7.76 g (40.36 mmol, 62% yield) of the title compound are obtained as a colourless oil.

$^1$H-NMR (300 MHz, $CDCl_3$, δ/ppm): 7.88 (2H, d), 7.2 (2H, d), 2.4 (3H, s), 1.59 (9H, s).

Example 20A tert-Butyl 4-(2-methoxy-2-oxoethyl)benzoate

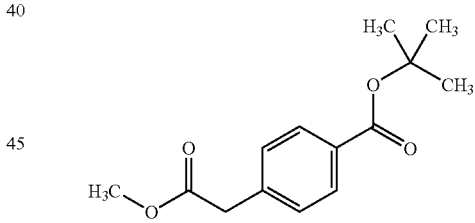

With exclusion of oxygen, 11.79 ml (84.11 mmol) of diisopropylamine are introduced into 40 ml of THF and cooled to −78° C., and 52.57 ml (84.11 mmol) of n-butyllithium (1.6 M solution in hexane) are slowly added dropwise. The mixture is stirred at −78° C. for 10 minutes and then 10.17 ml (84.11 mmol) of 1,3-dimethyltetrahydro-2-(1H)-pyrimidinone are added. After 15 minutes, 7.7 g (40.05 mmol) of tert-butyl 4-methylbenzoate, dissolved in 40 ml of THF, are added dropwise, and the mixture is stirred for a further 15 minutes. 3.25 ml (42.05 mmol) of methyl chloroformate are separately dissolved in 20 ml of THF, cooled to −70° C. and then rapidly added to the reaction mixture. After a further 15 minutes, ammonium chloride solution is added to the reaction mixture, which is warmed to room temperature. It is diluted with water, and the phases are separated. The aqueous phase is extracted twice with diethyl ether. The combined organic phases are washed with saturated sodium chloride solution, dried over sodium sulphate and evaporated. The resulting residue is purified by flash chromatography on silica gel (mobile phase: cyclohexane/ethyl acetate 50:1). 4.2 g (16.78 mmol, 40% yield) of the title compound are obtained as a colourless oil.

$^1$H-NMR (300 MHz, CDCl$_3$, δ/ppm): 7.95 (2H, d), 7.32 (2H, d), 3.7 (3H, s), 3.68 (2H, s), 1.59 (9H, s).

Example 21A

[4-(tert-Butoxycarbonyl)phenyl]acetic acid

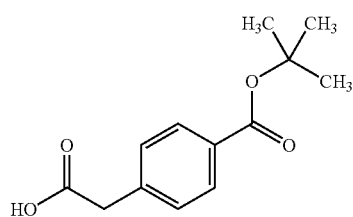 [SMILES: CC(C)(C)OC(=O)c1ccc(CC(=O)O)cc1]

A solution of 4.2 g (16.78 mmol) of tert-butyl 4-(2-methoxy-2-oxoethyl)benzoate in 50 ml of water and 50 ml of THF is mixed with 0.8 g (33.6 mmol) of lithium hydroxide and stirred at room temperature for 1 hour. The phases are separated and the aqueous phase is adjusted to pH 3 with 2 M hydrochloric acid. It is extracted with ethyl acetate. The organic phase is then washed with sodium chloride solution, dried over sodium sulphate and evaporated. 3.6 g (15.2 mmol, 87% yield) of the title compound are obtained.

$^1$H-NMR (400 MHz, DMSO-d$_6$, δ/ppm): 12.45 (1H, broad), 7.85 (2H, d), 7.89 (2H, d), 3.66 (2H, s), 1.54 (9H, s).

Example 22A tert-Butyl 4-(2-hydroxyethyl)benzoate

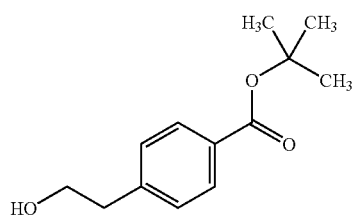 [SMILES: CC(C)(C)OC(=O)c1ccc(CCO)cc1]

30.47 ml (30.47 mmol) of 1 M borane-THF complex solution are slowly added dropwise to a solution of 3.6 g (15.24 mmol) of [4-(tert-butoxycarbonyl)phenyl]acetic acid in 100 ml of THF at −10° C. with exclusion of oxygen. The mixture is stirred at 0° C. for 4 hours. Subsequently, ammonium chloride solution is added and the mixture is extracted with diethyl ether. The combined organic phases are washed with sodium chloride solution, dried over sodium sulphate and evaporated. 3.2 g (14.4 mmol, 92% yield) of the title compound are obtained.

$^1$H-NMR (400 MHz, DMSO-d$_6$, δ/ppm): 7.81 (2H, d), 7.34 (2H, d), 4.69 (1H, t), 3.62 (2H, q).

Example 23A tert-Butyl 4-(2-bromoethyl)benzoate

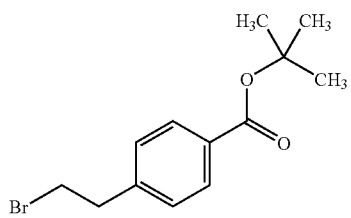 [SMILES: CC(C)(C)OC(=O)c1ccc(CCBr)cc1]

7.16 g (21.59 mmol) of tetrabromomethane and 5.66 g (21.59 mmol) of triphenylphosphine are dissolved in 70 ml of THF with exclusion of oxygen and stirred at room temperature for 30 minutes. Then 3.2 g (14.4 mmol) of tert-butyl 4-(2-hydroxyethyl)benzoate, dissolved in 30 ml of THF, are added dropwise, and the reaction mixture is stirred at room temperature for 12 hours. After conversion is complete, the mixture is evaporated to dryness and the resulting residue is purified by flash chromatography on silica gel (mobile phase: cyclohexane/ethyl acetate 10:1). 3.9 g (13.7 mmol, 87% yield) of the title compound are obtained as a colourless oil.

$^1$H-NMR (300 MHz, DMSO-d$_6$, δ/ppm): 7.85 (2H, d), 7.4 (2H, d), 3.76 (2H, t), 3.2 (2H, t), 1.55 (9H, s).

Example 24A

Diallyl {2-[4-(tert-butoxycarbonyl)phenyl]ethyl}[4-(methoxycarbonyl)benzyl]malonate

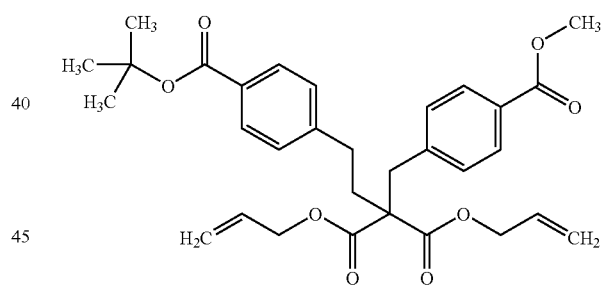

0.6 g (14.92 mmol) of sodium hydride is added in portions to a solution of 4.13 g (12.43 mmol) of diallyl 2-(4-methoxycarbonylbenzyl)malonate in 40 ml of DMF at 0° C. The reaction solution is then allowed to reach room temperature and is stirred for 1 hour. The reaction solution is then cooled again to 0° C., 3.9 g (13.68 mmol) of tert-butyl 4-(2-bromoethyl)benzoate in 10 ml of DMF are added, and the mixture is stirred at this temperature for 30 min. The mixture is then stirred at room temperature overnight. The reaction mixture is added to ice-water and extracted three times with ethyl acetate, and the combined organic phases are washed with saturated brine and dried over sodium sulphate. After filtration, the solvent is evaporated to dryness in vacuo, and the resulting crude product is purified by preparative HPLC. 933 mg (1.7 mmol, 14% yield) of a colourless solid are obtained.

$^1$H-NMR (300 MHz, CDCl$_3$, δ/ppm): 7.91 (4H, dd), 7.2 (4H, dd), 5.95-5.8 (2H, m), 5.79 (4H, dd), 4.63 (4H, d), 3.9 (3H, s), 3.4 (2H, s), 2.7-2.62 (2H, m), 2.13-2.05 (2H, m), 1.58 (9H, s).

Example 25A

4-[4-(tert-Butoxycarbonyl)phenyl]-2-[4-(methoxycarbonyl)benzyl]butanoic Acid

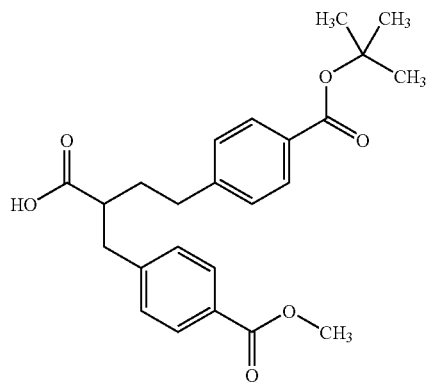 [SMILES: COC(=O)c1ccc(CC(CCc2ccc(C(=O)OC(C)(C)C)cc2)C(=O)O)cc1]

A solution of 0.79 ml (5.66 mmol) of triethylamine and 0.16 ml (4.29 mmol) of formic acid in 10 ml of dioxane is added to a solution of 920 mg (1.71 mmol) of diallyl {2-[4-(tert-butoxycarbonyl)phenyl]ethyl}[4-(methoxycarbonyl)benzyl]malonate, 31.5 mg (0.12 mmol) of triphenylphosphine and 7.7 mg (0.03 mmol) of palladium acetate in 10 ml of dioxane at room temperature. The reaction mixture is then stirred at 100° C. for 12 hours. After conversion is complete, the reaction solution is cooled and the solvent is removed in vacuo. The resulting residue is purified by flash chromatography on silica gel (mobile phase: cyclohexane/ethyl acetate 4:1→1:1). 497 mg (1.2 mmol, 61% yield) of a colourless solid are obtained.

$^1$H-NMR (400 MHz, DMSO-d$_6$, δ/ppm): 12.3 (1H, s), 7.86 (2H, d), 7.81 (2H, d), 7.32 (2H, d), 7.28 (2H, d), 3.82 (3H, s), 2.98-2.82 (2H, m), 2.74-2.56 (2H, m), 1.9-1.59 (3H, m), 1.53 (9H, s).

Example 26A tert-Butyl methyl-4,4'-[2-(hydroxymethyl)butane-1,4-diyl]dibenzoate

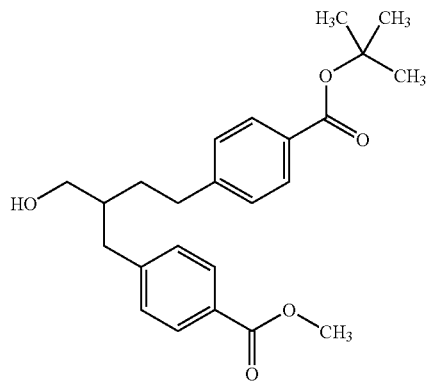 [SMILES: COC(=O)c1ccc(CC(CO)CCc2ccc(C(=O)OC(C)(C)C)cc2)cc1]

1.81 ml (1.81 mmol) of 1 M borane-THF complex solution are added dropwise to a solution of 497 mg (1.2 mmol) of 4-[4-(tert-butoxycarbonyl)phenyl]-2-[4-(methoxycarbonyl)benzyl]butanoic acid in 10 ml of THF at −15° C., and the reaction mixture is stirred at this temperature for 3 hours. After reaction is complete saturated ammonium chloride solution is added to the reaction mixture, and it is extracted with ethyl acetate. The organic phase is washed with sodium chloride solution, dried over sodium sulphate and evaporated. The resulting crude product is purified by flash chromatography on silica gel (mobile phase: cyclohexane/ethyl acetate 4:1). 403 mg (1.0 mmol, 81% yield) of a colourless solid are obtained.

$^1$H-NMR (300 MHz, DMSO-d$^6$, δ/ppm): 7.87 (2H, d), 7.78 (2H, d), 7.31 (2H, d), 7.25 (2H, d), 4.5 (1H, t), 3.84 (3H, s), 3.32 (2H, t), 2.8-2.57 (4H, m), 1.76-1.57 (3H, m), 1.53 (9H, s).

Example 27A tert-Butyl methyl-4,4'-(2-formylbutane-1,4-diyl)dibenzoate

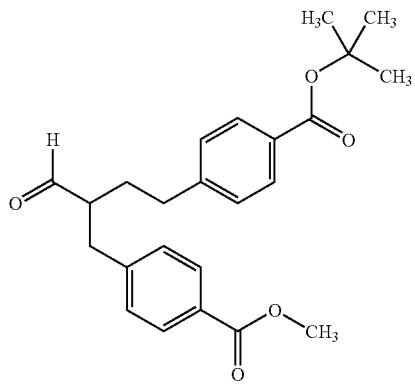 [SMILES: COC(=O)c1ccc(CC(C=O)CCc2ccc(C(=O)OC(C)(C)C)cc2)cc1]

A solution of 400 mg (1 mmol) of tert-butyl methyl-4,4'-[2-(hydroxymethyl)butane-1,4-diyl]dibenzoate in 20 ml of dichloromethane is mixed with 5 g of 4 Å molecular sieves and 176.4 mg (1.51 mmol) of N-methylmorpholine N-oxide and stirred at room temperature for 10 minutes. Subsequently, 17.6 mg (0.05 mmol) of tetrapropylammonium perruthenate are added, and the reaction mixture is stirred at room temperature for 5 hours. The molecular sieves are filtered off through kieselguhr and the filtrate is concentrated. The resulting residue is purified by flash chromatography on silica gel (mobile phase: cyclohexane/ethyl acetate 4:1). 200 mg (0.5 mmol, 50% yield) of a colourless solid are obtained and are directly reacted further.

Example 28A

Methyl 4-[(3E/Z)-2-{2-[4-(tert-butoxycarbonyl)phenyl]ethyl}-4-(2-{[4'-(trifluoromethyl)biphenyl-4-yl]methoxy}phenyl)but-3-en-1-yl]benzoate

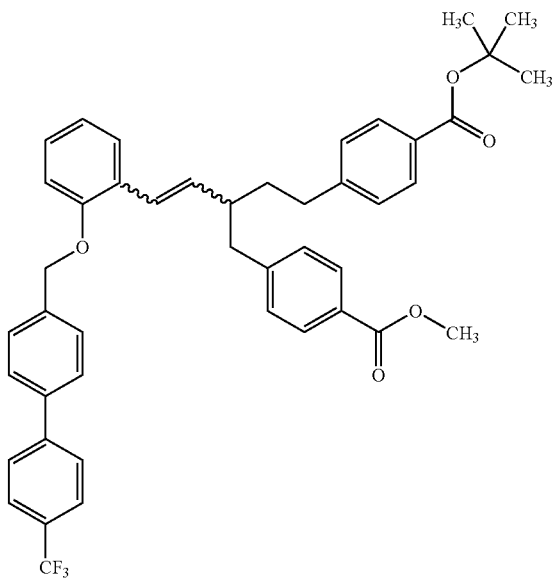 [SMILES: COC(=O)c1ccc(CC(C=Cc2ccccc2OCc2ccc(-c3ccc(C(F)(F)F)cc3)cc2)CCc2ccc(C(=O)OC(C)(C)C)cc2)cc1]

0.47 ml (0.76 mmol) of a 1.6 M solution of n-butyllithium in hexane is slowly added to a solution of 412 mg (0.61 mmol) of triphenyl-(2-{[4'-(trifluoromethyl)biphenyl-4-yl]methoxy}benzyl)phosphonium bromide in 10 ml of THF at 0° C. Then, at this temperature, 200 mg (0.5 mmol) of tert-butyl methyl-4,4'-(2-formylbutane-1,4-diyl)dibenzoate are metered in. After warming to room temperature, the reaction solution is stirred for 12 hours and, after addition of a little water, evaporated to dryness. The residue is taken up in ethyl acetate, washed with water and with saturated sodium chloride solution and dried over sodium sulphate. After filtration, the solvent is evaporated to dryness. The resulting crude product is purified by flash chromatography on silica gel (mobile phase: cyclohexane/ethyl acetate 50:1→20:1). 270 mg (0.37 mmol, 70% yield) of a white foam are obtained.

$^1$H-NMR (300 MHz, DMSO-d$_6$, δ/ppm): 7.88-7.6 (10H, m), 7.55-7.38 (2H, m), 7.32-7.15 (7H, m), 7.15-7.0 (1H, m), 6.92 (1H, t), 6.5 (1H, d), 6.12 (1H, dd), 5.15 (2H, s), 3.76 (3H, s), 2.92-2.56 (5H, m), 1.88-1.56 (2H, m), 1.5 (9H, s).

Example 29A

4-[(4E/Z)-3-[4-(Methoxycarbonyl)benzyl]-5-(2-{[4'-(trifluoromethyl)biphenyl-4-yl]methoxy}-phenyl)pent-4-en-1-yl]benzoic Acid

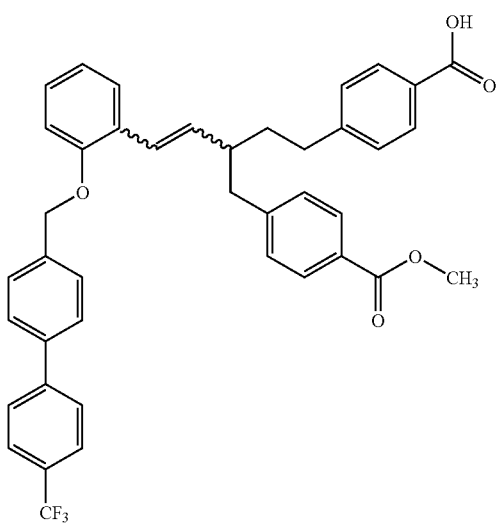 [SMILES: COC(=O)c1ccc(CC(C=Cc2ccccc2OCc2ccc(-c3ccc(C(F)(F)F)cc3)cc2)CCc2ccc(C(=O)O)cc2)cc1]

A solution of 100 mg (0.14 mmol) of methyl 4-[(3E/Z)-2-{2-[4-(tert-butoxycarbonyl)-phenyl]ethyl}-4-(2-{[4'-(trifluoromethyl)biphenyl-4-yl]methoxy}phenyl)but-3-en-1-yl]benzoate in 4 ml of dichloromethane is mixed with 1 ml (13 mmol) of trifluoroacetic acid and stirred at room temperature for 1 hour. The mixture is evaporated and the residue is partitioned between water and ethyl acetate. The organic phase is dried over sodium sulphate and evaporated. The resulting residue is purified by flash chromatography on silica gel (mobile phase: cyclohexane/ethyl acetate 4:1). 56 mg (0.08 mmol, 55% yield) of the title compound are obtained.

LC-MS (method 2): R$_t$=3.28 min; MS (ESIpos): m/z=665 (M+H)$^+$.

Example 30A

Methyl 4-{(3E)-2-[2-(4-cyanophenyl)ethyl]-4-[2-(4,4,4-trifluorobutoxy)phenyl]but-3-en-1-yl}benzoate

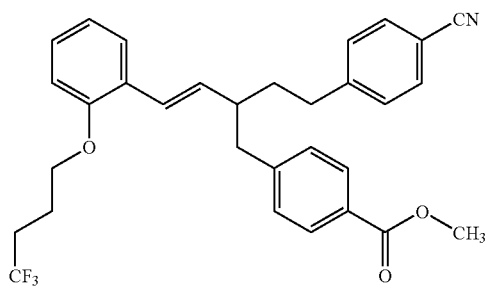

A solution of 200 mg (0.486 mmol) of methyl 4-[(3E)-2-[2-(4-cyanophenyl)ethyl]-4-(2-hydroxyphenyl)but-3-en-1-yl]benzoate in 5 ml of acetonitrile is mixed with 101 mg (0.73 mmol) of potassium carbonate and 139 mg (0.73 mmol) of 4,4,4-trifluoro-1-bromobutane and stirred under reflux for 12 h. After conversion is complete, the salts are filtered off and the mother liquor evaporated. 253 mg (0.49 mmol, 100% of theory) of the title compound are obtained.

LC-MS (method 2): R$_t$=3.21 min; MS (ESIpos): m/z=522 (M+H)$^+$.

Example 31A

Methyl 4-[(3E)-2-[2-(4-cyanophenyl)ethyl]-4-(2-methoxyphenyl)but-3-en-1-yl]benzoate

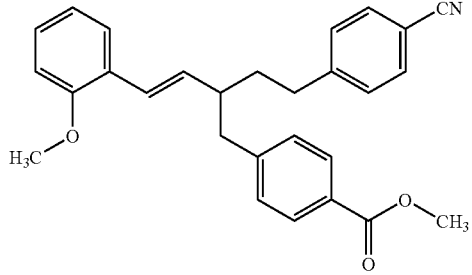 [SMILES: COC(=O)c1ccc(CC(/C=C/c2ccccc2OC)CCc2ccc(C#N)cc2)cc1]

1.9 g (4.5 mmol, 92% of theory) of the title compound are obtained by the process described in Example 30A starting from 2 g (4.9 mmol) of methyl 4-[(3E)-2-[2-(4-cyanophenyl)ethyl]-4-(2-hydroxyphenyl)but-3-en-1-yl]benzoate, 1 g (7.3 mmol) of potassium carbonate and 3.63 ml (58 mmol) of iodomethane.

MS (DCI): m/z=443 (M+NH$_4$)$^+$.

Example 32A

4-[(3E)-2-[2-(4-Cyanophenyl)ethyl]-4-(2-methoxyphenyl)but-3-en-1-yl]benzoic Acid

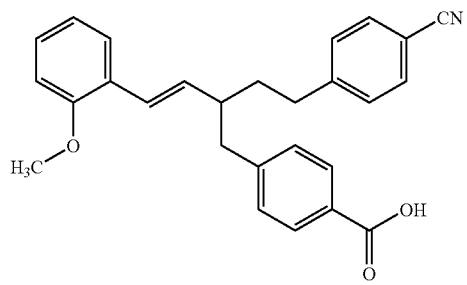 [SMILES: COc1ccccc1/C=C/C(CCc1ccc(C#N)cc1)Cc1ccc(C(=O)O)cc1]

A solution of 744 mg (1.75 mmol) of methyl 4-[(3E)-2-[2-(4-cyanophenyl)ethyl]-4-(2-methoxyphenyl)but-3-en-1-yl] benzoate in 24 ml of THF and 24 ml of water is mixed with 84 mg (3.5 mmol) of lithium hydroxide and stirred at 50° C. for 12 h. After conversion is complete, the reaction solution is diluted with diethyl ether and water, and the phases are separated. The aqueous phase is acidified with 1 M hydrochloric acid and extracted with diethyl ether. The resulting organic phase is washed with sodium chloride solution, dried over sodium sulphate and evaporated. 606 mg (1.5 mmol, 97% of theory) of the title compound are obtained.

LC-MS (method 2): $R_t$=2.68 min; MS (ESIpos): m/z=412 $(M+H)^+$.

Example 33A

Methyl 4-{(3E)-4-(2-butoxyphenyl)-2-[2-(4-cyanophenyl)ethyl]but-3-en-1-yl}benzoate

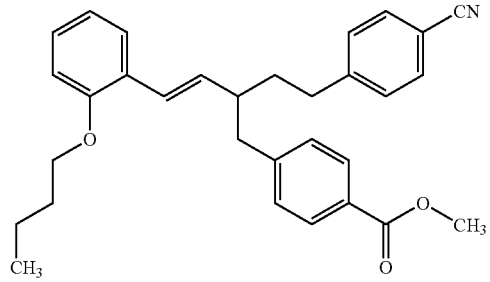 [SMILES: CCCCOc1ccccc1/C=C/C(CCc1ccc(C#N)cc1)Cc1ccc(C(=O)OC)cc1]

224 mg (0.48 mmol, 85% of theory) of the title compound are obtained by the process described in Example 30A starting from 200 mg (0.49 mmol) of methyl 4-[(3E)-2-[2-(4-cyanophenyl)ethyl]-4-(2-hydroxyphenyl)but-3-en-1-yl]benzoate, 101 mg (0.73 mmol) of potassium carbonate and 100 mg (0.73 mmol) of 1-bromobutane.

LC-MS (method 1): $R_t$=3.53 min; MS (ESIpos): m/z=468 $(M+H)^+$.

Example 34A

Methyl 4-{(3E)-2-[2-(4-cyanophenyl)ethyl]-4-[2-(pentyloxy)phenyl]but-3-en-1-yl}benzoate

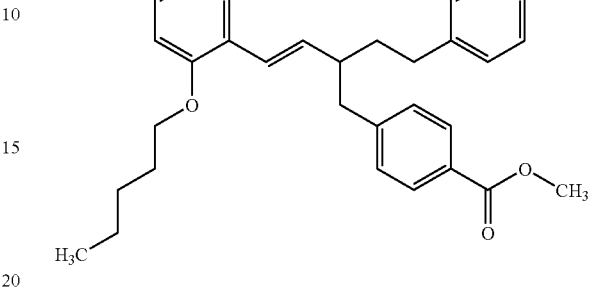

196 mg (0.41 mmol, 70% of theory) of the title compound are obtained by the process described in Example 30A starting from 200 mg (0.49 mmol) of methyl 4-[(3E)-2-[2-(4-cyanophenyl)ethyl]-4-(2-hydroxyphenyl)but-3-en-1-yl]benzoate, 101 mg (0.73 mmol) of potassium carbonate and 110 mg (0.73 mmol) of 1-pentyl bromide.

LC-MS (method 1): $R_t$=3.58 min; MS (ESIpos): m/z=482 $(M+H)^+$.

Example 35A

Methyl 4-{(3E)-2-[2-(4-cyanophenyl)ethyl]-4-[2-(hexyloxy)phenyl]but-3-en-1-yl}benzoate

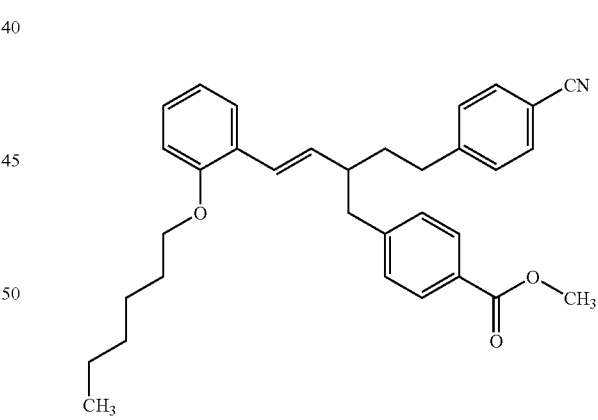

190 mg (0.37 mmol, 67% of theory) of the title compound are obtained by the process described in Example 30A starting from 200 mg (0.49 mmol) of methyl 4-[(3E)-2-[2-(4-cyanophenyl)ethyl]-4-(2-hydroxyphenyl)but-3-en-1-yl]benzoate, 101 mg (0.73 mmol) of potassium carbonate and 120 mg (0.73 mmol) of 1-hexyl bromide.

LC-MS (method 2): $R_t$=3.65 min; MS (ESIpos): m/z=496 $(M+H)^+$.

Example 36A

Methyl 4-{(3E)-2-[2-(4-cyanophenyl)ethyl]-4-[2-(heptyloxy)phenyl]but-3-en-1-yl}benzoate

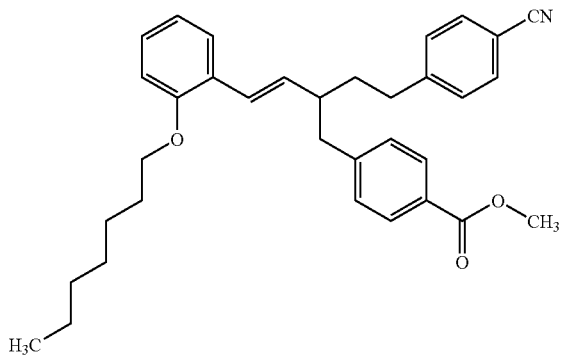 [SMILES: CCCCCCCOc1ccccc1/C=C/C(CCc1ccc(C#N)cc1)Cc1ccc(C(=O)OC)cc1]

190 mg (0.37 mmol, 67% of theory) of the title compound are obtained by the process described in Example 30A starting from 200 mg (0.49 mmol) of methyl 4-[(3E)-2-[2-(4-cyanophenyl)ethyl]-4-(2-hydroxyphenyl)but-3-en-1-yl]benzoate, 101 mg (0.73 mmol) of potassium carbonate and 131 mg (0.73 mmol) of 1-heptyl bromide.

LC-MS (method 6): $R_t$=8.0 min; MS (DCI): m/z=527 $(M+NH_4)^+$.

Example 37A

Methyl 4-{(3E/Z)-2-[2-(4-cyanophenyl)ethyl]-4-phenylbut-3-en-1-yl}benzoate

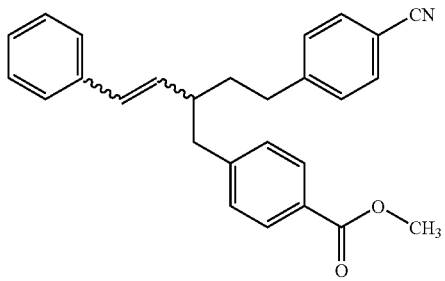 [SMILES: COC(=O)c1ccc(CC(C=Cc2ccccc2)CCc2ccc(C#N)cc2)cc1]

809 mg (1.87 mmol) of benzyltriphenylphosphine are suspended in 30 ml of THF and cooled to 0° C. with exclusion of oxygen. At this temperature, 1.46 ml (2.33 mmol) of n-butyllithium (1.6 M solution in hexane) are added dropwise, and the mixture is then stirred for 45 minutes. Subsequently, 500 mg (1.56 mmol) of methyl 4-[4-(4-cyanophenyl)-2-formylbutyl]benzoate, dissolved in 10 ml of THF, are rapidly added dropwise to the reaction solution. It is then stirred at 0° C. for 1 h and, after slowly warming to room temperature, stirred for a further 3 h. Ammonium chloride solution is added to the reaction mixture, which is evaporated. The residue is taken up in ethyl acetate and extracted with water. The organic phase is washed with sodium chloride solution, dried over sodium sulphate and evaporated. The resulting crude product is purified by flash chromatography on silica gel (mobile phase: cyclohexane/ethyl acetate 10:1). 484 mg (1.2 mmol, 79% of theory) of the title compound are obtained and are reacted directly without further characterization.

Example 38A

Triphenyl-[2-(trifluoromethoxy)benzyl]phosphonium bromide

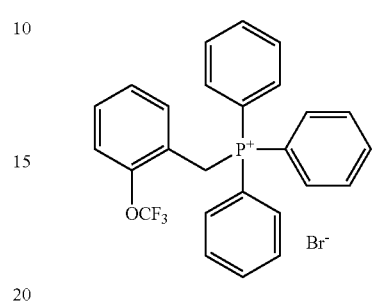

5 g (26 mmol) of 2-trifluoromethoxybenzyl bromide and 8.5 g (24.7 mmol) of triphenylphosphonium bromide are stirred under reflux in 100 ml of acetonitrile for 3 h. After cooling, the resulting precipitate is filtered off with suction and dried. 13.5 g (26 mmol, 100% of theory) of the title compound are obtained.

LC-MS (method 3): $R_t$=1.91 min; MS (ESIpos): m/z=437 $(M-Br)^+$.

Example 39A

Methyl 4-{(3E/Z)-2-[2-(4-cyanophenyl)ethyl]-4-[2-(trifluoromethoxy)phenyl]but-3-en-1-yl}benzoate

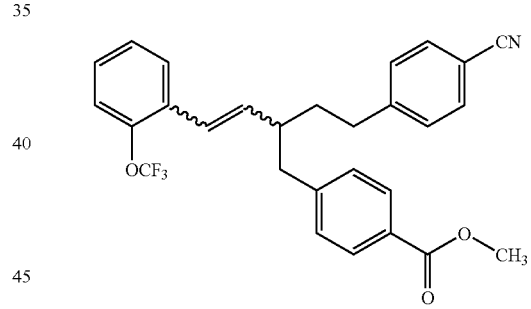

3.38 g (6.5 mmol) of triphenyl-[2-(trifluoromethoxy)benzyl]phosphonium bromide are suspended in 80 ml of THF and cooled to 0° C. with exclusion of oxygen. At this temperature, 5.1 ml (8.2 mmol) of n-butyllithium (1.6 M solution in hexane) are added dropwise, and then the mixture is stirred for 45 minutes. Subsequently, 1.75 g (5.45 mmol) of methyl 4-[4-(4-cyanophenyl)-2-formylbutyl]benzoate, dissolved in 20 ml of THF, are rapidly added dropwise to the reaction solution. It is stirred at 0° C. for 1 h and then warmed slowly to room temperature and stirred for a further 3 h. The reaction solution is mixed with ammonium chloride solution and evaporated. The residue is taken up in ethyl acetate and extracted with water. The organic phase is washed with sodium chloride solution, dried over sodium sulphate and evaporated. The resulting crude product is purified by flash chromatography on silica gel (mobile phase: cyclohexane/ethyl acetate 10:1). 2.065 g (4.3 mmol, 79% of theory) of the title compound are obtained.

LC-MS (method 3): $R_t$=3.33 min; MS (ESIpos): m/z=480 $(M+H)^+$.

Example 40A

Methyl 4-[(3E)-2-[2-(4-cyanophenyl)ethyl]-4-{2-[(5,5,5-trifluoropentyl)oxy]phenyl}but-3-en-1-yl]benzoate

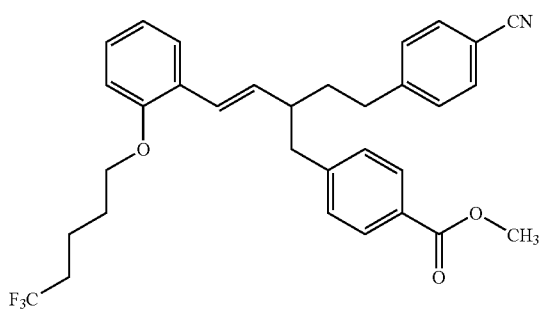 [SMILES: COC(=O)c1ccc(CC(/C=C/c2ccccc2OCCCCC(F)(F)F)CCc2ccc(C#N)cc2)cc1]

A solution of 200 mg (0.486 mmol) of methyl 4-[(3E)-2-[2-(4-cyanophenyl)ethyl]-4-(2-hydroxyphenyl)but-3-en-1-yl]benzoate in 10 ml of acetonitrile is mixed with 101 mg (0.73 mmol) of potassium carbonate and 149 mg (0.73 mmol) of 1,1,1-trifluoro-5-bromopentane [CAS Reg. No. 54932-74-00] and stirred under reflux for 12 h. After conversion is complete, the salts are filtered off and the mother liquor is evaporated. 205 mg (0.28 mmol, 79% of theory) of the title compound are obtained.

LC-MS (method 2): $R_t$=3.25 min; MS (ESIpos): m/z=536 (M+H)$^+$.

Example 41A

Methyl 4-{(3E)-2-[2-(4-cyanophenyl)ethyl]-4-[2-(3-phenylpropoxy)phenyl]but-3-en-1-yl}benzoate

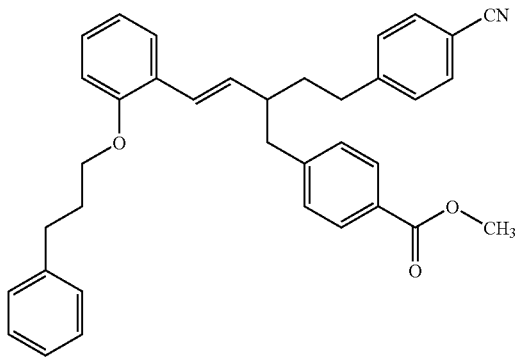 [SMILES: COC(=O)c1ccc(CC(/C=C/c2ccccc2OCCCc2ccccc2)CCc2ccc(C#N)cc2)cc1]

A solution of 200 mg (0.486 mmol) of methyl 4-[(3E)-2-[2-(4-cyanophenyl)ethyl]-4-(2-hydroxyphenyl)but-3-en-1-yl]benzoate in 5 ml of acetonitrile is mixed with 145 mg (0.73 mmol) of (3-bromopropyl)benzene and 100.76 mg (0.73 mmol) of potassium carbonate and then stirred under reflux for 12 h. After cooling, the potassium carbonate is filtered off and the filtrate is evaporated. 278 mg (0.45 mmol, 93% of theory, content 86%) of the title compound are obtained.

MS (DCI): m/z=547 (M+NH$_4$$^+$)

HPLC (method 2): $R_t$=5.53 min.

Example 42A

Methyl 4-{(3E)-2-[2-(4-cyanophenyl)ethyl]-4-[2-(4-phenylbutoxy)phenyl]but-3-en-1-yl}benzoate

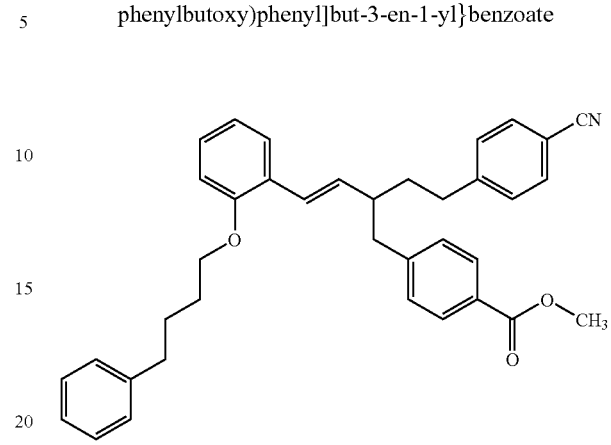

A solution of 200 mg (0.486 mmol) of methyl 4-[(3E)-2-[2-(4-cyanophenyl)ethyl]-4-(2-hydroxyphenyl)but-3-en-1-yl]benzoate in 5 ml of acetonitrile is mixed with 155 mg (0.73 mmol) of (4-bromobutyl)benzene and 100.76 mg (0.73 mmol) of potassium carbonate and then stirred under reflux for 12 h. After cooling, the potassium carbonate is filtered off and the filtrate is evaporated. 308 mg (0.41 mmol, 85% of theory, content 73%) of the title compound are obtained.

LC-MS (method 2): $R_t$=3.38 min; MS (ESIpos): m/z=544 (M+H)$^+$.

Example 43A

Methyl 4-[(3E)-2-[2-(4-cyanophenyl)ethyl]-4-(2-ethoxyphenyl)but-3-en-1-yl]benzoate

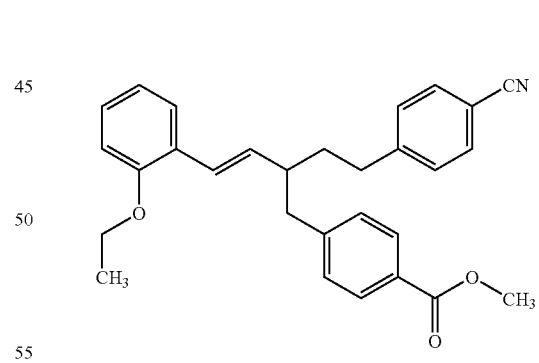

196 mg (0.44 mmol, 85% of theory, content 93%) of the title compound are obtained by the process described in Example 30A starting from 200 mg (0.486 mmol) of methyl 4-[(3E)-2-[2-(4-cyanophenyl)ethyl]-4-(2-hydroxyphenyl)but-3-en-1-yl]benzoate, 100.76 mg (0.73 mmol) of potassium carbonate and 79.44 mg (0.73 mmol) of bromoethane.

LC-MS (method 4): $R_t$=3.35 min; MS (ESIpos): m/z=440 (M+H)$^+$.

Example 44A

Methyl 4-[(3E)-2-[2-(4-cyanophenyl)ethyl]-4-(2-propoxyphenyl)but-3-en-1-yl]benzoate

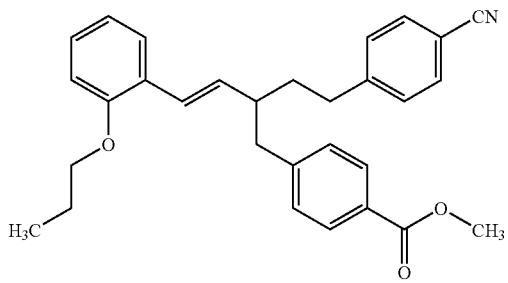 [SMILES: CCCOc1ccccc1/C=C/C(CCc1ccc(C#N)cc1)Cc1ccc(C(=O)OC)cc1]

201 mg (0.35 mmol, 72% of theory, content 79%) of the title compound are obtained by the process described in Example 30A starting from 200 mg (0.486 mmol) of methyl 4-[(3E)-2-[2-(4-cyanophenyl)ethyl]-4-(2-hydroxyphenyl)but-3-en-1-yl]benzoate, 100.76 mg (0.73 mmol) of potassium carbonate and 89.67 mg (0.73 mmol) of 1-bromopropane.

LC-MS (method 4): $R_t$=3.41 min; MS (ESIpos): m/z=454 (M+H)$^+$.

Example 45A

Diallyl 2-(4-cyanobenzyl)malonate

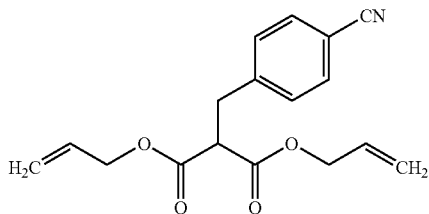 [SMILES: C=CCOC(=O)C(Cc1ccc(C#N)cc1)C(=O)OCC=C]

19.79 g (0.494 mol) of sodium hydride are added in portions to a solution of 121.5 g (0.659 mol) of diallyl malonate in 1.5 litres of dioxane at 0° C. (caution: evolution of hydrogen). After warming to room temperature, the mixture is stirred at 40° C. for 1 hour. Subsequently, 50 g (0.329 mol) of 4-chloromethylbenzonitrile, dissolved in 500 ml of dioxane, are slowly added dropwise at 40° C., and the reaction solution is stirred at 110° C. overnight. After cooling to room temperature, the reaction mixture is added to 1200 ml of water. Care must be taken during this that the pH remains <7 (if necessary, a few ml of 1 M hydrochloric acid are metered in until the pH is about 2). The mixture is then extracted three times with ethyl acetate, and the combined organic phases are washed with saturated sodium chloride solution and dried over sodium sulphate. After filtration, the solvent is evaporated to dryness in vacuo. Excess diallyl malonate is then removed by high vacuum distillation (boiling point: 57° C., 0.074 mbar). The distillation residue is purified by flash chromatography on silica gel (mobile phase: petroleum ether/ethyl acetate 20:1). 67 g (0.22 mol, 67% of theory) of a colourless solid are obtained.

$^1$H-NMR (300 MHz, DMSO-d$_6$, δ/ppm): 7.77 (2H, d), 7.48 (2H, d), 5.90-5.73 (2H, m), 5.29-5.13 (4H, m), 4.64-4.50 (4H, m), 4.09 (1H, t), 3.21 (2H, d).

MS (DCI): m/z=317 (M+NH$_4^+$).

Example 46A

Diallyl 2-(4-cyanobenzyl)-2-[2-(4-methoxycarbonylphenyl)ethyl]malonate

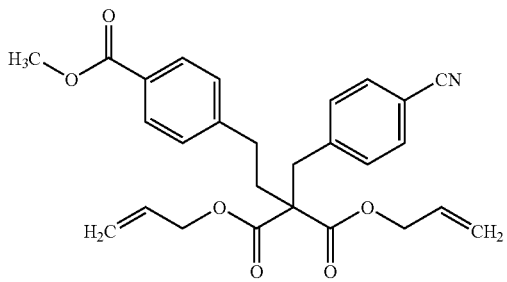 [SMILES: C=CCOC(=O)C(CCc1ccc(C(=O)OC)cc1)(Cc1ccc(C#N)cc1)C(=O)OCC=C]

7.13 g (178.36 mmol) of sodium hydride are added in portions to a solution of 48.53 g (162.14 mmol) of diallyl 2-(4-cyanobenzyl)malonate from Example 45A in 180 ml of DMF at 0° C. The reaction solution is then allowed to reach room temperature and is stirred for 30 min. The reaction solution is then cooled again to 0° C., 55 g (194.57 mmol) of methyl 4-(2-bromoethyl)benzoate [CAS Reg. No. 136333-97-6] in 195 ml of DMF are added, and the mixture is stirred at this temperature for 30 min. The mixture is subsequently stirred at room temperature overnight. Water is added dropwise to the reaction mixture, which is then extracted three times with ethyl acetate, and the combined organic phases are washed with saturated brine and dried over sodium sulphate. After filtration, the solvent is evaporated to dryness in vacuo. The resulting crude product is purified by flash chromatography on silica gel (mobile phase: petroleum ether/ethyl acetate 10:1). 33.4 g (72.37 mmol, 44% of theory) of a colourless solid are obtained.

$^1$H-NMR (300 MHz, CDCl$_3$, δ/ppm): 7.89 (2H, d), 7.79 (2H, d), 7.38 (2H, d), 7.32 (2H, d), 5.97-5.81 (2H, m), 5.38-5.20 (4H, m), 4.61 (4H, d), 3.82 (3H, s), 3.39 (2H, s), 2.77-2.61 (2H, m), 1.99-1.84 (2H, m).

MS (DCI): m/z=479 (M+NH$_4^+$).

Example 47A

Methyl 4-[3-carboxy-4-(4-cyanophenyl)butyl]benzoate

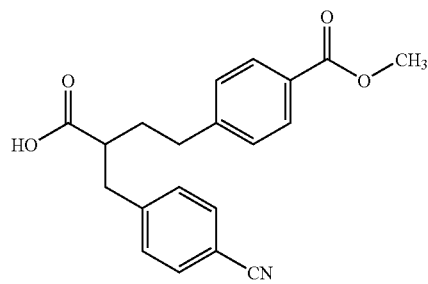 [SMILES: COC(=O)c1ccc(CCC(Cc2ccc(C#N)cc2)C(=O)O)cc1]

A solution of 7.5 g (16.25 mmol) of diallyl 2-(4-cyanobenzyl)-2-[2-(4-methoxycarbonylphenyl)ethyl]malonate from Example 46A, 0.3 g (1.14 mmol) of triphenylphosphine and 70 mg of palladium acetate in 170 ml of dioxane is mixed at room temperature with a solution of 7.47 ml (53.63 mmol) of triethylamine and 1.53 ml (40.63 mmol) of formic acid in 170 ml of dioxane. The reaction mixture is then stirred at 100° C. for 2 h. After conversion is complete, the reaction solution is cooled and the solvent is removed in vacuo. The residue is taken up in ethyl acetate and water and acidified with 1 N hydrochloric acid, and the organic phase is separated off. The aqueous phase is extracted three times more with ethyl acetate, and the organic phases are subsequently combined, washed with saturated brine and dried over sodium sulphate. After filtration, the solution is evaporated in vacuo. 5.48 g (89% of theory, 90% purity) of a colourless solid are obtained.

$^1$H-NMR (400 MHz, DMSO-d$_6$, δ/ppm): 12.46-12.29 (1H, broad), 7.88 (2H, d), 7.74 (2H, d), 7.39 (2H, d), 7.31 (2H, d), 3.83 (3H, s), 2.99-2.83 (2H, m), 2.79-2.56 (3H, m), 1.93-1.67 (2H, m).

MS (DCI): m/z=355 (M+NH$_4^+$).

Example 48A

Methyl 4-[3-(4-cyanobenzyl)-4-hydroxybutyl]benzoate

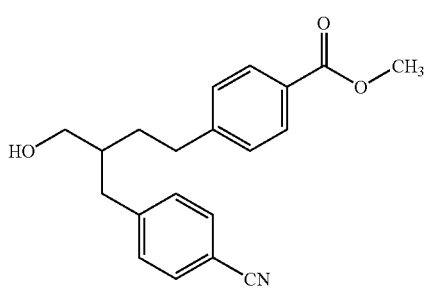 [SMILES: COC(=O)c1ccc(CCC(CO)Cc2ccc(C#N)cc2)cc1]

47.43 ml (47.43 mmol) of a 1 M borane-THF complex solution are added dropwise to a solution of 8 g (23.71 mmol) of methyl 4-[3-carboxy-4-(4-cyanophenyl)butyl]benzoate from Example 47A in 200 ml of THF at −10° C. After the mixture has warmed to −5° C. it is stirred at this temperature for 4 h. After the reaction is complete, the reaction mixture is mixed with saturated sodium bicarbonate solution and the solvent is evaporated to dryness. The residue is taken up in dichloromethane, dried over sodium sulphate and, after filtration, again freed of solvent. The resulting crude product is purified by flash chromatography on silica gel (mobile phase: ethyl acetate/cyclohexane 1:10). 5.8 g (98% purity, 74% of theory) of a colourless solid are obtained.

$^1$H-NMR (300 MHz, DMSO-d$_6$, δ/ppm): 7.86 (2H, d), 7.73 (2H, d), 7.38 (2H, d), 7.30 (2H, d), 4.60 (1H, t), 3.83 (3H, s), 3.32 (2H, t), 2.81-2.57 (4H, m), 1.79-1.56 (2H, m), 1.54-1.39 (1H, m).

MS (DCI): m/z=341 (M+NH$_4^+$).

Example 49A

Methyl 4-[3-(4-cyanobenzyl)-4-oxobutyl]benzoate

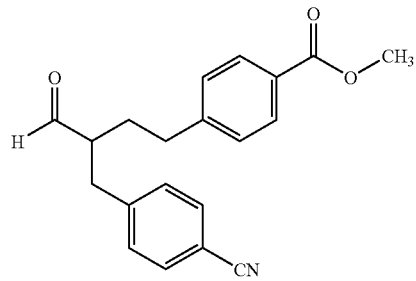 [SMILES: COC(=O)c1ccc(CCC(C=O)Cc2ccc(C#N)cc2)cc1]

320 mg (1.48 mmol) of pyridinium chlorochromate (PCC) are added to a solution of 400 mg (1.24 mmol) of methyl 4-[3-(4-cyanobenzyl)-4-hydroxybutyl]benzoate from Example 48A in 7 ml of dichloromethane, and the mixture is stirred at room temperature for 5 hours. After conversion is complete, about 1 g of silica gel is added, and the solvent is removed in vacuo to dryness. The residue is purified by flash chromatography on silica gel (mobile phase: cyclohexane/ethyl acetate 10:1→4:1). 302 mg (90% purity, 69% of theory) of a colourless solid are obtained.

$^1$H-NMR (300 MHz, DMSO-d$_6$, δ/ppm): 9.68 (1H, s), 7.87 (2H, d), 7.77 (2H, d), 7.43 (2H, d), 7.31 (2H, d), 3.86 (3H, s), 3.16-3.03 (1H, m), 2.94-2.81 (1H, m), 2.80-2.55 (3H, m), 1.99-1.81 (1H, m), 1.78-1.61 (1H, m).

MS (DCI): m/z=339 (M+NH$_4^+$).

Example 50A

Methyl E-4-[3-(4-cyanobenzyl)-5-(2-hydroxyphenyl)pent-4-enyl]benzoate

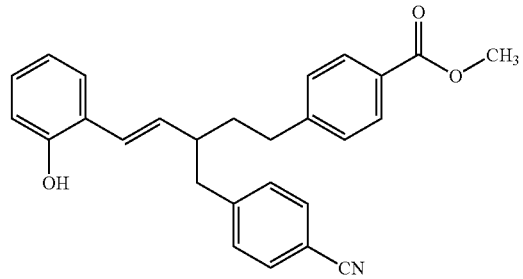 [SMILES: COC(=O)c1ccc(CCC(/C=C/c2ccccc2O)Cc2ccc(C#N)cc2)cc1]

73.8 ml (118 mmol) of a 1.6 M solution of n-butyllithium in hexane are slowly added dropwise to a solution of 23.22 g (51.7 mmol) of (2-hydroxybenzyl)triphenylphosphonium bromide in 130 ml of anhydrous THF at 0° C. Then, at this temperature, 15.5 g (42 mmol, content 87%) of methyl 4-[3-(4-cyanobenzyl)-4-oxobutyl]benzoate from Example 49A, dissolved in 130 ml of THF, are slowly metered in. After warming to room temperature, the reaction solution is stirred for 12 h and, after addition of a little water, evaporated to dryness. The residue is taken up in ethyl acetate, washed with water and saturated brine and dried over sodium sulphate. After filtration, the solvent is evaporated to dryness. The resulting crude product is purified by flash chromatography on silica gel (mobile phase: cyclohexane/ethyl acetate 4:1→2:1). 11.3 g (27.5 mmol, 65% of theory) of a colourless solid are obtained.

$^1$H-NMR (300 MHz, DMSO-$d_6$, δ/ppm): 9.47 (1H, s), 7.88 (2H, d), 7.71 (2H, d), 7.42-7.27 (5H, m), 7.01 (1H, t), 6.81-6.68 (2H, m), 6.45 (1H, d), 6.12-6.00 (1H, m), 3.84 (3H, s), 3.42 (2H, m), 2.95-2.56 (3H, m), 1.88-1.56 (2H, m).

MS (DCI): m/z=429 (M+NH$_4^+$).

11.3 g (27.5 mmol) of the racemic methyl E-4-[3-(4-cyanobenzyl)-5-(2-hydroxyphenyl)pent-4-enyl]benzoate obtained in this way are further fractionated by preparative HPLC on a chiral phase. Respectively 4.14 g and 3.69 g of the two E isomers are obtained in each case as enantiopure colourless solids (see Examples 51A and 52A).

Example 51A

Methyl E-4-[3-(4-cyanobenzyl)-5-(2-hydroxyphenyl)pent-4-enyl]benzoate (Enantiomer 1)

Enantiomer Separation Method:
Column: Daicel Chiralpak AD-H 250 mm×4.6 mm, 5 µm; eluent: isohexane/isopropanol 50:50 (v/v); flow rate: 1 ml/min; UV detection: 210 nm; temperature: 25° C.
$R_t$ 6.77 min; purity 96.85%; >99.5% ee
Yield: 4.14 g
LC-MS (method 7): $R_t$=3.03 min; MS (ESIpos): m/z=412 (M+H)$^+$.

Example 52A

Methyl E-4-[3-(4-cyanobenzyl)-5-(2-hydroxyphenyl)pent-4-enyl]benzoate (Enantiomer 2)

Enantiomer separation method: see Example 51A.
$R_t$ 7.82 min; purity 96%; >99% ee
Yield: 3.69 g
LC-MS (method 7): $R_t$=3.03 min; MS (ESIpos): m/z=412 (M+H)$^+$.

Example 53A 1-(5-Bromopentyl)-4-(trifluoromethyl)benzene

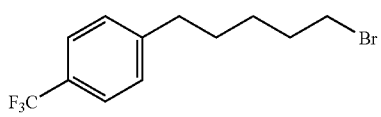 [SMILES: FC(F)(F)c1ccc(CCCCCBr)cc1]

1.34 g (55 mmol) of activated magnesium turnings are added to a solution of 11.25 g (50 mmol) of 1-bromo-4-trifluoromethyl)benzene in 50 ml of THF at room temperature. The reaction solution heats up until it refluxes (exothermic reaction), during which the magnesium turnings almost completely dissolve. After the exothermic reaction subsides, the dark brown solution is stirred under reflux for a further 15 min. The approx. 1 M Grignard solution obtained in this way is then cooled to room temperature again.

In parallel with this, a pale green solution of 359 mg (2.5 mmol) of copper(I) bromide and 435 mg (5 mmol) of anhydrous lithium bromide in 10 ml of THF is mixed at room temperature with a solution of 20.5 ml (150 mmol) of 1,5-dibromopentane in 40 ml of THF. The reaction mixture is heated to a bath temperature of 40° C. and then the freshly prepared Grignard solution is slowly added. After addition of the Grignard solution is complete, the reaction mixture is stirred at 50-55° C. for 1.5 h and subsequently stirred at room temperature overnight. Ammonium chloride solution (20 g of ammonium chloride in 100 ml of water) is added dropwise to the reaction mixture, which is hydrolysed while cooling in ice. The mixture is extracted three times with diethyl ether, and the combined organic phases are washed with saturated brine and dried over sodium sulphate. After filtration, the solvent is evaporated to dryness in vacuo. The resulting crude product is purified by fractional distillation. 7.11 g (24.1 mmol, 48% of theory; boiling point: 80° C., 0.15 Torr) of a colourless oil are obtained.

$^1$H-NMR (200 MHz, DMSO-$d_6$, δ/ppm): 7.62 (2H, d), 7.43 (2H, d), 3.53 (2H, t), 2.68 (2H, t), 1.92-1.72 (2H, m), 1.71-1.51 (2H, m), 1.49-1.29 (2H, m).

MS (EI): m/z=294 (M$^+$).

Example 54A 1-(Difluoromethyl)-4-(trifluoromethoxy)benzene

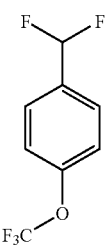

5 g (22.6 mmol) of 2-methoxy-N-(2-methoxyethyl)-N-(trifluoro-λ$^4$-sulphanyl)ethanamine, dissolved in 6 ml of dichloromethane, are slowly added to a solution of 2.527 g (13.29 mmol) of trifluoromethoxybenzaldehyde in 6 ml of dichloromethane at room temperature under argon. 155 µl of ethanol are then metered into the reaction solution, during which the temperature rises slightly to 29° C. The mixture is then stirred at room temperature overnight. After conversion is complete (reaction checked by GC-MS), the reaction solution is slowly hydrolysed with saturated sodium bicarbonate solution (strong evolution of gas) and taken up in water/dichloromethane. The organic phase is separated off, dried over magnesium sulphate and, after filtration, evaporated in vacuo. 2.38 g (11.22 mmol, 84.4% of theory) of a colourless liquid are obtained.

GC-MS (method 1): $R_t$=2.46 min; MS (ESIpos): m/z=212 (M$^+$).

Example 55A

1-[Bromo(difluoro)methyl]-4-(trifluoromethoxy)benzene

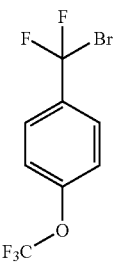

A solution of 2.38 g (11.22 mmol) of 1-(difluoromethyl)-4-(trifluoromethoxy)benzene and 6.19 g (34.78 mmol) of N-bromosuccinimide (NBS) in 25 ml of tetrachloromethane is irradiated with exclusion of oxygen using a sun lamp. During this, the solvent reaches its boiling point. It is irradiated under reflux for 48 hours. The mixture is then allowed to cool to room temperature, precipitated succinimide is filtered off, and the filtrate is evaporated to dryness. The resulting crude product is purified by flash chromatography on silica gel (mobile phase: cyclohexane). 1.73 g (5.94 mmol, 53% of theory) of a yellowish oil are obtained.

GC-MS (method 1): $R_t$=2.93 min; MS (ESIpos): m/z=211 (M-Br)$^+$.

Example 56A

Methyl 4-{(4E)-3-(4-cyanobenzyl)-5-[2-({4-[1,2,2,2-tetrafluoro-1-(trifluoromethyl)ethyl]benzyl}-oxy)phenyl]pent-4-en-1-yl}benzoate

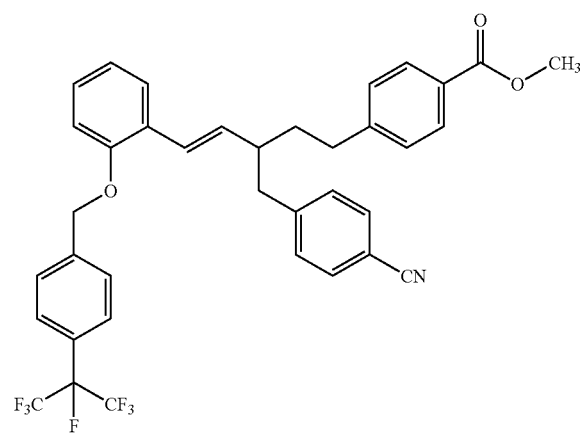 [SMILES: COC(=O)c1ccc(CCC(/C=C/c2ccccc2OCc2ccc(C(F)(C(F)(F)F)C(F)(F)F)cc2)Cc2ccc(C#N)cc2)cc1]

A solution of 150 mg (0.365 mmol) of methyl E-4-[3-(4-cyanobenzyl)-5-(2-hydroxyphenyl)pent-4-enyl]benzoate (enantiomer 1, Example 51A) in 3 ml of dry acetonitrile is mixed with 139 mg (0.47 mmol) of 1-(chloromethyl)-4-[1,2,2,2-tetrafluoro-1-(trifluoromethyl)ethyl]benzene [prepared as described in EP 0 009 787-A2] and 100 mg (0.73 mmol) of anhydrous potassium carbonate and then heated under reflux for 12 h. The mixture is then filtered and the filtrate is evaporated to dryness. The residue is purified by chromatography on silica gel (mobile phase: cyclohexane/ethyl acetate 4:1). 210 mg (0.31 mmol, 86% of theory) of an oil are isolated.

$^1$H-NMR (400 MHz, DMSO-d$_6$, δ/ppm): 7.83 (2H, d), 7.70-7.60 (6H, m), 7.42 (1H, d), 7.36 (3H, d), 7.30 (2H, d), 7.20 (1H, t), 7.04 (1H, d), 6.93 (1H, t), 6.49 (1H, d), 6.17-6.06 (1H, m), 5.20 (2H, s), 3.82 (3H, s), 2.95-2.85 (1H, m), 2.80-2.69 (2H, m), 2.68-2.58 (1H, m), 2.57-2.46 (1H, m), 1.88-1.74 (1H, m), 1.73-1.60 (1H, m).

LC-MS (method 2): $R_t$=3.41 min; m/z=670 (M+H)$^+$.

Example 57A

4-Fluoro-2-(hydroxymethyl)phenol

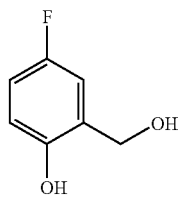

27.1 g (159.28 mmol) of methyl 5-fluoro-2-hydroxybenzoate are introduced into 500 ml of dry THF with exclusion of oxygen and cooled to 0° C. Subsequently, while cooling, 238 ml (238 mmol) of a 1 M solution of lithium aluminium hydride in THF are slowly added dropwise, and the mixture is stirred at 0° C. for 1 hour and then at RT overnight. After reaction is complete, saturated ammonium chloride solution is added to the mixture, and it is taken up in dichloromethane. The organic phase is separated off and dried over sodium sulphate. After filtration, the solvent is removed in vacuo. The crude product is purified by chromatography on silica gel (mobile phase: cyclohexane/ethyl acetate 20:1). 18.0 g (126.6 mmol, 79% of theory) of a colourless solid are isolated.

$^1$H-NMR (400 MHz, DMSO-d$_6$, δ/ppm): 9.32 (1H, s), 7.06-7.03 (1H, m), 6.86-6.81 (1H, m), 6.74-6.71 (1H, m), 5.09 (1H, t), 4.45 (2H, d).

Example 58A (5-Fluoro-2-hydroxybenzyl)(triphenyl)phosphonium bromide

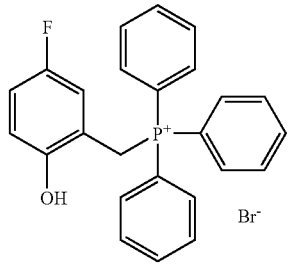 [SMILES: Oc1ccc(F)cc1C[P+](c1ccccc1)(c1ccccc1)c1ccccc1 ; [Br-]]

18.6 g (130.87 mmol) of 4-fluoro-2-(hydroxymethyl)phenol and 42.67 g (124.32 mmol) of triphenylphosphonium hydrobromide are stirred under reflux in 186 ml of acetonitrile for 3 h. After cooling, the resulting precipitate is filtered off with suction and dried. 58 g (124 mmol, 100% of theory) of the title compound are obtained.

$^1$H-NMR (400 MHz, DMSO-d$_6$, δ/ppm): 9.82 (1H, s), 7.95-7.84 (3H, m), 7.79-7.62 (12H, m), 7.02-6.91 (1H, m), 6.75-6.67 (1H, m), 6.66-6.58 (1H, m), 4.90 (2H, d).

Example 59A

Diallyl 2-[4-(methoxycarbonyl)benzyl]-2-{2-[4-(methoxycarbonyl)phenyl]ethyl}malonate

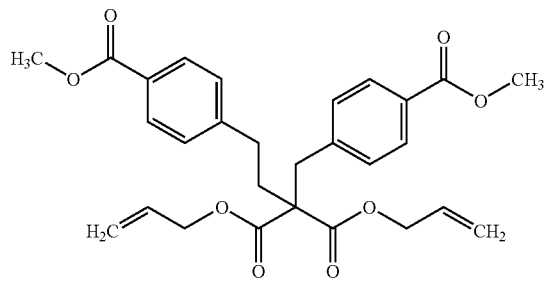

A solution of 42.61 g (128 mmol) of diallyl 2-(4-methoxycarbonylbenzyl)malonate in 450 ml of DMF is mixed at room temperature with 62.66 g (192 mmol) of caesium carbonate and 46.75 g (154 mmol) of methyl 4-(2-bromoethyl)benzoate [CAS Reg. No. 136333-97-6]. The mixture is then stirred at room temperature overnight. After conversion is complete, the reaction solution is evaporated to dryness, and the residue is taken up in water and extracted three times with ethyl acetate. The combined organic phases are then washed with saturated brine and dried over sodium sulphate. After filtration, the solvent is evaporated to dryness in vacuo. The resulting crude product is purified by flash chromatography on silica gel (mobile phase: cyclohexane/ethyl acetate 13:1). 41.35 g (83.6 mmol, 65% of theory) of a colourless solid are obtained.

LC-MS (method 2): $R_t$=2.92 min; m/z=495 (M+H$^+$).

Example 60A

2-[4-(Methoxycarbonyl)benzyl]-4-[4-(methoxycarbonyl)phenyl]butanoic acid

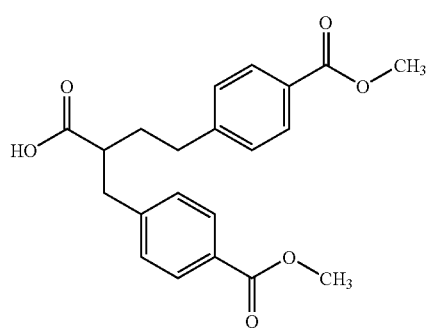 [SMILES: COC(=O)c1ccc(CCC(Cc2ccc(C(=O)OC)cc2)C(=O)O)cc1]

A solution of 40 g (80.9 mmol) of diallyl 2-[4-(methoxycarbonyl)benzyl]-2-{2-[4-(methoxycarbonyl)phenyl]ethyl}malonate, 1.49 g (5.67 mmol) of triphenylphosphine and 363 mg of palladium acetate in 500 ml of dioxane is mixed at room temperature with a solution of 37.2 ml (267 mmol) of triethylamine and 7.6 ml (202 mmol) of formic acid in 100 ml of dioxane. The reaction mixture is then stirred at 110° C. overnight. After conversion is complete, the reaction solution is cooled, and the solvent is removed in vacuo. The resulting residue is purified by flash chromatography on silica gel (mobile phase: cyclohexane/ethyl acetate 4:1). 20.98 g (56.6 mmol, 70% of theory) of a colourless solid are obtained.

$^1$H-NMR (400 MHz, DMSO-d$_6$, δ/ppm): 12.32 (1H, s), 7.91-7.82 (4H, m), 7.37-7.27 (4H, m), 3.83 (6H, s), 2.99-2.81 (2H, m), 2.77-2.56 (3H, m), 1.92-1.67 (2H, m).

LC-MS (method 7): $R_t$=2.45 min; m/z=371 (M+H$^+$).

Example 61A

Dimethyl 4,4'-[2-(hydroxymethyl)butane-1,4-diyl]dibenzoate

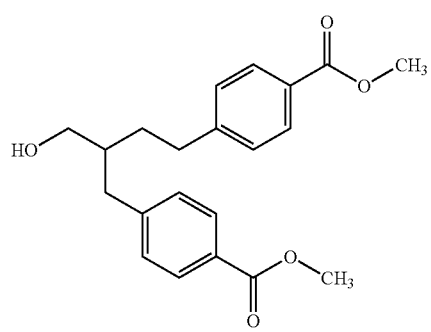 [SMILES: COC(=O)c1ccc(CCC(CO)Cc2ccc(C(=O)OC)cc2)cc1]

112.8 ml (112.8 mmol) of a 1 M boran-THF complex solution are added dropwise to a solution of 20.9 g (56.4 mmol) of 2-[4-(methoxycarbonyl)benzyl]-4-[4-(methoxycarbonyl)phenyl]butanoic acid in 600 ml of THF at −10° C. The reaction mixture is then warmed to 0° C. and stirred at this temperature for 4 h. After reaction is complete, saturated ammonium chloride solution is added to the reaction mixture, which is diluted with water and ethyl acetate, the phases are separated, and the aqueous phase is back-extracted twice with ethyl acetate. The combined organic phases are dried over sodium sulphate and, after filtration, freed of solvent in vacuo. 20.11 g (94% purity, 100% of theory) of a colourless solid are obtained.

LC-MS (method 2): $R_t$=2.27 min; m/z=357 (M+H$^+$).

Example 62A

Dimethyl 4,4'-(2-formylbutane-1,4-diyl)dibenzoate

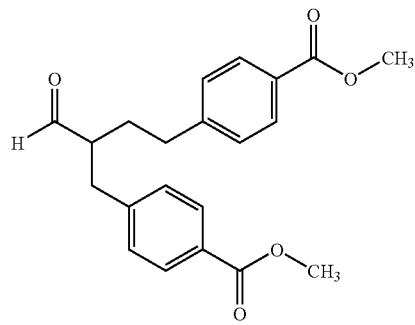 [SMILES: COC(=O)c1ccc(CCC(C=O)Cc2ccc(C(=O)OC)cc2)cc1]

A solution of 18.02 g (50.5 mmol) of dimethyl 4,4'-[2-(hydroxymethyl)butane-1,4-diyl]dibenzoate in 350 ml of dichloromethane is mixed with 13.07 g (60.6 mmol) of pyridinium chlorochromate (PCC) and stirred at room temperature for 12 hours. After conversion is complete, about 60 g of silica gel are added, and the solvent is removed in vacuo to dryness. The residue is purified by flash chromatography on silica gel (mobile phase: cyclohexane/ethyl acetate 5:1→4:1). 14.73 g (41.46 mmol, 82% of theory) of a colourless oil are obtained.

LC-MS (method 7): $R_t$=2.61 min; m/z=355 (M+H$^+$).

Example 63A

Methyl 4-{(4E)-5-(5-fluoro-2-hydroxyphenyl)-3-[4-(methoxycarbonyl)benzyl]pent-4-en-1-yl}benzoate

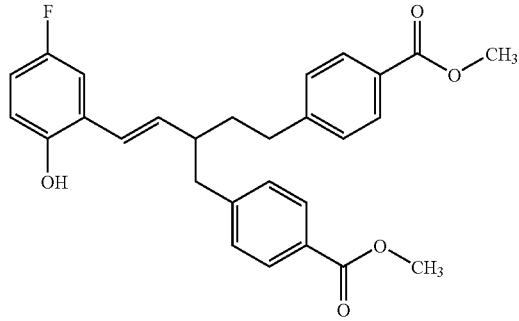 [SMILES: COC(=O)c1ccc(CCC(/C=C/c2cc(F)ccc2O)Cc2ccc(C(=O)OC)cc2)cc1]

21.65 ml (54.12 mmol) of a 2.5 M solution of n-butyllithium in hexane are slowly added dropwise to a solution of 10.84 g (23.2 mmol) of (5-fluoro-2-hydroxybenzyl)(triphenyl)phosphonium bromide in 150 ml of THF at 0° C., and the mixture is stirred at this temperature for 45 min. Subsequently, at this temperature, 6.85 g (19.33 mmol) of dimethyl 4,4'-(2-formylbutane-1,4-diyl)dibenzoate in 100 ml of THF are slowly metered in. The reaction solution is stirred at 0° C. for 3 h and, after addition of saturated ammonium chloride solution, diluted with water and ethyl acetate, the organic phase is separated off and the aqueous phase is back-extracted twice more with ethyl acetate. The combined organic phases are dried over sodium sulphate and filtered, and the solvent is removed to dryness. The resulting crude product is purified by flash chromatography on silica gel (mobile phase: cyclohexane/ethyl acetate 4:1). 8.21 g (17.75 mmol, 76% of theory) of a yellowish oil are obtained.

LC-MS (method 7): $R_t$=3.14 min; m/z=463 (M+H$^+$).

Example 64A

Methyl 4-{(4E)-5-(5-fluoro-2-{[4-(trifluoromethyl)benzyl]oxy}phenyl)-3-[4-(methoxycarbonyl)benzyl]pent-4-en-1-yl}benzoate

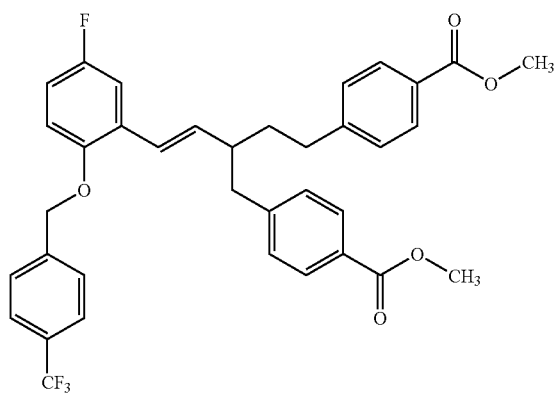 [SMILES: COC(=O)c1ccc(CCC(/C=C/c2cc(F)ccc2OCc2ccc(C(F)(F)F)cc2)Cc2ccc(C(=O)OC)cc2)cc1]

A solution of 1.4 g (3.03 mmol) of methyl 4-{(4E)-5-(5-fluoro-2-hydroxyphenyl)-3-[4-(methoxycarbonyl)benzyl]pent-4-en-1-yl}benzoate in 30 ml of dry acetonitrile is mixed with 868 mg (3.6 mmol) of 1-(bromomethyl)-4-(trifluoromethyl)benzene and 627 mg (4.5 mmol) of anhydrous potassium carbonate and then heated under reflux for 12 h. The mixture is subsequently filtered, and the filtrate is evaporated to dryness. The residue is purified by chromatography on silica gel (mobile phase: cyclohexane/ethyl acetate 5:1). 1.23 g (1.98 mmol, 65% of theory) of a colourless oil are isolated.

$^1$H-NMR (400 MHz, DMSO-d$_6$, δ/ppm): 7.88-7.79 (4H, m), 7.70 (2H, d), 7.54 (2H, d), 7.33-7.24 (5H, m), 7.06-6.97 (2H, m), 6.44 (1H, d), 6.25-6.15 (1H, m), 5.14 (2H, s), 3.82 (3H, s), 3.79 (3H, s), 2.93-2.82 (1H, m), 2.79-2.68 (2H, m), 2.67-2.57 (1H, m), 2.56-2.45 (1H, m), 1.89-1.76 (1H, m), 1.75-1.62 (1H, m).

LC-MS (method 8): $R_t$=5.01 min; m/z=621 (M+H$^+$). 412 mg (0.66 mmol) of the racemic methyl 4-{(4E)-5-(5-fluoro-2-{[4-(trifluoromethyl)benzyl]-oxy}phenyl)-3-[4-(methoxycarbonyl)benzyl]pent-4-en-1-yl}benzoate obtained in this way are further fractionated by preparative HPLC on a chiral phase. Respectively 93 mg and 87 mg of the two E-isomers are obtained in each case enantiopure as colourless solids (see Examples 65A and 66A).

Example 65A

Methyl 4-{(4E)-5-(5-fluoro-2-{[4-(trifluoromethyl)benzyl]oxy}phenyl)-3-[4-(methoxycarbonyl)benzyl]pent-4-en-1-yl}benzoate (enantiomer 1)

Enantiomer Separation Method:
Column: Daicel Chiralpak AD-H 250 mm×20 mm, 5 μm; eluent: isohexane/isopropanol 60:40 (v/v); flow rate: 15 ml/min; UV detection: 220 nm; temperature: 28° C.

$R_t$ 7.55 min; purity 99%; >99.5% ee
Yield: 93 mg.

Example 66A

Methyl 4-{(4E)-5-(5-fluoro-2-{[4-(trifluoromethyl)benzyl]oxy}phenyl)-3-[4-(methoxycarbonyl)benzyl]pent-4-en-1-yl}benzoate (enantiomer 2)

Enantiomer separation method: see Example 65A.
$R_t$ 8.48 min; purity >98.5%; >97.5% ee
Yield: 87 mg.

Example 67A

Methyl 4-{(4E)-5-(5-fluoro-2-{[4-(trifluoromethoxy)benzyl]oxy}phenyl)-3-[4-(methoxycarbonyl)benzyl]pent-4-en-1-yl}benzoate

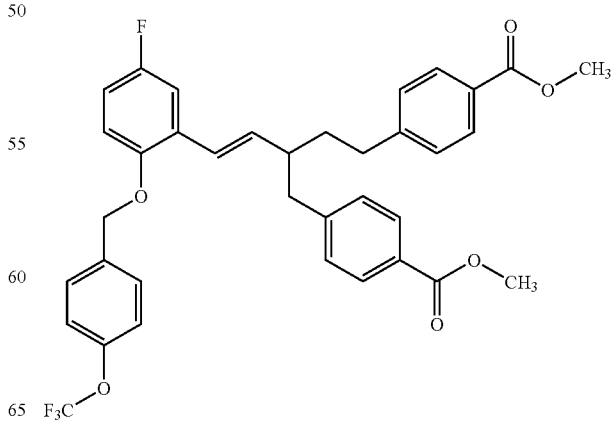

A solution of 750 mg (1.62 mmol) of methyl 4-{(4E)-5-(5-fluoro-2-hydroxyphenyl)-3-[4-(methoxycarbonyl)benzyl]pent-4-en-1-yl}benzoate in 19 ml of dry acetonitrile is mixed with 496 mg (1.95 mmol) of 1-(bromomethyl)-4-(trifluoromethoxy)benzene and 336 mg (2.43 mmol) of anhydrous potassium carbonate and then heated under reflux for 12 h. The mixture is subsequently filtered, and the filtrate is evaporated to dryness. The residue is purified by chromatography on silica gel (mobile phase: cyclohexane/ethyl acetate 5:1). 883 mg (1.39 mmol, 85% of theory) of a colourless oil are isolated.

LC-MS (method 7): $R_t$=3.54 min; m/z=637 (M+H$^+$).

880 mg (1.38 mmol) of the racemic methyl 4-{(4E)-5-(5-fluoro-2-{[4-(trifluoromethoxy)benzyl]-oxy}phenyl)-3-[4-(methoxycarbonyl)benzyl]pent-4-en-1-yl}benzoate obtained in this way are further fractionated by preparative HPLC on a chiral phase. Respectively 444 mg and 320 mg of the two E-isomers are obtained in each case enantiopure as colourless solids (see Examples 68A and 69A).

Example 68A

Methyl 4-{(4E)-5-(5-fluoro-2-{[4-(trifluoromethoxy)benzyl]oxy}phenyl)-3-[4-(methoxycarbonyl)benzyl]pent-4-en-1-yl}benzoate (enantiomer 1)

Enantiomer Separation Method:
Column: Daicel Chiralpalc AD-H 250 mm×20 mm, 5 μm; eluent: isohexane/isopropanol 70:30 (v/v); flow rate: 15 ml/min; UV detection: 220 nm; temperature: 30° C.
$R_t$ 6.05 min; purity >99.5%; >99.5% ee
Yield: 444 mg
$^1$H-NMR (400 MHz, DMSO-d$_6$, δ/ppm): 7.88-7.78 (4H, m), 7.48 (2H, d), 7.37-7.21 (7H, m), 7.09-6.95 (2H, m), 6.41 (1H, d), 6.25-6.14 (1H, m), 5.06 (2H, s), 3.82 (3H, s), 3.79 (3H, s), 2.93-2.82 (1H, m), 2.79-2.67 (2H, m), 2.66-2.56 (1H, m), 2.55-2.42 (1H, m), 1.88-1.75 (1H, m), 1.74-1.61 (1H, m).
LC-MS (method 2): $R_t$=3.37 min; m/z=637 (M+H$^+$).

Example 69A

Methyl 4-{(4E)-5-(5-fluoro-2-{[4-(trifluoromethoxy)benzyl]oxy}phenyl)-3-[4-(methoxycarbonyl)benzyl]pent-4-en-1-yl}benzoate (enantiomer 2)

Enantiomer separation method: see Example 68A.
$R_t$ 6.35 min; purity >99.5%; >98.8% ee
Yield: 320 mg
$^1$H-NMR: see Example 68A
LC-MS (method 2): $R_t$=3.37 min; m/z=637 (M+H$^+$).

Example 70A

Methyl 4-[(3E)-2-[2-(4-cyanophenyl)ethyl]—{2-[(6-phenylhexyl)oxy]phenyl}but-3-en-1-yl]-benzoate

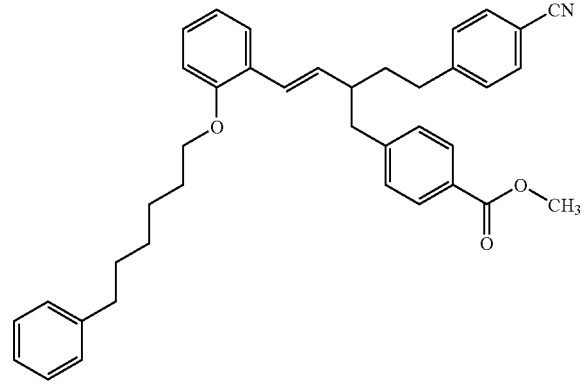 [SMILES: COC(=O)c1ccc(CC(/C=C/c2ccccc2OCCCCCCc2ccccc2)CCc2ccc(C#N)cc2)cc1]

A solution of 200 mg (0.49 mmol) of methyl 4-[(3E)-2-[2-(4-cyanophenyl)ethyl]-4-(2-hydroxyphenyl)but-3-en-1-yl]benzoate in 25 ml of acetonitrile is mixed with 176 mg (0.73 mmol) of (6-bromohexyl)benzene and 101 mg (0.73 mmol) of potassium carbonate and then stirred under reflux for 12 h. After cooling, the potassium carbonate is filtered off and the filtrate is evaporated. 364 mg (0.48 mmol, 98% of theory, purity 76%) of a yellowish oil are obtained.

LC-MS (method 2): $R_t$=3.47 min; MS (ESIpos): m/z=572 (M+H$^+$).

Example 71A

Diallyl {2-[4-(methoxycarbonyl)phenyl]ethyl}malonate

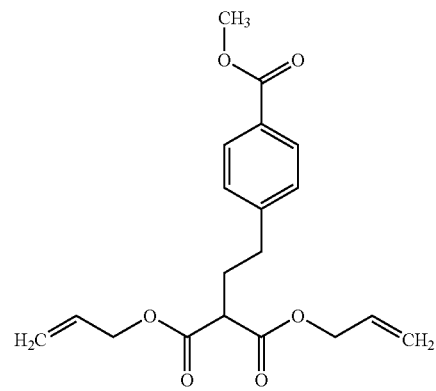 [SMILES: C=CCOC(=O)C(CCc1ccc(C(=O)OC)cc1)C(=O)OCC=C]

1.125 g (28.14 mmol) of sodium hydride are added in portions to a solution of 6.91 g (37.52 mmol) of diallyl malonate in 50 ml of dioxane at 0° C. (caution: evolution of hydrogen). After warming to room temperature, the mixture is stirred at 40° C. for 1 h. Then 4.56 g (18.76 mmol) of methyl 4-(2-bromoethyl)benzoate [CAS Reg. No. 136333-97-6], dissolved in 20 ml of dioxane, are slowly added dropwise at 40° C., and the reaction solution is stirred at 110° C. overnight. After cooling to room temperature, the reaction mixture is added to 1200 ml of water. Care must be taken during this that the pH remains <7 (if necessary, a few ml of 1 M hydrochloric acid are metered in until the pH is about 2). The mixture is then extracted three times with ethyl acetate, and the combined organic phases are washed with saturated sodium chloride solution and dried over sodium sulphate. After filtration, the solvent is evaporated to dryness in vacuo. Subsequently, excess diallyl malonate is removed by high vacuum distillation (boiling point: 57° C., 0.074 mbar). The distillation residue is purified by flash chromatography on silica gel (mobile phase: petroleum ether/ethyl acetate 10:1). 6.01 g (17.35 mmol, 92% of theory) of a colourless solid are obtained.

LC-MS (method 7): $R_t$=2.75 min; m/z=347 (M+H)$^+$.

Example 72A

Methyl 4-[(4E)-5-[2-(4-bromobutoxy)phenyl]-3-(4-cyanobenzyl)pent-4-en-1-yl]benzoate

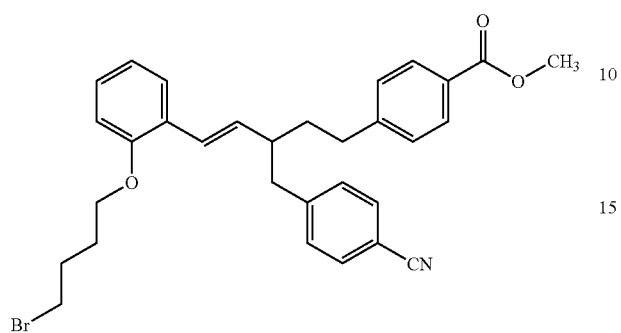

A solution of 664 mg (1.62 mmol) of methyl E-4-[3-(4-cyanobenzyl)-5-(2-hydroxyphenyl)pent-4-enyl]benzoate (enantiomer 1, Example 51A) in 28 ml of dry acetonitrile is mixed with 1743 mg (8.07 mmol) of 1,4-dibromobutane and 446 mg (3.23 mmol) of anhydrous potassium carbonate and then heated under reflux for 12 h. The mixture is subsequently filtered, and the filtrate is evaporated to dryness. The residue is purified by chromatography on silica gel (mobile phase: cyclohexane/ethyl acetate 10:1). 790 mg (1.44 mmol, 89% of theory) of a colourless oil are isolated.

$^1$H-NMR (400 MHz, CDCl$_3$, δ/ppm): 7.95 (2H, d), 7.53 (2H, d), 7.36 (1H, d), 7.29-7.14 (5H, m), 6.91 (1H, t), 6.83 (1H, d), 6.54 (1H, d), 6.01-5.91 (1H, m), 4.05-3.95 (2H, m), 3.91 (3H, s), 3.47 (2H, t), 2.89-2.72 (2H, m), 2.70-2.58 (1H, m), 2.54-2.42 (1H, m), 2.09-1.90 (4H, m), 1.89-1.79 (1H, m), 1.78-1.59 (2H, m).

LC-MS (method 7): $R_t$=3.40 min; m/z=547 (M+H)$^+$.

Example 73A

Methyl 4-[(4E)-3-(4-cyanobenzyl)-5-(2-{4-[4-(trifluoromethyl)phenoxy]butoxy}phenyl)pent-4-en-1-yl]benzoate

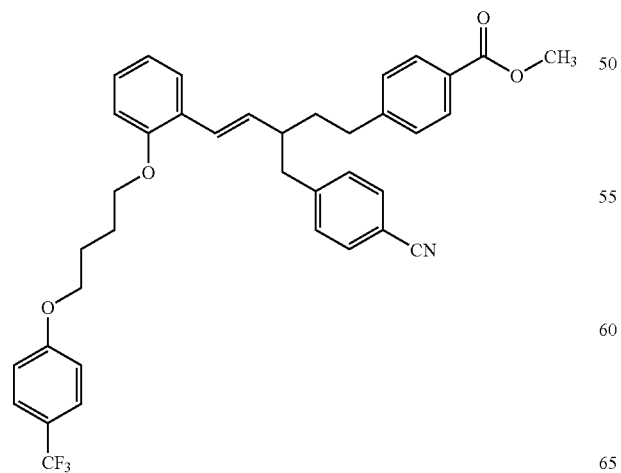

A solution of 392 mg (0.72 mmol) of methyl 4-[(4E)-5-[2-(4-bromobutoxy)phenyl]-3-(4-cyanobenzyl)pent-4-en-1-yl]benzoate in 10 ml of dry acetonitrile is mixed with 174 mg (1.08 mmol) of 4-trifluoromethylphenol and 148 mg (1.08 mmol) of anhydrous potassium carbonate and then heated under reflux for 12 h. The mixture is subsequently filtered, and the filtrate is evaporated to dryness. 450 mg (0.61 mmol, purity 86%, 86% of theory) of a yellowish oil are isolated.

LC-MS (method 2): $R_t$=3.38 min; m/z=628 (M+H)$^+$.

Example 74A

Methyl 4-[(4E)-3-(4-cyanobenzyl)-5-{2-[4-(4-fluorophenoxy)butoxy]phenyl}pent-4-en-1-yl]benzoate

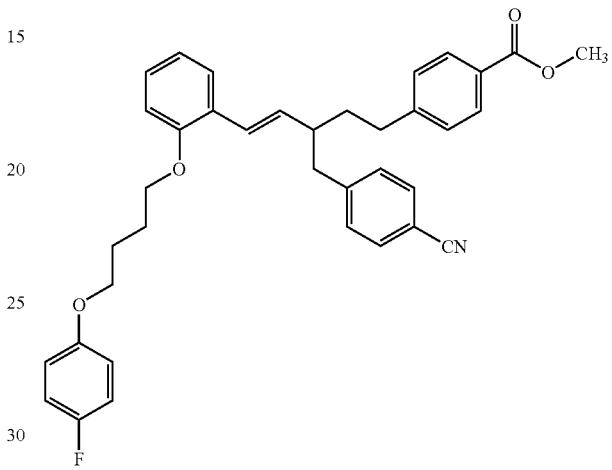

A solution of 392 mg (0.72 mmol) of methyl 4-[(4E)-5-[2-(4-bromobutoxy)phenyl]-3-(4-cyanobenzyl)pent-4-en-1-yl]benzoate in 10 ml of dry acetonitrile is mixed with 120 mg (1.08 mmol) of 4-fluorophenol and 148 mg (1.08 mmol) of anhydrous potassium carbonate and then heated under reflux for 12 h. The mixture is subsequently filtered, and the filtrate is evaporated to dryness. 445 mg (0.71 mmol, purity 93%, 99% of theory) of a yellowish oil are isolated.

LC-MS (method 2): $R_t$=3.33 min; m/z=578 (M+H)$^+$.

EXEMPLARY EMBODIMENTS

Example 1

4-[(4E)-5-{2-[(4-tert-Butylbenzyl)oxy]phenyl}-3-(4-carboxybenzyl)pent-4-en-1-yl]benzoic Acid (Racemate)

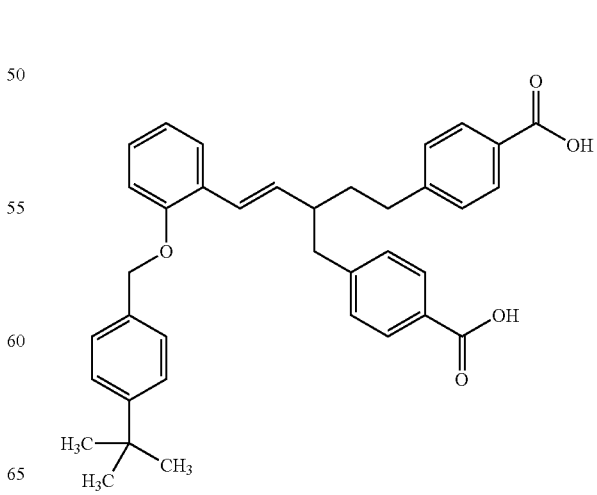

A solution of 430 mg (0.77 mmol) of methyl 4-{(3E)₄-{2-[(4-tert-butylbenzyl)oxy]phenyl}-2-[2-(4-cyanophenyl)ethyl]but-3-en-1-yl}benzoate in 20 ml of 1-propanol is mixed with 1.73 g (30.84 mmol) of potassium hydroxide and stirred at 110° C. for 5 hours. The mixture is adjusted to pH 2 with 1 M hydrochloric acid and evaporated. The resulting residue is purified directly by preparative HPLC. 290 mg (0.52 mmol, 53% yield) of the title compound are obtained.

¹H-NMR (400 MHz, DMSO-d₆, δ/ppm): 12.78 (2H, broad), 7.8 (4H, d), 7.4 (1H, d), 7.38 (2H, d), 7.32-7.21 (6H, m), 7.18 (1H, t), 7.05 (1H, d), 6.91 (1H, t), 6.5 (1H, d), 6.12 (1H, dd), 5.05 (2H, s), 2.89-2.81 (1H, m), 2.78-2.67 (2H, m), 2.67-2.56 (1H, m), 2.56-2.5 (1H, m), 1.86-1.72 (1H, m), 1.72-1.59 (1H, m), 1.25 (9H, s).

290 mg (0.52 mmol) of the racemic 4-[(4E)-5-{2-[(4-tert-butylbenzyl)oxy]phenyl}-3-(4-carboxybenzyl)pent-4-en-1-yl]benzoic Acid obtained in this way are further fractionated by preparative HPLC on a chiral phase. Respectively 90 mg and 102 mg of the two E-isomers are obtained in each case enantiopure as colourless solids (see Examples 2 and 3).

Example 2

4-[(4E)-5-{2-[(4-tert-Butylbenzyl)oxy]phenyl}-3-(4-carboxybenzyl)pent-4-en-1-yl]benzoic Acid (Enantiomer 1)

Enantiomer Separation Method:
Column: Daicel Chiralpak AD-H 250 mm×20 mm; eluent: isohexane (with 1% water and 0.2% acetic acid)/isopropanol 70:30 (v/v); flow rate: 15 ml/min; UV detection: 220 nm; temperature: 25° C.
R$_t$ 8.84 min; purity 99%; >99% ee
Yield: 90 mg
LC-MS (method 4): R$_t$ 2.89 min; MS (ESIpos): m/z 563 (M+H)⁺.

Example 3

4-[(4E)-5-{2-[(4-tert-Butylbenzyl)oxy]phenyl}-3-(4-carboxybenzyl)pent-4-en-1-yl]benzoic Acid (Enantiomer 2)

Enantiomer separation method: see Example 2.
R$_t$ 9.71 min; purity 99%; >98.5% ee
Yield: 102 mg
LC-MS (method 4): R$_t$=2.89 min; MS (ESIpos): m/z 563 (M+H)⁺.

Example 4

4-((4E)-3-(4-Carboxybenzyl)-5-{2-[(5-phenylpentyl)oxy]phenyl}pent-4-en-1-yl)benzoic Acid (Racemate)

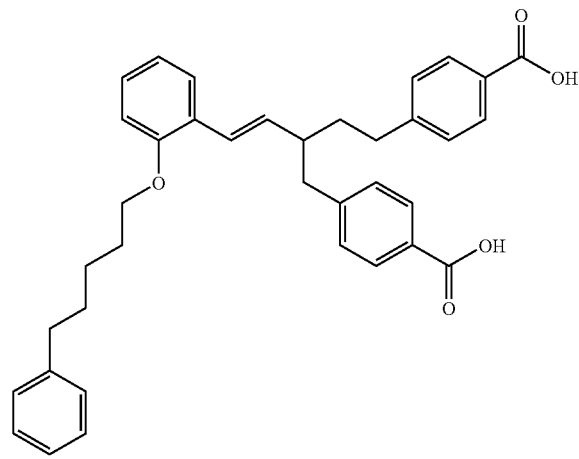 [SMILES: O=C(O)c1ccc(CCC(/C=C/c2ccccc2OCCCCCc2ccccc2)Cc2ccc(C(=O)O)cc2)cc1]

A solution of 600 mg (1.08 mmol) of methyl 4-((3E)-2-[2-(4-cyanophenyl)ethyl]-4-{2-[(5-phenylpentyl)oxy]phenyl}but-3-en-1-yl)benzoate in 15 ml of 1-propanol is mixed with 2.4 g (43 mmol) of potassium hydroxide and stirred at 110° C. for 7 hours. The mixture is adjusted to pH 2 with 1 M hydrochloric acid and evaporated. The resulting residue is directly purified by preparative HPLC. 235 mg (0.42 mmol, 38% yield) of the title compound are obtained as a colourless solid.

¹H-NMR (300 MHz, DMSO-d₆, δ/ppm): 12.8 (2H, broad), 7.88-7.78 (4H, m), 7.39 (1H, d), 7.32-7.1 (10H, m), 6.98-6.82 (2H, m), 6.41 (1H, d), 6.1 (1H, dd), 3.97-3.82 (2H, m), 2.9-2.8 (1H, m), 2.8-2.69 (2H, m), 2.69-2.58 (1H, m), 1.88-1.52 (9H, m), 1.46-1.32 (2H, m). 235 mg (0.42 mmol) of the racemic 4-((4E)-3-(4-carboxybenzyl)-5-{2-[(5-phenylpentyl)oxy]phenyl}pent-4-en-1-yl)benzoic Acid obtained in this way are further fractionated by preparative HPLC on a chiral phase. Respectively 90 mg and 91 mg of the two E-isomers are obtained in each case enantiopure as colourless solids (see Examples 5 and 6).

Example 5

4-((4E)-3-(4-Carboxybenzyl)-5-{2-[(5-phenylpentyl)oxy]phenyl}pent-4-en-1-yl)benzoic Acid (Enantiomer 1)

Enantiomer Separation Method:
Column: Daicel Chiralpak AD-H 250 mm×20 mm; eluent: isohexane (with 1% water and 0.2% acetic acid)/isopropanol 70:30 (v/v); flow rate: 15 ml/min; UV detection: 220 nm; temperature: 27° C.
R$_t$ 6.93 min; purity 97.5%; >99.5% ee
Yield: 90 mg.

Example 6

4-((4E)-3-(4-Carboxybenzyl)-5-{2-[(5-phenylpentyl)oxy]phenyl}pent-4-en-1-yl)benzoic Acid (Enantiomer 2)

Enantiomer separation method: see Example 5.
R$_t$ 8.43 min; purity 99.5%; >99.5% ee
Yield: 91 mg.

Example 7

4-[(4E)-3-(4-Carboxybenzyl)-5-(2-{[4-(2-phenylethyl)benzyl]oxy}phenyl)pent-4-en-1-yl]benzoic acid (Racemate)

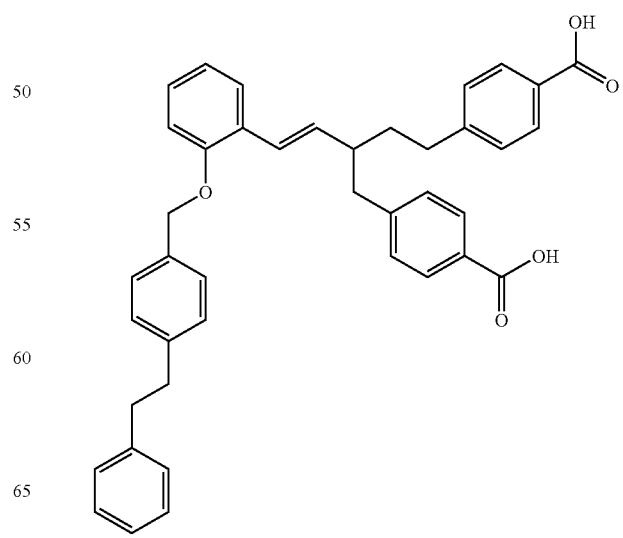

A solution of 400 mg (0.66 mmol) of methyl 4-[(3E)-2-[2-(4-cyanophenyl)ethyl]-4-(2-{[4-(2-phenylethyl)benzyl]oxy}phenyl)but-3-en-1-yl]benzoate in 20 ml of 1-propanol is mixed with 1.48 g (26.4 mmol) of potassium hydroxide and stirred at 110° C. for 5 hours. The mixture is adjusted to pH 2 with 1 M hydrochloric acid and evaporated. The resulting residue is directly purified by preparative HPLC. 280 mg (0.46 mmol, 58% yield) of the title compound are obtained as a colourless solid.

$^1$H-NMR (300 MHz, DMSO-$d_6$, δ/ppm): 12.79 (2H, broad), 7.82 (4H, d), 7.42 (1H, d), 7.31-7.12 (14H, m), 7.03 (1H, d), 6.9 (1H, t), 6.49 (1H, d), 6.12 (1H, dd), 5.05 (2H, s), 2.9-2.78 (3H, m), 2.78-2.67 (2H, m), 1.87-1.58 (2H, m).

280 mg (0.46 mmol) of the racemic 4-[(4E)-3-(4-carboxybenzyl)-5-(2-{[4-(2-phenylethyl)-benzyl]oxy}phenyl)pent-4-en-1-yl]benzoic Acid obtained in this way are further fractionated by preparative HPLC on a chiral phase. Respectively 111 mg and 123 mg of the two E-isomers are obtained in each case enantiopure as colourless solids (see Examples 8 and 9).

Example 8

4-[(4E)-3-(4-Carboxybenzyl)-5-(2-{[4-(2-phenylethyl)benzyl]oxy}phenyl)pent-4-en-1-yl]benzoic acid (Enantiomer 1)

Enantiomer Separation Method:
Column: Daicel Chiralpak AD-H 250 mm×20 mm; eluent: isohexane (with 1% water and 0.2% acetic acid)/isopropanol 70:30 (v/v); flow rate: 15 ml/min; UV detection: 220 nm; temperature: 25° C.
$R_t$ 8.40 min; purity 98.5%; >99.5% ee
Yield: 111 mg.

Example 9

4-[(4E)-3-(4-Carboxybenzyl)-5-(2-{[4-(2-phenylethyl)benzyl]oxy}phenyl)pent-4-en-1-yl]benzoic acid (Enantiomer 2)

Enantiomer separation method: see Example 8.
$R_t$ 10.19 min; purity 99%; >99.5% ee
Yield: 123 mg.

Example 10

4-[(4E/Z)-3-(4-Carboxybenzyl)-5-(2-{[4'-(trifluoromethyl)biphenyl-4-yl]methoxy}phenyl)pent-4-en-1-yl]benzoic Acid

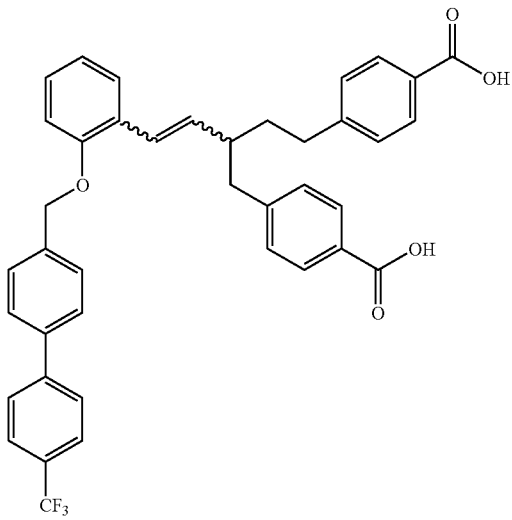 [SMILES: O=C(O)c1ccc(CCC(C=Cc2ccccc2OCc2ccc(-c3ccc(C(F)(F)F)cc3)cc2)Cc2ccc(C(=O)O)cc2)cc1]

A solution of 56 mg (0.08 mmol) of methyl 4-[(4E/Z)-3-[4-(methoxycarbonyl)benzyl]-5-(2-{[4'-(trifluoromethyl)biphenyl-4-yl]methoxy}phenyl)pent-4-en-1-yl]benzoate in 2 ml of water and 2 ml of THF is mixed with 4 mg (0.17 mmol) of lithium hydroxide and stirred at 50° C. for 12 hours. The mixture is diluted with water, adjusted to pH 5 with 1 M hydrochloric acid and extracted twice with ethyl acetate. The combined organic phases are dried over sodium sulphate and evaporated. 44.6 mg (0.07 mmol, 78% yield) of the title compound are obtained as a colourless solid.

$^1$H-NMR (300 MHz, DMSO-$d_6$, δ/ppm): 12.76 (2H, broad), 7.9-7.78 (8H, m), 7.78-7.6 (3H, m), 7.53-7.38 (3H, m), 7.3-7.14 (5H, m), 6.92 (1H, t), 6.5 (1H, d), 6.12 (1H, dd), 5.18 (2H, s), 2.9-2.58 (5H, m), 1.88-1.55 (2H, m).

Example 11

4-{(4E)-3-(4-Carboxybenzyl)-5-[2-(4,4,4-trifluorobutoxy)phenyl]pent-4-en-1-yl}benzoic Acid (Racemate)

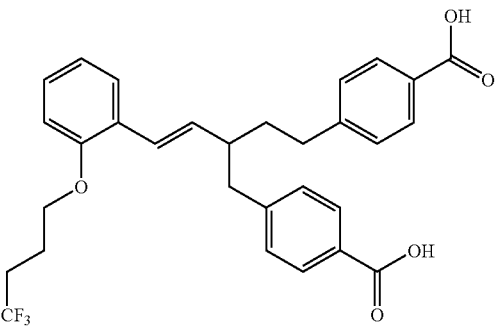

A solution of 265 mg (0.51 mmol) of methyl 4-{(3E)-2-[2-(4-cyanophenyl)ethyl]-4-[2-(4,4,4-trifluorobutoxy)phenyl]but-3-en-1-yl}benzoate in 15 ml of 1-propanol is mixed with 1.14 g (20.3 mmol) of potassium hydroxide and stirred at 110° C. for 12 h. After cooling, the mixture is acidified with 1 M hydrochloric acid, and the crystals which have separated out are filtered off with suction and dried. 250 mg (0.47 mmol, 93% of theory) of the title compound are obtained.

LC-MS (method 2): $R_t$=2.63 min; MS (ESIpos): m/z=527 (M+H)$^+$.

Example 12

4-[(4E)-3-(4-Carboxybenzyl)-5-(2-methoxyphenyl)pent-4-en-1-yl]benzoic Acid (Racemate)

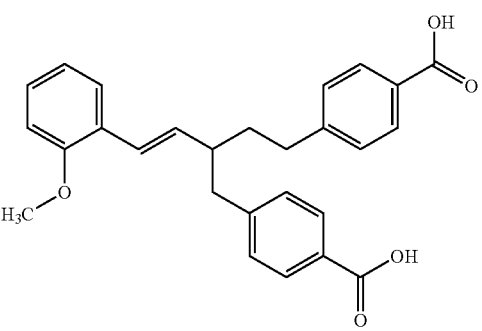 [SMILES: COc1ccccc1/C=C/C(CCc1ccc(C(=O)O)cc1)Cc1ccc(C(=O)O)cc1]

654 mg (1.5 mmol, 99% of theory) of the title compound are obtained by the process described in Example 11 starting from 632 mg (1.54 mmol) of 4-[(3E)-2-[2-(4-cyanophenyl)ethyl]-4-(2-methoxyphenyl)but-3-en-1-yl]benzoic Acid and 3.45 g (61.4 mmol) of potassium hydroxide.

LC-MS (method 4): $R_t$=2.58 min; MS (ESIpos): m/z=431 (M+H)+.

163 mg (0.34 mmol) of the racemic 4-[(4E)-3-(4-carboxybenzyl)-5-(2-methoxyphenyl)pent-4-en-1-yl]benzoic Acid obtained in this way are further fractionated by preparative HPLC on a chiral phase. Respectively 69 mg and 49 mg of the two E-isomers are obtained in each case enantiopure (see Examples 13 and 14).

Example 13

4-[(4E)-3-(4-Carboxybenzyl)-5-(2-methoxyphenyl)pent-4-en-1-yl]benzoic Acid (Enantiomer 1)

Enantiomer Separation Method:
Column: Daicel Chiralcel OD-H 250 mm×20 mm; eluent: isopropanol (with 1% water and 0.2% trifluoroacetic acid)/isohexane 30:70 (v/v); flow rate: 15 ml/min; uV detection: 220 nm; temperature: 30° C.

$R_t$ 5.97 min; purity >99%; >99% ee
Yield: 69 mg
LC-MS (method 3): $R_t$=2.63 min; MS (ESIpos): m/z=431 (M+H)+

$^1$H-NMR (400 MHz, DMSO-$d_6$, δ/ppm): 12.89-12.69 (2H, broad), 7.89-7.78 (4H, m), 7.42 (1H, d), 7.30 (4H, d), 7.20 (1H, t), 6.95 (1H, d), 6.90 (1H, t), 6.46 (1H, d), 6.15-6.02 (1H, m), 3.76 (3H, s), 2.94-2.81 (1H, m), 2.80-2.54 (4H, m), 1.85-1.72 (1H, m), 1.71-1.59 (1H, m).

Example 14

4-[(4E)-3-(4-Carboxybenzyl)-5-(2-methoxyphenyl)pent-4-en-1-yl]benzoic Acid (Enantiomer 2)

Enantiomer separation method: see Example 13.
$R_t$ 6.98 min; purity >99%; >98% ee
Yield: 49 mg.

Example 15

4-[(4E)-5-(2-Butoxyphenyl)-3-(4-carboxybenzyl)pent-4-en-1-yl]benzoic Acid (Racemate)

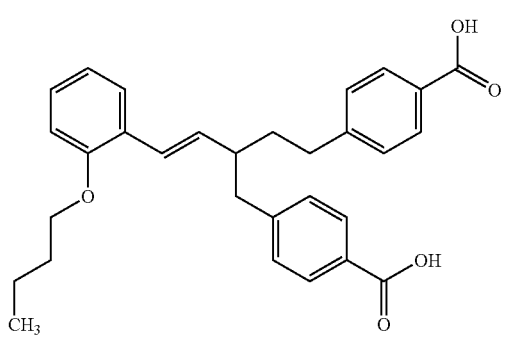 [SMILES: CCCCOc1ccccc1/C=C/C(CCc1ccc(C(=O)O)cc1)Cc1ccc(C(=O)O)cc1]

169 mg (0.36 mmol, 76% of theory) of the title compound are obtained by the process described in Example 11 starting from 220 mg (0.47 mmol) of methyl 4-{(3E)-4-(2-butoxyphenyl)-2-[2-(4-cyanophenyl)ethyl]but-3-en-1-yl}benzoate and 1 g (18.8 mmol) of potassium hydroxide.

LC-MS (method 2): $R_t$=2.72 min; MS (ESIpos): m/z=472 (M+H)+

$^1$H-NMR (400 MHz, DMSO-$d_6$, δ/ppm): 12.75 (s, 2H), 7.9-7.75 (m, 4H), 7.4 (d, 1H), 7.28 (t, 4H), 7.16 (t, 1H), 6.95-6.83 (m, 2H), 6.42 (d, 1H), 6.1 (dd, 1H), 3.98-3.85 (m, 2H), 2.92-2.82 (m, 1H), 2.8-2.4 (m, 5H), 1.88-1.75 (m, 1H), 1.75-1.6 (m, 3H), 1.45-1.32 (m, 2H), 0.9 (t, 3H).

Example 16

4-{(4E)-3-(4-Carboxybenzyl)-5-[2-(pentyloxy)phenyl]pent-4-en-1-yl}benzoic Acid (Racemate)

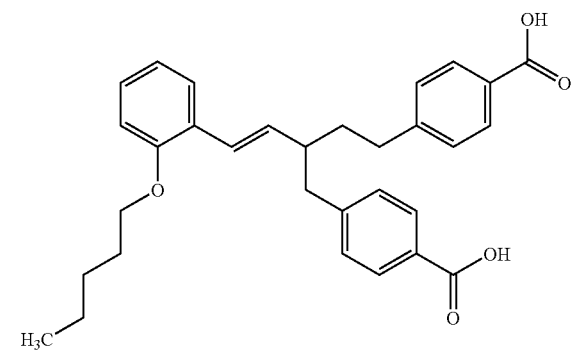

160 mg (0.33 mmol, 74% of theory) of the title compound are obtained by the process described in Example 11 starting from 195 mg (0.41 mmol) of methyl 4-{(3E)-2-[2-(4-cyanophenyl)ethyl]-4-[2-(pentyloxy)phenyl]but-3-en-1-yl}benzoate and 909 mg (16.2 mmol) of potassium hydroxide.

LC-MS (method 1): $R_t$=3.09 min; MS (ESIpos): m/z=486 (M+H)+

$^1$H-NMR (400 MHz, DMSO-$d_6$, δ/ppm): 12.75 (s, 2H), 7.9-7.86 (m, 4H), 7.38 (d, 1H), 7.3-7.25 (m, 4H), 7.15 (t, 1H), 6.95-6.83 (m, 2H), 6.44 (d, 1H), 6.1 (dd, 1H), 3.98-3.84 (m, 2H), 2.92-2.81 (m, 1H), 2.8-2.58 (m, 3H), 2.58-2.43 (m, 2H), 1.88-1.75 (m, 1H), 1.75-1.6 (m, 3H), 1.4-1.22 (m, 3H), 0.84 (t, 3H).

160 mg (0.33 mmol) of the racemic 4-{(4E)-3-(4-carboxybenzyl)-5-[2-(pentyloxy)phenyl]pent-4-en-1-yl}benzoic acid obtained in this way are further fractionated by preparative HPLC on a chiral phase. Respectively 55 mg and 49 mg of the two E-isomers are obtained in each case enantiopure (see Examples 17 and 18).

Example 17

4-{(4E)-3-(4-Carboxybenzyl)-5-[2-(pentyloxy)phenyl]pent-4-en-1-yl}benzoic Acid (Enantiomer 1)

Enantiomer Separation Method:
Column: Daicel Chiralpak AD-H 250 mm×20 mm; eluent: isopropanol (with 1% water and 0.2% trifluoroacetic acid)/isohexane 25:75 (v/v); flow rate: 15 ml/min; UV detection: 220 nm; temperature: 30° C.

$R_t$ 6.57 mm; purity >94.5%; >99% ee
Yield: 55 mg.

Example 18

4-{(4E)-3-(4-Carboxybenzyl)-5-[2-(pentyloxy)phenyl]pent-4-en-1-yl}benzoic Acid (Enantiomer 2)

Enantiomer separation method: see Example 17.
$R_t$ 7.41 min; purity >99%; >97% ee
Yield: 49 mg.

Example 19

4-{(4E)-3-(4-Carboxybenzyl)-5-[2-(hexyloxy)phenyl]pent-4-en-1-yl}benzoic Acid (Racemate)

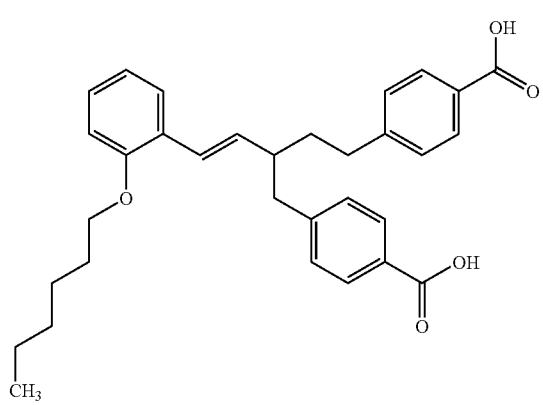 [SMILES: CCCCCCOc1ccccc1/C=C/C(CCc1ccc(C(=O)O)cc1)Cc1ccc(C(=O)O)cc1]

159 mg (0.32 mmol, 83% of theory) of the title compound are obtained by the process described in Example 11 starting from 190 mg (0.38 mmol) of methyl 4-{(3E)-2-[2-(4-cyanophenyl)ethyl]-4-[2-(hexyloxy)phenyl]but-3-en-1-yl}benzoate and 860 mg (15.3 mmol) of potassium hydroxide.

LC-MS (method 6): $R_t$=6.66 min; MS (ESIpos): m/z=501 (M+H)+

$^1$H-NMR (400 MHz, DMSO-$d_6$, δ/ppm): 12.76 (s, 2H), 7.9-7.77 (m, 4H), 7.38 (d, 1H), 7.32-7.23 (m, 4H), 7.16 (t, 1H), 6.94-6.85 (m, 2H), 6.44 (d, 1H), 6.11 (dd, 1H), 3.97-3.84 (m, 2H), 2.91-2.82 (m, 1H), 2.79-2.42 (m, 5H), 1.87-1.74 (m, 1H), 1.74-1.6 (m, 3H), 1.44-1.17 (m, 5H), 0.82 (t, 3H). 159 mg (0.32 mmol) of the racemic 4-{(4E)-3-(4-carboxybenzyl)-5-[2-(hexyloxy)phenyl]pent-4-en-1-yl}benzoic acid obtained in this way are further fractionated by preparative HPLC on a chiral phase. Respectively 56 mg and 46 mg of the two E-isomers are obtained in each case enantiopure (see Examples 20 and 21).

Example 20

4-{(4E)-3-(4-Carboxybenzyl)-5-[2-(hexyloxy)phenyl]pent-4-en-1-yl}benzoic Acid (Enantiomer 1)

Enantiomer Separation Method

Column: Daicel Chiralpak AD-H 250 mm×20 mm; eluent: isopropanol (with 1% water and 0.2% trifluoroacetic acid)/isohexane 25:75 (v/v); flow rate: 15 ml/min; UV detection: 220 nm; temperature: 30° C.

$R_t$ 6.05 min; purity >97%; >99% ee
Yield: 56 mg.

Example 21

4-{(4E)-3-(4-Carboxybenzyl)-5-[2-(hexyloxy)phenyl]pent-4-en-1-yl}benzoic Acid (Enantiomer 2)

Enantiomer separation method: see Example 20.
$R_t$ 6.8 min; purity >98.5%; >99% ee
Yield: 46 mg.

Example 22

4-{(4E)-3-(4-Carboxybenzyl)-5-[2-(heptyloxy)phenyl]pent-4-en-1-yl}benzoic Acid (Racemate)

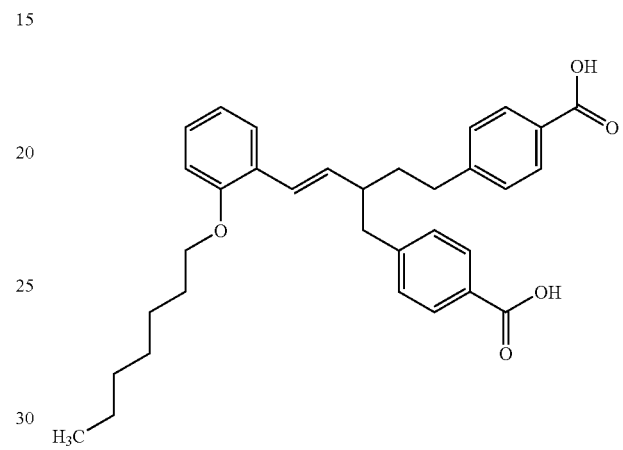

190 mg (0.37 mmol, 99% of theory) of the title compound are obtained by the process described in Example 11 starting from 190 mg (0.37 mmol) of methyl 4-{(3E)-2-[2-(4-cyanophenyl)ethyl]-4-[2-(heptyloxy)phenyl]but-3-en-1-yl}benzoate and 837 mg (14.9 mmol) of potassium hydroxide.

LC-MS (method 1): $R_t$=3.3 min; MS (ESIpos): m/z=515 (M+H)+

$^1$H-NMR (400 MHz, DMSO-$d_6$, δ/ppm): 12.75 (s, 2H), 7.9-7.75 (m, 4H), 7.38 (d, 1H), 7.32-7.2 (m, 4H), 7.17 (t, 1H), 6.95-6.82 (m, 2H), 6.45 (d, 1H), 6.12 (dd, 1H), 3.98-3.85 (m, 2H), 2.9-2.8 (m, 1H), 2.8-2.4 (m, 4H), 1.88-1.75 (m, 1H), 1.75-1.6 (m, 3H), 1.42-1.12 (m, 8H), 0.8 (t, 3H).

Example 23

4-[(4E/Z)-3-(4-Carboxybenzyl)-5-phenylpent-4-en-1-yl]benzoic Acid (Racemate)

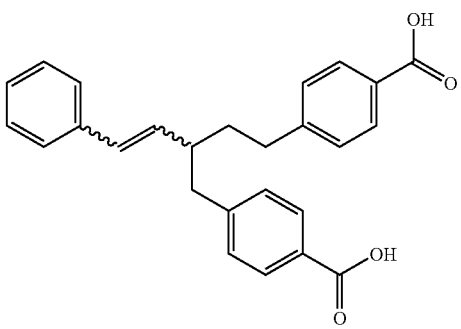 [SMILES: O=C(O)c1ccc(CCC(C=Cc2ccccc2)Cc2ccc(C(=O)O)cc2)cc1]

453 mg (1.13 mmol, 92% of theory) of the title compound are obtained by the process described in Example 11 starting from 484 mg (1.22 mmol) of methyl 4-{(3E/Z)-2-[2-(4-cyanophenyl)ethyl]-4-phenylbut-3-en-1-yl}benzoate and 2.75 g (48.95 mmol) of potassium hydroxide.

LC-MS (method 1): $R_t$=2.88 min; MS (ESIpos): m/z=485 (M+H)$^+$.

450 mg (1.12 mmol) of the racemic 4-[(4E/Z)-3-(4-carboxybenzyl)-5-phenylpentn-1-yl]benzoic acid obtained in this way are further fractionated by preparative HPLC on a chiral phase. Respectively 123 mg and 127 mg of the two E-isomers are obtained in each case enantiopure (see Examples 24 and 25).

Example 24

4-[(4E)-3-(4-Carboxybenzyl)-5-phenylpent-4-en-1-yl]benzoic Acid (Enantiomer 1)

Enantiomer Separation Method:
Column: Daicel Chiralcel OD-H 250 mm×20 mm; eluent: isopropanol (with 1% water and 0.2% trifluoroacetic acid)/isohexane 50:50 (v/v); flow rate: 15 ml/min; UV detection: 220 nm; temperature: 40° C.
$R_t$ 21.37 min; purity >99.5%; >99% ee
Yield: 123 mg
$^1$H-NMR (400 MHz, DMSO-d$_6$, δ/ppm): 12.75 (br. s, 2H), 7.82 (t, 4H), 7.38-7.23 (m, 8H), 7.19 (t, 1H), 6.3-6.12 (m, 2H), 2.92-2.82 (m, 1H), 2.8-2.55 (m, 4H), 1.85-1.62 (m, 2H).

Example 25

4-[(4E)-3-(4-Carboxybenzyl)-5-phenylpent-4-en-1-yl]benzoic Acid (Enantiomer 2)

Enantiomer separation method: see Example 24.
$R_t$ 25.6 min; purity >99.5%; >99% ee
Yield: 127 mg.

Example 26

4-{(4E/Z)-3-(4-Carboxybenzyl)-5-[2-(trifluoromethoxy)phenyl]pent-4-en-1-yl}benzoic Acid (Racemate)

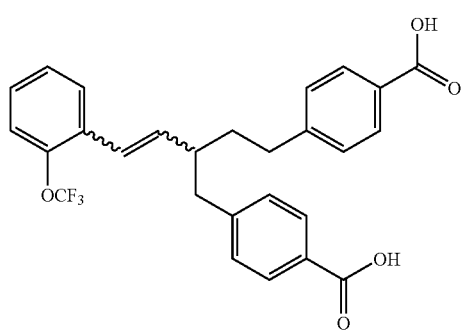 [SMILES: O=C(O)c1ccc(CCC(C=Cc2ccccc2OC(F)(F)F)Cc2ccc(C(=O)O)cc2)cc1]

440 mg (0.91 mmol, 87% of theory) of the title compound are obtained by the process described in Example 11 starting from 500 mg (1.043 mmol) of methyl 4-{(3E/Z)-2-[2-(4-cyanophenyl)ethyl]-4-[2-(trifluoromethoxy)phenyl]but-3-en-1-yl}benzoate and 2.34 g (41.7 mmol) of potassium hydroxide.

LC-MS (method 1): $R_t$=2.73 min; MS (ESIpos): m/z=485 (M+H)$^+$ 440 mg (0.91 mmol) of the racemic 4-{(4E/Z)-3-(4-carboxybenzyl)-5-[2-(trifluoromethoxy)phenyl]pent-4-en-1-yl}benzoic acid obtained in this way are further fractionated by preparative HPLC on a chiral phase. Respectively 108 mg and 107 mg of the two E-isomers are obtained in each case enantiopure (see Examples 27 and 28).

Example 27

4-{(4E)-3-(4-Carboxybenzyl)-5-[2-(trifluoromethoxy)phenyl]pent-4-en-1-yl}benzoic Acid (Enantiomer 1)

Enantiomer Separation Method:
Column: Daicel Chiralpak AD-H 250 mm×20 mm; eluent: isopropanol (with 1% water and 0.2% trifluoroacetic acid)/isohexane 25:75 (v/v); flow rate: 15 mlmin; UV detection: 220 nm; temperature: 29° C.
$R_t$ 5.85 min; purity >98.8%; >99% ee
Yield: 108 mg
$^1$H-NMR (400 MHz, DMSO-d$_6$, δ/ppm): 12.8 (br. s, 2H), 7.88-7.8 (m, 4H), 7.7-7.65 (m, 1H), 7.39-7.32 (m, 2H), 7.29 (d, 5H), 6.37-6.21 (m, 2H), 2.9 (dd, 1H), 2.8-2.54 (m, 4H), 1.89-1.65 (m, 2H).

Example 28

4-{(4E)-3-(4-Carboxybenzyl)-5-[2-(trifluoromethoxy)phenyl]pent-4-en-1-yl}benzoic Acid (Enantiomer 2)

Enantiomer separation method: see Example 27.
$R_t$ 6.78 min; purity >99.5%; >98% ee
Yield: 107 mg.

Example 29

4-[(4E)-3-(4-Carboxybenzyl)-5-(2-propoxyphenyl)pent-4-en-1-yl]benzoic Acid (Racemate)

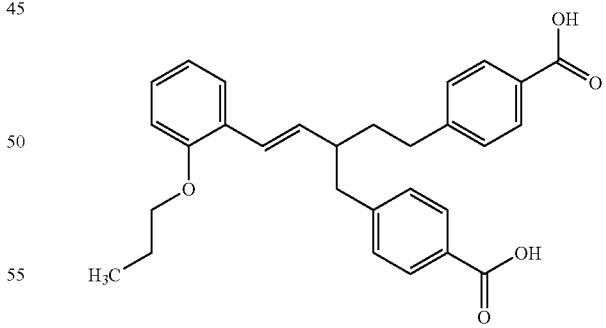

21 mg (0.05 mmol, 10% of theory) of the title compound are obtained by the process described in Example 11 starting from 200 mg (0.44 mmol) of methyl 4-[(3E)-2-[2-(4-cyanophenyl)ethyl]-4-(2-propoxyphenyl)but-3-en-1-yl]benzoate and 989.5 mg (17.6 mmol) of potassium hydroxide.

LC-MS (method 1): $R_t$=2.87 min; MS (ESIpos): m/z=459 (M+H)$^+$.

11 mg (0.02 mmol) of the racemic 4-[(4E)-3-(4-carboxybenzyl)-5-(2-propoxyphenyl)pent-4-en-1-yl]benzoic Acid obtained in this way are further fractionated by preparative HPLC on a chiral phase. Respectively 6 mg and 4 mg of the two E-isomers are obtained in each case enantiopure (see Examples 30 and 31).

Example 30

4-[(4E)-3-(4-Carboxybenzyl)-5-(2-propoxyphenyl)pent-4-en-1-yl]benzoic Acid (Enantiomer 1)

Enantiomer Separation Method:
Column: Daicel Chiralpak AD-H 250 mm×20 mm, 5 µm; eluent: isopropanol (with 1% water and 0.2% trifluoroacetic acid)/isohexane 28:72 (v/v); flow rate: 15 ml/min; UV detection: 220 nm; temperature: 25° C.
$R_t$ 8.27 min; purity >97%; >99% ee
Yield: 6 mg
LC-MS (method 1): $R_t$=2.87 min; MS (ESIpos): m/z=459 (M+H)$^+$.

Example 31

4-[(4E)-3-(4-Carboxybenzyl)-5-(2-propoxyphenyl)pent-4-en-1-yl]benzoic Acid (Enantiomer 2)

Enantiomer separation method: see Example 30.
$R_t$ 9.21 min; purity >94.5%; >99% ee
Yield: 4 mg
LC-MS (method 1): $R_t$=2.87 min; MS (ESIpos): m/z=459 (M+H)$^+$.

Example 32

4-[(4E)-3-(4-Carboxybenzyl)-5-(2-ethoxyphenyl)pent-4-en-1-yl]benzoic Acid (Racemate)

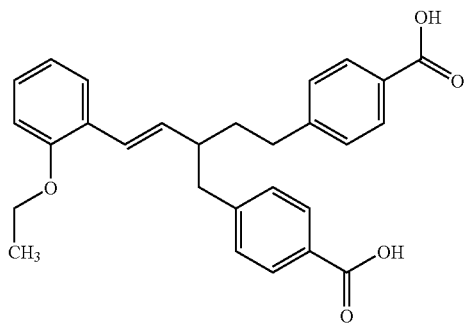 [SMILES: CCOc1ccccc1/C=C/C(CCc1ccc(C(=O)O)cc1)Cc1ccc(C(=O)O)cc1]

60 mg (0.13 mmol, 30% of theory) of the title compound are obtained by the process described in Example 11 starting from 195 mg (0.44 mmol) of methyl 4-[(3E)-2-[2-(4-cyanophenyl)ethyl]-4-(2-ethoxyphenyl)but-3-en-1-yl]benzoate and 995.6 mg (17.7 mmol) of potassium hydroxide.

LC-MS (method 1): $R_t$=2.76 min; MS (ESIpos): m/z=445 (M+H)$^+$.

52 mg (0.12 mmol) of the racemic 4-[(4E)-3-(4-carboxybenzyl)-5-(2-ethoxyphenyl)pent-4-en-1-yl]benzoic Acid obtained in this way are further fractionated by preparative HPLC on a chiral phase. Respectively 24 mg and 25 mg of the two E-isomers are obtained in each case enantiopure (see Examples 33 and 34).

Example 33

4-[(4E)-3-(4-Carboxybenzyl)-5-(2-ethoxyphenyl)pent-4-en-1-yl]benzoic Acid (Enantiomer 1)

Enantiomer Separation Method:
Column: Daicel Chiralpak AD-H 250 mm×20 mm, 5 µm; eluent: ethanol (with 1% water and 0.2% trifluoroacetic acid)/isohexane 20:80 (v/v); flow rate: 15 ml/min; UV detection: 220 nm; temperature: 25° C.
$R_t$ 8.28 min; purity >99.5%; >99.5% ee
Yield: 24 mg
$^1$H-NMR (400 MHz, DMSO-d$_6$, δ/ppm): 12.78 (br. s, 2H), 7.92-7.73 (m, 4H), 7.41 (d, 1H), 7.36-7.22 (m, 4H), 7.16 (t, 1H), 6.99-6.82 (m, 2H), 6.44 (d, 1H), 6.18-6.01 (m, 1H), 4.06-3.89 (m, 2H), 2.94-2.81 (m, 1H), 2.80-2.69 (m, 2H), 2.68-2.57 (m, 1H), 2.56-2.41 (m, 1H), 1.89-1.74 (m, 1H), 1.73-1.60 (m, 1H), 1.27 (t, 3H).
LC-MS (method 1): $R_t$=2.76 min; MS (ESIpos): m/z=445 (M+H)$^+$.

Example 34

4-[(4E)-3-(4-Carboxybenzyl)-5-(2-ethoxyphenyl)pent-4-en-1-yl]benzoic Acid (Enantiomer 2)

Enantiomer separation method: see Example 33.
$R_t$ 9.34 min; purity >99.5%; >99.5% ee
Yield: 25 mg
$^1$H-NMR: see Example 33
LC-MS (method 1): $R_t$=2.76 min; MS (ESIpos): m/z 445 (M+H)$^+$.

Example 35

4-{(4E)-3-(4-Carboxybenzyl)-5-[2-(3-phenylpropoxy)phenyl]pent-4-en-1-yl}benzoic Acid (Racemate)

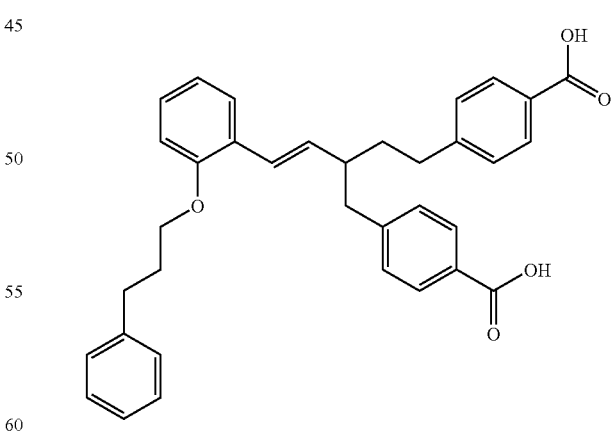

194 mg (0.34 mmol, purity 94%, 67% of theory) of the title compound are obtained by the process described in Example 11 starting from 270 mg (0.51 mmol) of methyl 4-{(3E)-2-[2-(4-cyanophenyl)ethyl]-4-[2-(3-phenylpropoxy)phenyl]but-3-en-1-yl}benzoate and 1143 mg (20.4 mmol) of potassium hydroxide.

$^1$H-NMR (400 MHz, DMSO-d$_6$, δ/ppm): 12.77 (br. s, 2H), 7.89-7.75 (4H, m), 7.40 (1H, d), 7.33-7.20 (6H, m), 7.19-7.10 (4H, m), 6.94-6.83 (2H, m), 6.49 (1H, d), 6.21-6.07 (1H, m), 3.98-3.82 (2H, m), 2.94-2.83 (1H, m), 2.82-2.58 (6H, m), 2.05-1.93 (2H, m), 1.89-1.75 (1H, m), 1.74-1.60 (1H, m).

LC-MS (method 4): R$_t$=3.02 min; MS (ESIpos): m/z=535 (M+H)$^+$.

190 mg (0.35 mmol) of the 4-{(4E)-3-(4-carboxybenzyl)-5-[2-(3-phenylpropoxy)phenyl]pent-4-en-1-yl}benzoic acid obtained in this way are further fractionated by preparative HPLC on a chiral phase. Respectively 93 mg and 90 mg of the two E-isomers are obtained in each case enantiopure (see Examples 36 and 37).

Example 36

4-{(4E)-3-(4-Carboxybenzyl)-5-[2-(3-phenylpropoxy)phenyl]pent-4-en-1-yl}benzoic Acid (Enantiomer 1)

Enantiomer Separation Method:
Column: Daicel Chiralpak AD 250 mm×20 mm; eluent: isopropanol (with 1% water and 0.2% trifluoroacetic acid)/isohexane 23:77 (v/v); flow rate: 15 ml/min; UV detection: 215 nm; temperature: 30° C.

R$_t$ 11.91 min; purity >99.5%; >99.5% ee
Yield: 93 mg
LC-MS (method 2): R$_t$=2.85 min; MS (ESIpos): m/z=535 (M+H)$^+$.

Example 37

4-{(4E)-3-(4-Carboxybenzyl)-5-[2-(3-phenylpropoxy)phenyl]pent-4-en-1-yl}benzoic Acid (Enantiomer 2)

Enantiomer separation method: see Example 36.
R$_t$ 14.72 min; purity >99.5%; >99.5% ee
Yield: 90 mg
LC-MS (method 2): R$_t$=2.85 min; MS (ESIpos): m/z=535 (M+H)$^+$.

Example 38

4-{(4E)-3-(4-Carboxybenzyl)-5-[2-(4-phenylbutoxy)phenyl]pent-4-en-1-yl}benzoic Acid (Racemate)

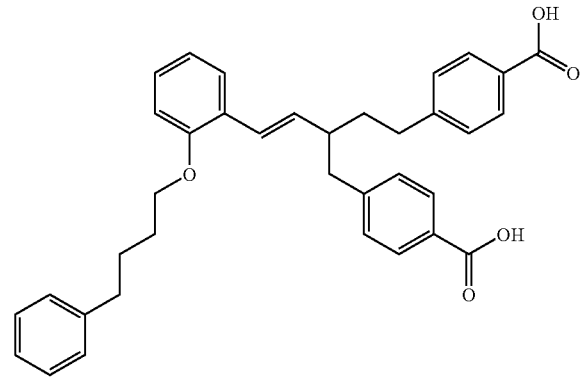 [SMILES: O=C(O)c1ccc(CCC(/C=C/c2ccccc2OCCCCc2ccccc2)Cc2ccc(C(=O)O)cc2)cc1]

74 mg (0.13 mmol, 24% of theory) of the title compound are obtained by the process described in Example 11 starting from 300 mg (0.55 mmol) of methyl 4-{(3E)-2-[2-(4-cyanophenyl)ethyl]-4-[2-(4-phenylbutoxy)phenyl]but-3-en-1-yl}benzoate and 1238 mg (22 mmol) of potassium hydroxide.

LC-MS (method 1): R$_t$=3.15 min; MS (ESIpos): m/z=549 (M+H)$^+$.

60 mg (0.11 mmol) of the 4-{(4E)-3-(4-carboxybenzyl)-5-[2-(4-phenylbutoxy)phenyl]pent-4-en-1-yl}benzoic acid obtained in this way are further fractionated by preparative HPLC on a chiral phase. Respectively 20 mg and 28 mg of the two E-isomers are obtained in each case enantiopure (see Examples 39 and 40).

Example 39

4-{(4E)-3-(4-Carboxybenzyl)-5-[2-(4-phenylbutoxy)phenyl]pent-4-en-1-yl}benzoic Acid (Enantiomer 1)

Enantiomer Separation Method:
Column: Daicel Chiralpak AD 250 mm×20 mm; eluent: isopropanol (with 1% water and 0.2% trifluoroacetic acid)/isohexane 23:77 (v/v); flow rate: 15 ml/min; UV detection: 215 nm; temperature: 30° C.

R$_t$ 11.36 min; >99.5% ee
Yield: 20 mg
$^1$H-NMR (400 MHz, DMSO-d$_6$, δ/ppm): 12.78 (br. s, 2H), 7.89-7.77 (4H, m), 7.39 (1H, d), 7.31-7.19 (6H, m), 7.19-7.09 (4H, m), 6.96-6.82 (2H, m), 6.44 (1H, d), 6.16-6.04 (1H, m), 4.02-3.87 (2H, m), 2.90-2.80 (1H, m), 2.78-2.66 (2H, m), 2.65-2.56 (3H, m), 2.55-2.41 (1H, m), 1.88-1.73 (1H, m), 1.72-1.58 (5H, m).

LC-MS (method 4): R$_t$=3.14 min; MS (ESIpos): m/z=549 (M+H)$^+$.

Example 40

4-{(4E)-3-(4-Carboxybenzyl)-5-[2-(4-phenylbutoxy)phenyl]pent-4-en-1-yl}benzoic Acid (Enantiomer 2)

Enantiomer separation method: see Example 39.
R$_t$ 13.29 min; >99.5% ee
Yield: 28 mg
$^1$H-NMR: see Example 39
LC-MS (method 4): R$_t$=3.14 min; MS (ESIpos): m/z=549 (M+H)$^+$.

Example 41

4-[(4E)-3-(4-Carboxybenzyl)-5-{2-[(5,5,5-trifluoropentyl)oxy]phenyl}pent-4-en-1-yl]benzoic Acid (Racemate)

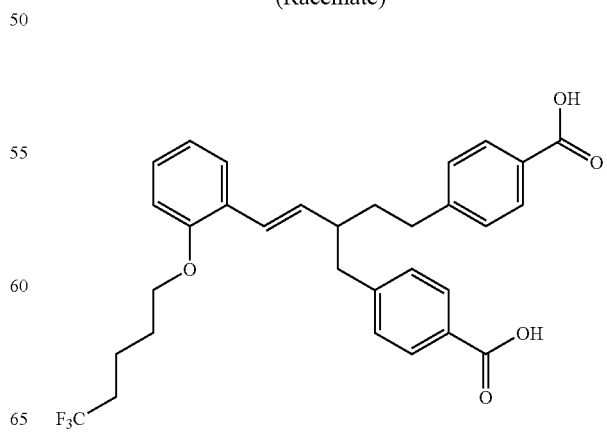

148 mg (0.27 mmol, 52% of theory) of the title compound are obtained by the process described in Example 11 starting from 280 mg (0.52 mmol) of methyl 4-[(3E)-2-[2-(4-cyanophenyl)ethyl]-4-{2-[(5,5,5-trifluoropentyl)oxy]phenyl}but-3-en-1-yl]benzoate and 1173 mg (20.9 mmol) of potassium hydroxide.

LC-MS (method 1): $R_t$=2.97 min; MS (ESIpos): m/z=541 (M+H)$^+$.

148 mg (0.27 mmol) of the 4-[(4E)-3-(4-carboxybenzyl)-5-{2-[(5,5,5-trifluoropentyl)oxy]-phenyl}pent-4-en-1-yl]benzoic Acid obtained in this way are further fractionated by preparative HPLC on a chiral phase. Respectively 71 mg and 55 mg of the two E-isomers are obtained in each case enantiopure (see Examples 42 and 43).

Example 42

4-[(4E)-3-(4-Carboxybenzyl)-5-{2-[(5,5,5-trifluoropentyl)oxy]phenyl}pent-4-en-1-yl]benzoic Acid (Enantiomer 1)

Enantiomer Separation Method:
Column: Daicel Chiralpak AD-H 250 mm×20 mm, 5 μm; eluent: isopropanol (with 1% water and 0.2% trifluoroacetic acid)/isohexane 23:77 (v/v); flow rate: 15 ml/min; UV detection: 215 nm; temperature: 30° C.

$R_t$ 9.58 min; purity: >99.5%; >99.5% ee
Yield: 71 mg
$^1$H-NMR (400 MHz, DMSO-d$_6$, δ/ppm): 12.77 (br. s, 2H), 7.90-7.77 (4H, m), 7.39 (1H, d), 7.33-7.22 (4H, m), 7.17 (1H, t), 6.94 (1H, d), 6.88 (1H, t), 6.42 (1H, d), 6.17-6.03 (1H, m), 4.02-3.89 (2H, m), 2.91-2.82 (1H, m), 2.79-2.68 (2H, m), 2.67-2.56 (1H, m), 2.55-2.41 (1H, m), 2.37-2.20 (2H, m), 1.88-1.72 (3H, m), 1.71-1.55 (3H, m).

Example 43

4-[(4E)-3-(4-Carboxybenzyl)-5-{2-[(5,5,5-trifluoropentyl)oxy]phenyl}pent-4-en-1-yl]benzoic Acid (Enantiomer 2)

Enantiomer separation method: see Example 42.
$R_t$ 11.18 min; purity: 99.5%; >99.5% ee
Yield: 55 mg
$^1$H-NMR: see Example 42.

Example 44

4-{(4E)-3-(4-Carboxybenzyl)-5-[2-({4-[1,2,2,2-tetrafluoro-1-(trifluoromethyl)ethyl]benzyl}oxy)-phenyl]pent-4-en-1-yl}benzoic Acid

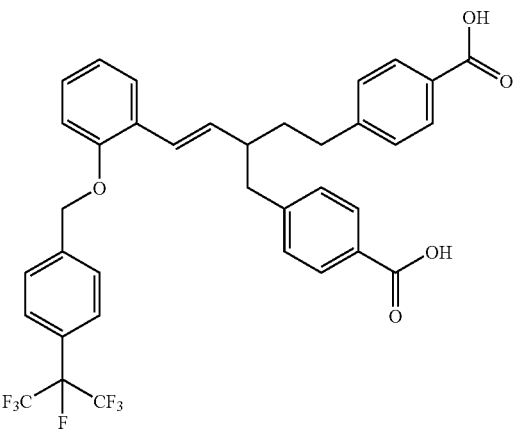 [SMILES: O=C(O)c1ccc(CCC(/C=C/c2ccccc2OCc2ccc(C(F)(C(F)(F)F)C(F)(F)F)cc2)Cc2ccc(C(=O)O)cc2)cc1]

A solution of 170 mg (0.25 mmol) of methyl 4-{(4E)-3-(4-cyanobenzyl)-5-[2-({4-[1,2,2,2-tetrafluoro-1-(trifluoromethyl)ethyl]benzyl}oxy)phenyl]pent-4-en-1-yl}benzoate in 3 ml of 1-propanol and 2 ml of water is mixed with 427 mg (7.6 mmol) of potassium hydroxide and stirred at 110° C. for 12 h. After cooling, the mixture is acidified with 1 M hydrochloric acid, and the crystals which have separated out are filtered off with suction, washed several times with water and dried. 135 mg (0.2 mmol, 79% of theory) of the title compound are obtained.

$^1$H-NMR (400 MHz, DMSO-d$_6$, δ/ppm): 12.75 (br. s, 2H), 7.88-7.76 (4H, m), 7.70-7.59 (4H, m), 7.43 (1H, d), 7.31-7.21 (4H, m), 7.18 (1H, t), 7.04 (1H, d), 6.92 (1H, t), 6.51 (1H, d), 6.19-6.07 (1H, m), 5.20 (2H, s), 2.92-2.81 (1H, m), 2.79-2.68 (2H, m), 2.67-2.58 (1H, m), 2.57-2.42 (1H, m), 1.85-1.72 (1H, m), 1.71-1.58 (1H, m).

LC-MS (method 7): $R_t$=3.18 min; MS (ESIpos): m/z=675 (M+H)$^+$.

The examples listed in the following table are obtained in an analogous manner:

| Example No. | Example structure [precursors] | Analytical data |
|---|---|---|
| 45 | ![structure] [starting from 1-(bromomethyl)-4-(trifluoromethoxy)benzene and Ex. 51A] | $^1$H-NMR (400 MHz, DMSO-d$_6$, δ/ppm): 13.10-12.00 (2H, broad), 7.89-7.75 (4H, m), 7.50 (2H, d), 7.43 (1H, d), 7.38 (2H, d), 7.31-7.21 (4H, m), 7.18 (1H, t), 7.01 (1H, d), 6.91 (1H, t), 6.49 (1H, d), 6.19-6.03 (1H, m), 5.11 (2H, s), 2.92-2.81 (1H, m), 2.79-2.66 (2H, m), 2.65-2.58 (1H, m), 2.57-2.42 (1H, m), 1.88-1.73 (1H, m), 1.72-1.59 (1H, m). LC-MS (method 7): $R_t$ = 3.06 min; m/z = 591 (M + H$^+$). |

| Example No. | Example structure [precursors] | Analytical data |
|---|---|---|
| 46 | [starting from 1-(bromomethyl)-4-(trifluoromethyl)benzene and Ex. 51A] | $^1$H-NMR (400 MHz, DMSO-d$_6$, δ/ppm): 12.77 (2H, br. s), 7.82 (4H, d), 7.71 (2H, d), 7.59 (2H, d), 7.44 (1H, d), 7.32-7.21 (4H, m), 7.19 (1H, t), 7.01 (1H, d), 6.92 (1H, t), 6.50 (1H, d), 6.19-6.05 (1H, m), 5.20 (2H, s), 2.91-2.81 (1H, m), 2.79-2.67 (2H, m), 2.66-2.57 (1H, m), 2.56-2.44 (1H, m), 1.88-1.74 (1H, m), 1.73-1.58 (1H, m). LC-MS (method 2): R$_t$ = 2.85 min; m/z = 575 (M + H$^+$). |
| 47 | [starting from 1-(bromomethyl)-2-(trifluoromethyl)benzene and Ex. 51A] | $^1$H-NMR (400 MHz, DMSO-d$_6$, δ/ppm): 12.74 (2H, br. s), 7.81-7.72 (5H, m), 7.71-7.62 (2H, m), 7.60-7.52 (1H, m), 7.43 (1H, d), 7.28-7.15 (5H, m), 7.01 (1H, d), 6.95 (1H, t), 6.45 (1H, d), 6.15-6.04 (1H, m), 5.21 (2H, s), 2.89-2.79 (1H, m), 2.76-2.62 (2H, m), 2.61-2.39 (2H, m), 1.84-1.70 (1H, m), 1.69-1.56 (1H, m). LC-MS (method 2): R$_t$ = 2.86 min; m/z = 575 (M + H$^+$). |
| 48 | [starting from 1-(bromomethyl)-3,5-bis(trifluoromethyl)benzene and Ex. 51A] | $^1$H-NMR (400 MHz, DMSO-d$_6$, δ/ppm): 12.74 (2H, br. s), 8.14 (2H, s), 8.07 (1H, s), 7.82.-7.71 (4H, m), 7.44 (1H, d), 7.29-7.17 (5H, m), 7.06 (1H, d), 6.95 (1H, t), 6.51 (1H, d), 6.21-6.08 (1H, m), 5.38-5.25 (2H, m), 2.91-2.79 (1H, m), 2.78-2.64 (2H, m), 2.63-2.41 (2H, m), 1.85-1.71 (1H, m), 1.70-1.56 (1H, m). LC-MS (method 2): R$_t$ = 2.94 min; m/z = 643 (M + H$^+$). |

-continued

| Example No. | Example structure [precursors] | Analytical data |
|---|---|---|
| 49 | (structure shown) [starting from Example 55A and Ex. 51A] | $^1$H-NMR (400 MHz, DMSO-d$_6$, δ/ppm): 12.76 (2H, br. s), 7.84-7.72 (6H, m), 7.63 (1H, d), 7.52 (2H, d), 7.37-7.17 (7H, m), 6.39 (1H, d), 6.26-6.13 (1H, m), 2.92-2.81 (1H, m), 2.79-2.63 (2H, m), 2.62-2.44 (2H, m), 1.87-1.74 (1H, m), 1.73-1.60 (1H, m). LC-MS (method 4): R$_t$ = 3.08 min; m/z = 625 (M − H$^-$). |
| 50 | (structure shown) [starting from 1-[chloro(difluoro)methyl]-4-(trifluoromethyl)benzene (CAS Reg. No. 13947-94-9) and Ex. 51A] | LC-MS (method 7): R$_t$ = 3.07 min; m/z = 609 (M − H$^-$). |
| 51 | (structure shown) [starting from 1-bromo-4-[bromo(difluoro)methyl]benzene (CAS Reg. No. 2358-32-9) and Ex. 51A] | $^1$H-NMR (400 MHz, DMSO-d$_6$, δ/ppm): 12.78 (2H, br. s), 7.80 (4H, d), 7.73 (2H, d), 7.62 (1H, d), 7.57 (2H, d), 7.35-7.17 (7H, m), 6.37 (1H, d), 6.25-6.12 (1H, m), 2.93-2.80 (1H, m), 2.79-2.63 (2H, m), 2.62-2.44 (2H, m), 1.87-1.73 (1H, m), 1.73-1.60 (1 H, m). LC-MS (method 2): R$_t$ = 3.03 min; m/z = 619 (M − H$^-$). |

-continued

| Example No. | Example structure [precursors] | Analytical data |
|---|---|---|
| 52 | 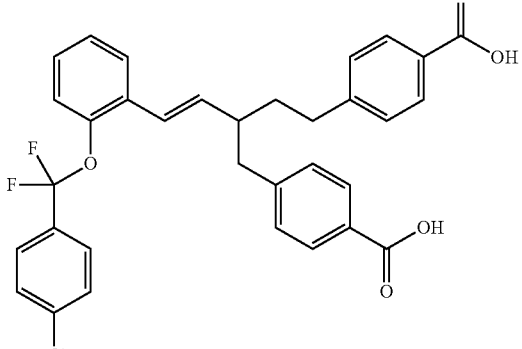<br>[starting from 1-[bromo(difluoro)methyl]-4-chlorobenzene (CAS Reg. No. 6987-14-0) and Ex. 51A] | $^1$H-NMR (400 MHz, DMSO-$d_6$, δ/ppm): 12.78 (2H, br. s), 7.83-7.75 (4H, m), 7.68-7.54 (5H, m), 7.36-7.18 (7H, m), 6.36 (1H, d), 6.25-6.13 (1H, m), 2.92-2.81 (1H, m), 2.79-2.64 (2H, m), 2.63-2.44 (2H, m), 1.87-1.73 (1H, m), 1.73-1.61 (1H, m). LC-MS (method 4): $R_t$ = 3.00 min; m/z = 575 (M − H)$^-$. |
| 53 | 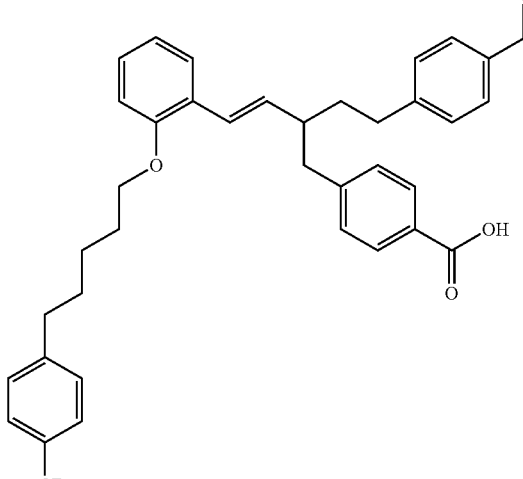<br>[starting from Ex. 53A and Ex. 51A] | $^1$H-NMR (400 MHz, DMSO-$d_6$, δ/ppm): 12.78 (2H, br. s), 7.89-7.74 (4H, m), 7.59 (2H, d), 7.40-7.32 (3H, m), 7.32-7.20 (4H, m), 7.16 (1H, t), 6.96-6.83 (2H, m), 6.42 (1H, d), 6.14-6.01 (1H, m), 3.99-3.84 (2H, m), 2.91-2.80 (1H, m), 2.79-2.68 (2H, m), 2.68-2.58 (2H, m), 2.57-2.40 (1H, m), 1.88-1.55 (7H, m), 1.48-1.31 (2H, m). LC-MS (method 4): $R_t$ = 3.29 min; m/z = 629 (M − H)$^-$. |

Example 54

4-[(4E)-3-(4-Carboxybenzyl)-5-(5-fluoro-2-{[4-(trifluoromethyl)benzyl]oxy}phenyl)pent-4-en-1-yl]benzoic Acid (Enantiomer 1)

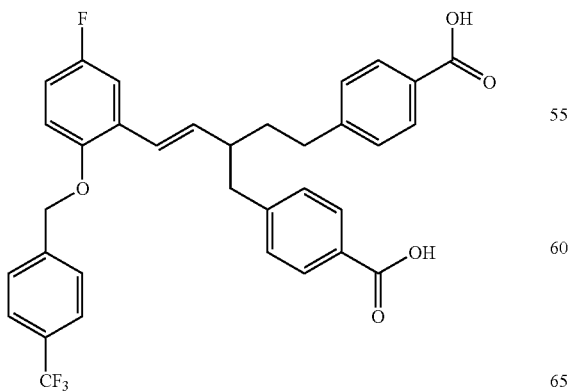

A solution of 523 mg (0.84 mmol) of methyl 4-{(4E)-5-(5-fluoro-2-{[4-(trifluoromethyl)benzyl]-oxy}phenyl)-3-[4-methoxycarbonyl)benzyl]pent-4-en-1-yl}benzoate (enantiomer 1, Example 65A) in 8 ml of THF and 4 ml of water is mixed with 101 mg (4.2 mmol) of lithium hydroxide and stirred at 50° C. for 12 h. After cooling, the mixture is acidified with 1 M hydrochloric acid, and the crystals which have separated out are filtered off with suction, washed several times with water and dried. 457 mg (0.77 mmol, 91% of theory) of the title compound are obtained.

$^1$H-NMR (400 MHz, DMSO-$d_6$, δ/ppm): 12.76 (br. s, 2H), 7.81 (4H, d), 7.21 (2H, d), 7.57 (2H, d), 7.33-7.21 (5H, m), 7.08-6.96 (2H, m), 6.47 (1H, d), 6.29-6.17 (1H, m), 5.17 (2H, s), 2.92-2.82 (1H, m), 2.79-2.66 (2H, m), 2.65-2.57 (1H, m), 2.56-2.45 (1H, m), 1.88-1.75 (1H, m), 1.74-1.61 (1H, m).

LC-MS (method 8): $R_t$=4.23 min; MS (ESIpos): m/z=593 (M+H)$^+$.

The examples listed in the following table are obtained in an analogous manner:

| Example No. | Example structure [precursor] | Analytical data |
|---|---|---|
| 55 | 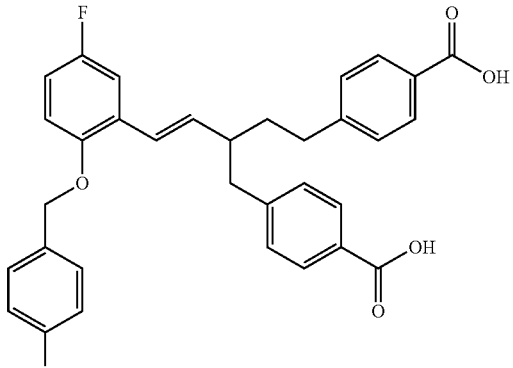<br>(Enantiomer 2)<br>[starting from Ex. 66A] | $^1$H-NMR: see Ex. 54<br>LC-MS (method 2): $R_t$ = 2.82 min; m/z = 593 (M + H$^+$). |
| 56 | 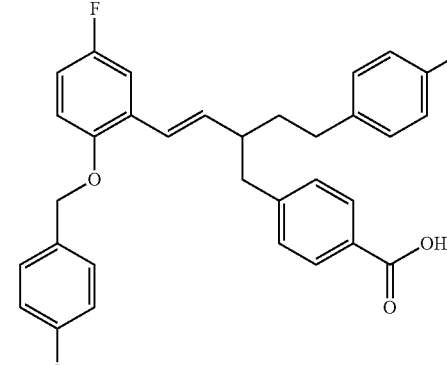<br>(Enantiomer 1)<br>[starting from Ex. 68A] | $^1$H-NMR (400 MHz, DMSO-$d_6$, δ/ppm): 12.78 (2H, br. s), 7.89-7.74 (4H, m), 7.48 (2H, d), 7.33 (2H, d), 7.31-7.19 (5H, m), 7.10-6.94 (2H, m), 6.43 (1H, d), 6.28-6.14 (1H, m), 5.08 (2H, s), 3.93-2.80 (1H, m), 2.79-2.67 (2H, m), 2.66-2.58 (1H, m), 2.57-2.41 (1H, m), 1.87-1.74 (1H, m), 1.73-1.60 (1H, m).<br>LC-MS (method 2): $R_t$ = 2.84 min; m/z = 607 (M − H$^-$). |

| Example No. | Example structure [precursor] | Analytical data |
|---|---|---|
| 57 | 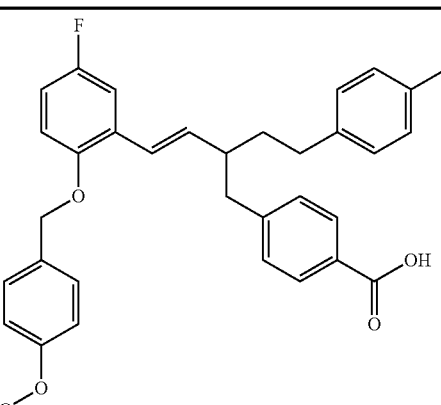<br>(Enantiomer 2)<br>[starting from Ex. 69A] | ¹H-NMR: see Ex. 56<br>LC-MS (method 2): $R_t$ = 2.84 min; m/z = 607 (M − H⁻). |

Example 58

4-[(4E)-3-(4-Carboxybenzyl)-5-{2-[(6-phenylhexyl)oxy]phenyl}pent-4-en-1-yl]benzoic Acid (Racemate)

Example 59

4-[(4E)-3-(4-Carboxybenzyl)-5-(2-{4-[4-(trifluoromethyl)phenoxy]butoxy}phenyl)pent-4-en-1-yl]benzoic Acid

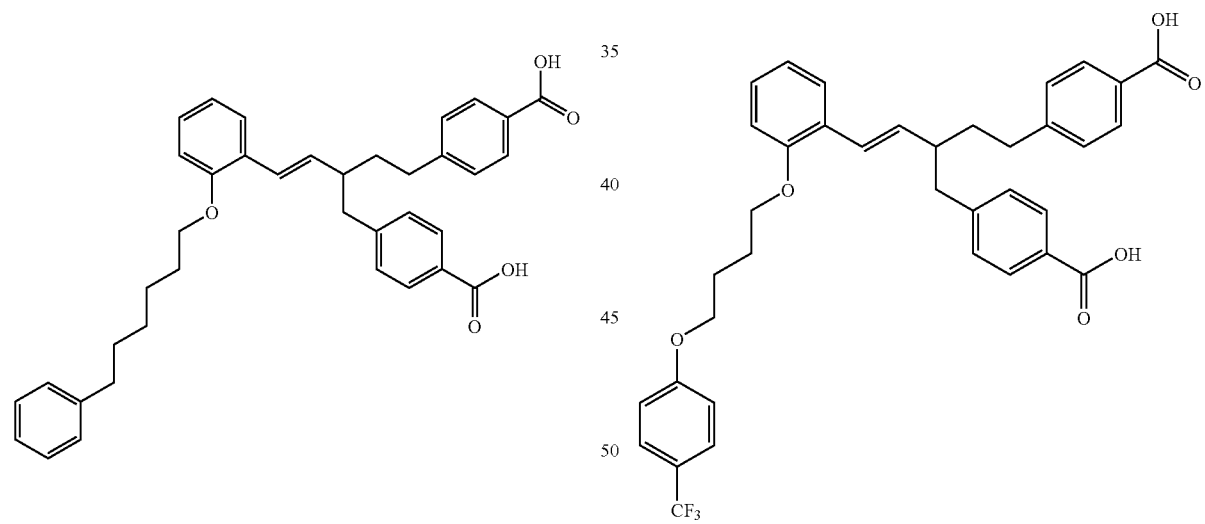

A solution of 360 mg (0.48 mmol; purity 76%) of methyl 4-[(3E)-2-[2-(4-cyanophenyl)ethyl]-4-{2-[(6-phenylhexyl)oxy]phenyl}but-3-en-1-yl]benzoate in 15 ml of 1-propanol is mixed with 1452 mg (25.9 mmol) of potassium hydroxide and stirred at 110° C. for 12 h. After cooling, the mixture is acidified with 1 M hydrochloric acid, and the crystals which have separated out are filtered off with suction, washed several times with water and dried. 22 mg (0.04 mmol, 8% of theory) of the title compound are obtained.

LC-MS (method 6): $R_t$=6.97 min; MS (ESIpos): m/z=577 (M+H)⁺.

A solution of 450 mg (0.72 mmol) of methyl 4-[(4E)-3-(4-cyanobenzyl)-5-(2-{4-[4-(trifluoromethyl)phenoxy]butoxy}phenyl)pent-4-en-1-yl]benzoate in 15 ml of 1-propanol and 2 ml of water is mixed with 1207 mg (21.5 mmol) of potassium hydroxide and stirred at 110° C. for 12 h. After cooling, the mixture is acidified with 1 M hydrochloric acid, and the crystals which have separated out are filtered off with suction, washed several times with water and dried. 447 mg (0.65 mmol, 90% of theory, purity 92%) of the title compound are obtained.

¹H-NMR (400 MHz, DMSO-$d_6$, δ/ppm): 12.78 (br. s, 2H), 7.91-7.75 (4H, m), 7.60 (2H, d), 7.39 (1H, d), 7.33-7.20 (4H, m), 7.19 (1H, t), 7.07 (2H, d), 6.94 (1H, d), 6.88 (1H, t), 6.44 (1H, d), 6.18-6.03 (1H, m), 4.12-4.05 (2H, m), 4.04-3.91 (2H, m), 2.91-2.79 (1H, m), 2.78-2.64 (2H, m), 2.63-2.40 (2H, m), 1.95-1.72 (5H, m), 1.72-1.56 (1H, m).

LC-MS (method 4): $R_t$=3.16 min; MS (ESIpos): m/z=633 $(M+H)^+$.

Example 60

4-[(4E)-3-(4-Carboxybenzyl)-5-{2-[4-(4-fluorophenoxy)butoxy]phenyl}pent-4-en-1-yl]benzoic Acid

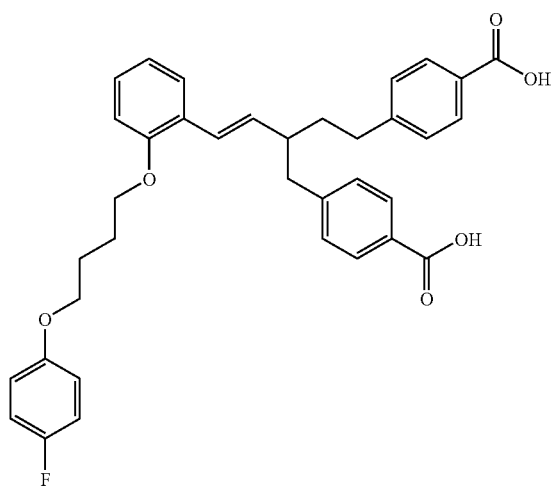 [SMILES: O=C(O)c1ccc(CCC(/C=C/c2ccccc2OCCCCOc2ccc(F)cc2)Cc2ccc(C(=O)O)cc2)cc1]

A solution of 460 mg (0.80 mmol) of methyl 4-[(4E)-3-(4-cyanobenzyl)-5-{2-[4-(4-fluorophenoxy)butoxy]phenyl}pent-4-en-1-yl]benzoate in 15 ml of 1-propanol and 2 ml of water is mixed with 1340 mg (23.89 mmol) of potassium hydroxide and stirred at 110° C. for 12 h. After cooling, the mixture is acidified with 1 M hydrochloric acid, and the crystals which have separated out are filtered off with suction, washed several times with water and dried. 325 mg (0.52 mmol, 65% of theory, purity 93%) of the title compound are obtained.

$^1$H-NMR (400 MHz, DMSO-$d_6$, δ/ppm): 12.78 (br. s, 2H), 7.89-7.77 (4H, m), 7.38 (1H, d), 7.32-7.21 (4H, m), 7.18 (1H, t), 7.08 (2H, t), 6.94 (1H, d), 6.92-6.83 (3H, m), 6.44 (1H, d), 6.17-6.04 (1H, m), 4.07-3.90 (4H, m), 2.91-2.81 (1H, m), 2.79-2.66 (2H, m), 2.66-2.56 (1H, m), 2.54-2.41 (1H, m), 1.90-1.72 (5H, m), 1.71-1.56 (1H, m).

LC-MS (method 4): $R_t$=3.04 min; MS (ESIpos): m/z=583 $(M+H)^+$.

B. ASSESSMENT OF THE PHARMACOLOGICAL ACTIVITY

The pharmacological effect of the compounds according to the invention can be shown in the following assays:

B-1. Vasorelaxant Effect In Vitro:

Rabbits are anaesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with 95% $O_2$/5% $CO_2$ and has the following composition: NaCl 119 mM; KCl 4.8 mM; $CaCl_2 \times 2H_2O$ 1 mM; $MgSO_4 \times 7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 μl. The proportion of DMSO in the bath solution corresponds to 0.1%.

Representative results on the compounds according to the invention are listed in Table 1:

TABLE 1

| Vasorelaxant effect in vitro | |
|---|---|
| Example No. | $IC_{50}$ [nM] |
| 2 | 0.54 |
| 3 | 4.7 |
| 5 | 4.9 |
| 6 | 121.5 |
| 7 | 21 |
| 10 | 48 |
| 11 | 129 |
| 13 | 52.2 |
| 17 | 1.1 |
| 20 | 0.7 |
| 42 | 19 |
| 44 | 22 |
| 45 | 6 |
| 48 | 4 |
| 50 | 370 |
| 54 | 90 |
| 55 | 287 |
| 56 | 77 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the haem-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", J. Mol. Med. 77 (1999), 14-23. The haem-free guanylate cyclase is obtained by adding Tween 20 to the sample buffer (0.5% in the final concentration).

The activation of sGC by a test substance is reported as n-fold stimulation of the basal activity. The result for Example 5 is shown in Table 2:

TABLE 2

Stimulation (n-fold) of recombinant soluble guanylate cyclase (sGC) in vitro by Example 5

| Concentration of Example 5 [μM] | Haem-containing sGC | | | Haem-free sGC | |
|---|---|---|---|---|---|
| | Basal | +0.1 μM DEA/NO | +10 μM ODQ | Basal | +10 μM ODQ |
| 0.0 | 1.0 | 78.7 | 38.8 | 1.0 | 2.0 |
| 0.001 | 3.5 | 88.3 | 40.3 | 19.2 | 18.4 |
| 0.01 | 17.2 | 102.9 | 83.0 | 105.8 | 100.5 |
| 0.1 | 35.1 | 123.1 | 149.5 | 185.3 | 170.4 |
| 1 | 44.2 | 124.1 | 162.1 | 201.2 | 189.2 |
| 10 | 59.5 | 152.0 | 171.2 | 203.1 | 180.7 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the haem-containing and of the haem-free enzyme is achieved. Furthermore, combination of Example 5 and 2-(N,N-diethylamino)diazenolate 2-oxide (DEA/NO), an NO donor, shows no synergistic effect, i.e. the effect of DEA/NO is not potentiated as would be expected with an sGC activator acting via a haem-dependent mechanism. In addition, the effect of the sGC activator according to the invention is not blocked by the haem-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

The compound of Example 20 shows a marked reduction in blood pressure over a period of 11 hours after oral administration of 0.3 mg/kg in this test.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I-A)

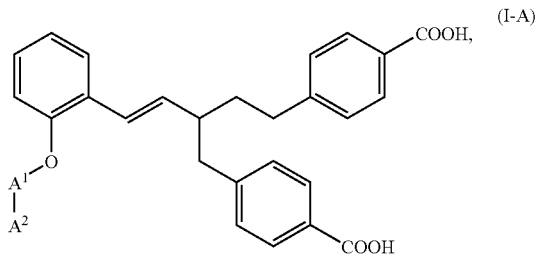

(I-A)

in which
$A^1$ is $(C_1-C_7)$-alkanediyl
and
$A^2$ is hydrogen or a group of the formula

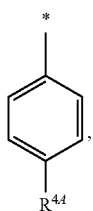

in which * is the point of linkage to the group $A^1$ and
$R^{4A}$ is hydrogen, fluorine, chlorine, methyl, tert-butyl, trifluoromethyl, methoxy or trifluoromethoxy,
or the salts, solvates and solvates of the salts thereof.

2. A compound of formula (I-B)

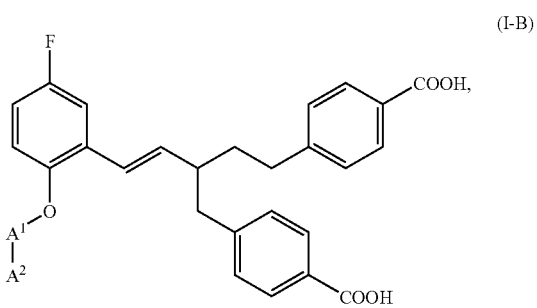

(I-B)

in which
$A^1$ is $(C_1-C_7)$-alkanediyl
and
$A^2$ is hydrogen or a group of the formula

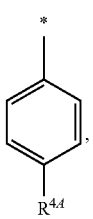

in which * is the point of linkage to the group $A^1$ and
$R^{4A}$ is hydrogen, fluorine, chlorine, methyl, tert-butyl, trifluoromethyl, methoxy or trifluoromethoxy,
or the salts, solvates and solvates of the salts thereof.

3. A method for preparing a compound of formula (I-A) as defined in claim 1, comprising:
reacting a compounds of formula (II)

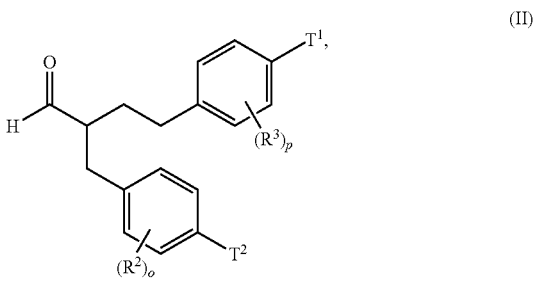

(II)

in which
$R^2$ and $R^3$ are independently of one another a substituent selected from the series halogen, $(C_1-C_6)$-alkyl, trifluoromethyl, $(C_1-C_6)$-alkoxy, trifluoromethoxy, cyano and nitro,
where in the case where $R^2$ or $R^3$ occur more than once, their meanings may in each case be identical or different,
o and p are in each case independently of one another the number 0, 1, 2, 3, or 4, and
$T^1$ and $T^2$ are identical or different and are cyano or $(C_1-C_4)$-alkoxycarbonyl, either

[A] in an inert solvent in the presence of a base with a compound of formula (III-A)

(III-A)

in which A is a group of formula —O-$A^1$-$A^2$, and $A^1$ and $A^2$ each have the meanings indicated in claim 1, $R^1$ is a substituent selected from the series halogen, ($C_1$-$C_6$)-alkyl, trifluoromethyl, ($C_1$-$C_6$)-alkoxy, trifluoromethoxy, cyano and nitro, and in the case where $R^1$ occurs more than once, its meaning in each case may be identical or different, n is the number 0, 1, 2, 3 or 4, L is phenyl or o-, m- or p-tolyl and X is halide or tosylate, to give a compound of formula (IV-A)

(IV-A)

in which A, $R^1$, $R^2$, $R^3$, n, o, p, $T^1$ and $T^2$ each have the meanings indicated above, or

[B] in an inert solvent in the presence of a base with a compound of formula (III-B)

(III-B)

in which $R^1$, n, L and X each have the meanings indicated above, to give a compound of formula (IV-B)

(IV-B)

in which $R^1$, $R^2$, $R^3$, n, o, p, $T^1$ and $T^2$ each have the meanings indicated above, and alkylating the compound of formula (IV-B) in an inert solvent in the presence of a base with a compound of formula (V)

$$A^2\text{-}A^{1A}Q \tag{V},$$

in which $A^2$ has the meaning indicated in claim 1, $A^{1A}$ has the meaning indicated in claim 1, for $A^1$ but is not a bond, and Q is a leaving group, to give a compound of the formula (IV-C)

(IV-C)

in which $A^{1A}$, $A^2$, $R^1$, $R^2$, $R^3$, n, o, p, $T^1$ and $T^2$ each have the meanings indicated above, and converting the resulting compound of the formula (IV-A) or (IV-C) by hydrolysis of the ester or nitrile groups $T^1$ and $T^2$ into a compound of formula (I-A), and optionally reacting the compound of formula (I-A) with an appropriate (i) solvent and/or (ii) base or acid to give a salt thereof.

4. A pharmaceutical composition comprising a compound of claim 1 or 2 and an inert, non-toxic, pharmaceutically suitable excipient.

5. The pharmaceutical composition according to claim 4, further comprising an active ingredient selected from the group consisting of an organic nitrate, an NO donor, a cGMP-PDE inhibitor, a stimulator of guanylate cyclase, an agent having antithrombotic activity, an agent lowering blood pressure, and an agent altering lipid metabolism.

6. A method for preparing a compound of formula (I-B) as defined in claim 2, comprising:
reacting a compound of formula (II)

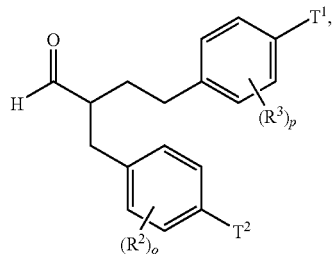

in which $R^2$ and $R^3$ are independently of one another a substituent selected from the series halogen, $(C_1\text{-}C_6)$-alkyl, trifluoromethyl, $(C_1\text{-}C_6)$-alkoxy, trifluoromethoxy, cyano and nitro,
where in the case where $R^2$ or $R^3$ occur more than once, their meanings may in each case be identical or different,
o and p are in each case independently of one another the number 0, 1, 2, 3, or 4, and
$T^1$ and $T^2$ are identical or different and are cyano or $(C_1\text{-}C_4)$-alkoxycarbonyl,
either
[A] in an inert solvent in the presence of a base with a compound of formula (III-A)

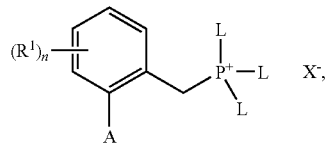

in which A is a group of formula —O-$A^1$-$A^2$, and $A^1$ and $A^2$ each have the meanings indicated in claim 2
$R^1$ is a substituent selected from the series halogen, $(C_1\text{-}C_6)$-alkyl, trifluoromethyl, $(C_1\text{-}C_6)$-alkoxy, trifluoromethoxy, cyano and nitro, and in the case where $R^1$ occurs more than once, its meaning in each case may be identical or different,
n is the number 0, 1, 2, 3 or 4,
L is phenyl or o-, m- or p-tolyl
and
X is halide or tosylate,
to give a compound of formula (IV-A)

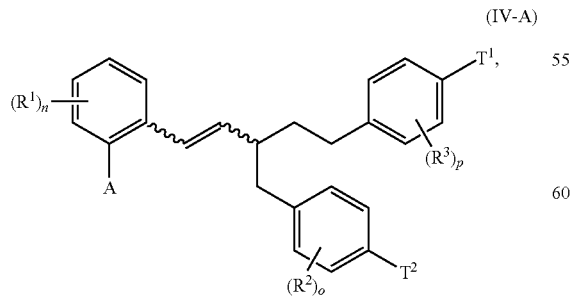

in which A, $R^1$, $R^2$, $R^3$, n, o, p, $T^1$ and $T^2$ each have the meanings indicated above, or
[B] in an inert solvent in the presence of a base with a compound of formula (III-B)

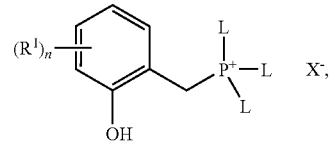

in which $R^1$, n, L and X each have the meanings indicated above,
to give a compound of formula (IV-B)

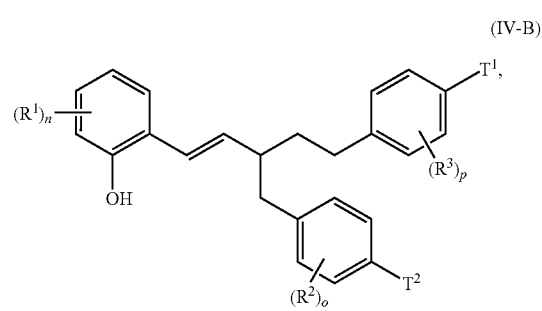

in which $R^1$, $R^2$, $R^3$, n, o, p, $T^1$ and $T^2$ each have the meanings indicated above,
and alkylating the compound of formula (IV-B) in an inert solvent in the presence of a base with a compound of formula (V)

$$A^2\text{-}A^{1A}\text{-}Q \qquad (V),$$

in which $A^2$ has the meaning indicated in claim 2,
$A^{1A}$ has the meaning indicated in claim 2 for $A^1$ but is not a bond,
and
Q is a leaving group,
to give a compound of the formula (IV-C)

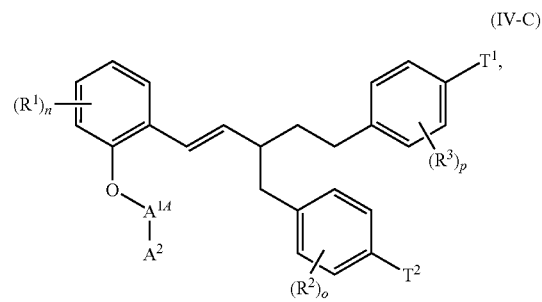

in which $A^{1A}$, $A^2$, $R^1$, $R^2$, $R^3$, n, o, p, $T^1$ and $T^2$ each have the meanings indicated above,
and converting the resulting compound of the formula (IV-A) or (IV-C) by hydrolysis of the ester or nitrile groups $T^1$ and $T^2$ into a compound of formula (1-B),
and optionally reacting the compound of formula (I-B) with an appropriate (i) solvent and/or (ii) base or acid to give a salt thereof.

7. A compound of formula:
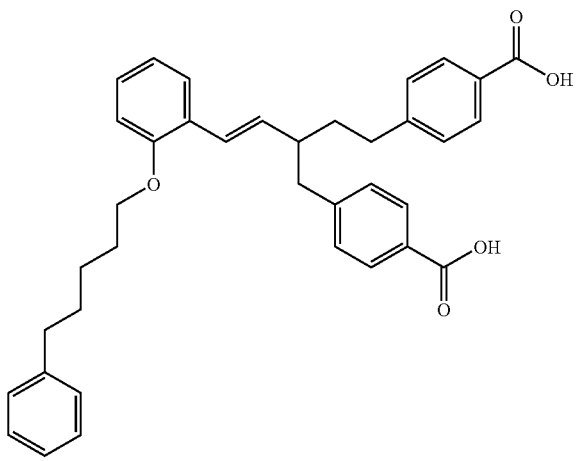 [SMILES: O=C(O)c1ccc(CCC(/C=C/c2ccccc2OCCCCCc2ccccc2)Cc2ccc(C(=O)O)cc2)cc1]
or a salt, a solvate, or a solvate of a salt thereof.
8. The compound of claim 7, wherein the compound is enantiomer I of the formula.
9. A compound of formula:
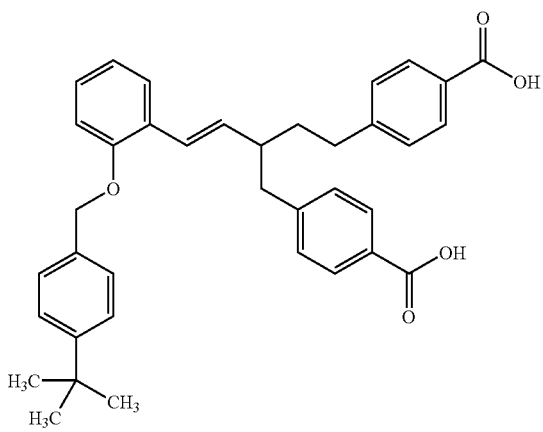 [SMILES: CC(C)(C)c1ccc(COc2ccccc2/C=C/C(CCc2ccc(C(=O)O)cc2)Cc2ccc(C(=O)O)cc2)cc1]
or a salt, a solvate, or a solvate of a salt thereof.
* * * * *